US011664092B2

(12) United States Patent
Blume et al.

(10) Patent No.: US 11,664,092 B2
(45) Date of Patent: May 30, 2023

(54) LUNG BIOMARKERS AND METHODS OF USE THEREOF

(71) Applicant: PrognomIQ, Inc., San Mateo, CA (US)

(72) Inventors: John E. Blume, Bellingham, WA (US); William C. Manning, Redwood City, CA (US); Gregory Troiano, San Mateo, CA (US); Asim Siddiqui, San Francisco, CA (US); Philip Ma, San Jose, CA (US); Omid C. Farokhzad, Waban, MA (US)

(73) Assignee: PrognomIQ, Inc., San Mateo, CA (US)

( * ) Notice: Subject to any disclaimer, the term of this patent is extended or adjusted under 35 U.S.C. 154(b) by 0 days.

(21) Appl. No.: 17/585,303

(22) Filed: Jan. 26, 2022

(65) Prior Publication Data

US 2022/0148680 A1 May 12, 2022

Related U.S. Application Data

(63) Continuation of application No. PCT/US2021/015339, filed on Jan. 27, 2021.

(60) Provisional application No. 62/967,995, filed on Jan. 30, 2020.

(51) Int. Cl.
| *G16B 40/10* | (2019.01) |
| *G16H 10/40* | (2018.01) |
| *G16H 50/70* | (2018.01) |
| *G01N 33/543* | (2006.01) |
| *G01N 33/552* | (2006.01) |
| *G01N 33/574* | (2006.01) |
| *G01N 30/86* | (2006.01) |

(52) U.S. Cl.
CPC ....... *G16B 40/10* (2019.02); *G01N 33/54326* (2013.01); *G01N 33/54346* (2013.01); *G01N 33/552* (2013.01); *G01N 33/57423* (2013.01); *G16H 10/40* (2018.01); *G16H 50/70* (2018.01); *G01N 30/8686* (2013.01)

(58) Field of Classification Search
CPC .............. G16B 40/10; G01N 30/8686
See application file for complete search history.

(56) References Cited

U.S. PATENT DOCUMENTS

| 7,632,686 | B2 | 12/2009 | Anderson |
| 7,906,758 | B2 | 3/2011 | Stults et al. |
| 9,002,652 | B1 | 4/2015 | Hood et al. |
| 9,005,994 | B2 | 4/2015 | Huo |
| 9,234,895 | B2 | 1/2016 | Hood et al. |
| 9,589,374 | B1 | 3/2017 | Gao et al. |
| 10,466,230 | B2 | 11/2019 | Stults et al. |
| 10,829,816 | B2 | 11/2020 | Staker et al. |
| 10,866,242 | B2 | 12/2020 | Farokhzad et al. |
| 11,085,931 | B2 | 8/2021 | Warthoe |
| 2004/0213446 | A1 | 10/2004 | Shams et al. |
| 2006/0008618 | A1 | 1/2006 | Wang et al. |
| 2007/0259363 | A1 | 11/2007 | Amri et al. |
| 2008/0187207 | A1 | 8/2008 | Bhanot et al. |
| 2008/0291122 | A1 | 11/2008 | Smith et al. |
| 2009/0090855 | A1 | 4/2009 | Kobold et al. |
| 2009/0176228 | A1 | 7/2009 | Birse et al. |
| 2010/0042329 | A1 | 2/2010 | Hood et al. |
| 2010/0188075 | A1 | 7/2010 | Litvinov et al. |
| 2011/0117582 | A1 | 5/2011 | Malima et al. |
| 2011/0171323 | A1 | 7/2011 | Weiss |
| 2011/0215237 | A1 | 9/2011 | Bateman |
| 2012/0046184 | A1 | 2/2012 | Dawson et al. |
| 2013/0080073 | A1 | 3/2013 | De Corral |
| 2013/0217057 | A1 | 8/2013 | Kearney et al. |
| 2014/0063009 | A1 | 3/2014 | Buehler et al. |
| 2014/0106976 | A1 | 4/2014 | Sachs et al. |
| 2015/0105276 | A1 | 4/2015 | Hofmann et al. |
| 2015/0253341 | A1 | 9/2015 | McAvoy et al. |
| 2016/0032395 | A1 | 2/2016 | Davicioni et al. |
| 2016/0054300 | A1 | 2/2016 | Winther et al. |
| 2016/0154006 | A1 | 6/2016 | Hermanson et al. |
| 2016/0260594 | A1 | 9/2016 | Hendricks |
| 2017/0024641 | A1 | 1/2017 | Wierzynski |
| 2017/0076195 | A1 | 3/2017 | Yang et al. |
| 2017/0220734 | A1 | 8/2017 | Colavin et al. |
| 2018/0067119 | A1* | 3/2018 | Kearney .......... G01N 33/57423 |
| 2018/0086713 | A1 | 3/2018 | Elkon et al. |
| 2018/0172694 | A1* | 6/2018 | Farokhzad ......... G01N 33/5308 |
| 2018/0275143 | A1 | 9/2018 | Wilcox et al. |
| 2019/0018019 | A1 | 1/2019 | Shan et al. |
| 2019/0147983 | A1 | 5/2019 | Shan et al. |
| 2019/0328837 | A1 | 10/2019 | Kim et al. |

(Continued)

FOREIGN PATENT DOCUMENTS

| CA | 2787201 A1 | 7/2011 |
| CN | 109470859 | 3/2019 |
| EP | 2124051 A1 | 11/2009 |
| EP | 2524219 A2 | 11/2012 |
| EP | 3510402 A1 | 7/2019 |
| EP | 3554681 A1 | 10/2019 |
| EP | 4096694 A1 | 12/2022 |
| GB | 2603051 A | 7/2022 |

(Continued)

OTHER PUBLICATIONS

Falahati et al., A health concern regarding the protein corona, aggregation and disaggregation, 2019, BBA-General Subjects, 1863, p. 971-991 (Year: 2019).*

(Continued)

*Primary Examiner* — Mary K Zeman
*Assistant Examiner* — Kaitlyn L Minchella
(74) *Attorney, Agent, or Firm* — Wilson Sonsini Goodrich & Rosati

(57) ABSTRACT

Disclosed herein are biomarkers associated with a disease state such as lung cancer, and methods of discovering or using biomarkers. Also disclosed herein are classifiers built on biomarkers and methods of detecting the disease state in samples from subjects. The method may include obtaining a data set that includes protein information from a biofluid sample, and may involve using a classifier to identify the sample as indicative of a healthy state, a disease state, or a comorbidity.

15 Claims, 18 Drawing Sheets

(56) References Cited

U.S. PATENT DOCUMENTS

| | | |
|---|---|---|
| 2020/0025765 A1 | 1/2020 | Arrazubi et al. |
| 2020/0025766 A1 | 1/2020 | Hanash et al. |
| 2020/0381083 A1 | 12/2020 | Chen |
| 2021/0005327 A1 | 1/2021 | Anwar et al. |
| 2021/0017598 A1 | 1/2021 | Jain et al. |
| 2021/0031166 A1 | 2/2021 | Porter et al. |
| 2021/0072255 A1 | 3/2021 | Farokhzad et al. |
| 2021/0098083 A1 | 4/2021 | Ma et al. |
| 2021/0132071 A1 | 5/2021 | Kostarelos et al. |
| 2021/0174958 A1 | 6/2021 | Drake et al. |
| 2021/0302416 A1 | 9/2021 | Soldo et al. |
| 2022/0259202 A1 | 8/2022 | Meimetis |
| 2022/0260559 A1 | 8/2022 | Blume et al. |
| 2022/0299527 A1 | 9/2022 | Bateman et al. |

FOREIGN PATENT DOCUMENTS

| | | | |
|---|---|---|---|
| WO | WO-2008114917 A1 | 9/2008 | |
| WO | WO-2010097785 A1 | 9/2010 | |
| WO | WO-2014078855 A1 | 5/2014 | |
| WO | WO-2017192965 A2 | 11/2017 | |
| WO | WO-2018046542 A1 | 3/2018 | |
| WO | WO-2018112460 A1 | 6/2018 | |
| WO | WO-2018170518 A1 | 9/2018 | |
| WO | WO-2019050966 A2 | 3/2019 | |
| WO | WO-2019182885 A1 | 9/2019 | |
| WO | WO-2019200410 A1 | 10/2019 | |
| WO | WO-2019209888 A1 | 10/2019 | |
| WO | WO-2020096631 A2 | 5/2020 | |
| WO | WO-2020198209 A1 | 10/2020 | |
| WO | WO-2021026172 A1 | 2/2021 | |
| WO | WO-2021087407 A1 | 5/2021 | |
| WO | WO-2021154893 A1 | 8/2021 | |
| WO | WO-2022020272 A1 | 1/2022 | |
| WO | WO-2022072471 | 4/2022 | |
| WO | WO-2022182989 A1 | 9/2022 | |
| WO | WO-2022212583 A1 | 10/2022 | |
| WO | WO-2023039479 | 3/2023 | |

OTHER PUBLICATIONS

Caracciolo et al., Disease-specific protein corona sensor arrays may have disease detection capacity, 2019, Nanoscale Horiz., 4, p. 1063-1076 (Year: 2019).*

Domenico et al., Nanoparticle-biomolecular corona: A new approach for the early detection of non-small-cell lung cancer, 2019, J Cell Physiol., 234, p. 9378-9386 (Year: 2019).*

Hadjidemetriou, Liposome protein corona in vivo: from fundamental principles to a tool for cancer biomarker discovery, 2017, University of Manchester, p. 1-233 (Year: 2017).*

Hammerschmidt et al., Lung Cancer: Current Diagnosis and Treatment, 2009, Dtsch Arztebl, 106(49), p. 809-820 (Year: 2009).*

Shriwash et al., Identification of differentially expressed genes in small and non-small cell lung cancer based on meta-analysis of mRNA, 2019, Heliyon, 5, p. 1-9 (Year: 2019).*

Acharjee et al. Integration of metabolomics, lipidomics and clinical data using a machine learning method. BMC Bioinformatics. 2016; 17(Suppl 15): 37-49.

"Adalsteinsson, V.A., Ha, G., Freeman, S.S et al. Scalable whole-exome sequencing of cell-free DNA reveals high concordance with metastatic tumors. Nat Commun 8, 1324 (2017). https://doi.org/10.1038/S41467-017-00965-y".

"ALBERS, et al., Dating genomic variants and shared ancestry in population-scale sequencing data. PLOS Biology, Jan. 2020, https://doi.org/10.1371/journal.pbio.3000586".

Alcalá et al. The Anthrax Toxin receptor 1 (ANTXR1) Is enriched in pancreatic cancer stem cells derived from primary tumor cultures. Stem Cells International, 2019, Article ID:1378639.

Altobelli et al. HtrA1: Its future potential as a novel biomarker for cancer. Oncology Reports, 2015, 34:555-566.

"Armagan, et al., Generalized Beta Mixtures of Gaussians. Advances in neutral information processing systems. 2011.".

Arroyo et al. Expression-based, consistent biomarkers for prognosis and diagnosis in lung cancer Clin Transl Oncol, 2020; 22(10):1867-1874.

Bell et al. A Hupo test sample study reveals common problems in mass spectrometry-based proteomics. Nat Methods. Jun. 2009; 6(6): 423-430.

Benjamini e al. Controlling the false discovery rate: a practical and powerful approach to multiple testing. Journal of the Royal Statistical Society. Series B (Methodological), pp. 289-300 (1995).

Blume, et al., Rapid, deep and precise profiling of the plasma proteome with multi-nanoparticle protein corona. Nature Communications, 2020; 11(3662): 1-14.

Bresnick et al. S100 proteins in cancer. Nature Reviews Cancer, 2015, 15:96-109.

"Butler et al., Lipids and Cancer: Emerging roles in pathogenesis, diagnosis and therapeutic intervention. Advanced Drug Delivery Review. 2020; 159:245-293".

Carbone et al. Angiopoietin-Like proteins in Angiogenesis, Inflammation and cancer. Int J Mol Sci. Feb. 2018; 19(2): 431 (1-22).

"Chantada-Vazquez, et al., Identification of a Profile of Neutrophil-Derived Granule Proteins in the Surface of Gold Nanoparticles after Their Interaction with Human Breast Cancer Sera. Nanomaterials (Basel, Switzerland), 2020; 10(1223): 1-18. https://doi.org/10.3390/nano10061223".

Chen et al. Network analysis of differentially expressed smoking-associated mRNAs, lncRNAs and miRNAs reveals key regulators in smoking-associated lung cancer. Exp. Ther. Med., 2018;16: 4991-5002.

Cho et al. Serum amyloid A is elevated in the serum of lung cancer patients with poor prognosis. Br J Cancer. 2010, 102(12): 1731-1735.

"Choi, et al., DUX4 recruits p300/CBP through its C-terminus and induces global H3K27 acetylation changes. Nucleic Acids Research, 2016. vol. 44m No. 11, 5161-5173.".

"Schwenk, et al., The Human plasma proteome draft of 2017: Building on the human plasma peptideatlas from mass spectrometry and complementary assays. Journal Proteome Research, Dec. 2017; 16(12): 4299-4310.".

Co-pending U.S. Appl. No. 17/709,185, inventors Maphilip et al., filed Mar. 30, 2022.

Co-pending U.S. Appl. No. 17/709,202, inventors Maphilip et al., filed Mar. 30, 2022.

Co-pending U.S. Appl. No. 17/720,197, inventors Blumejohn; E. et al., filed Apr. 13, 2022.

"Corley, et al., Adenoma Detection Rate and Risk of Colorectal Cancer and Death. New Engl J Med Apr. 2014; 370:1298-1306.".

Dougan et al. Proteomics-Metabolomics Combined Approach Identifies Peroxidasin as a Protector against Metabolic and Oxidative Stress in Prostate Cancer. Int. J. Mol. Sci., 2019, 20(12):3046.

Epelbaum et al. Haptoglobin-related protein as a Serum marker in Malignant Lymphoma. Pathology Oncology Research, 1998, 4(4):271-276.

Fan et al. Intelligence Algorithms for Protein Classification by Mass Spectrometry. BioMed Research International, vol. 2018, Article ID 2862458, 11 pages, 2018.

"Fredolini, et al., Shotgun proteomics coupled tonanoparticle-based biomarker enrichment reveals a novel panel of extracellular matrix proteins as candidate serum protein biomarkers for early-stage breast cancer detection. Breast Cancer Research (2020) 22:135https://doi.org/10.1186/s13058-020-01373-9".

"Gao, et al., "A latent factor model with a mixture of sparse and dense factors to model gene expression data with confounding effects." arXiv preprint arXiv:1310.4792 (2013).".

"Gao, et al., Evaluation of Serum CEA, CA19-9, CA72-4, CA125 and Ferritin as Diagnostic markers and factors of clinical parameters for colorectal cancer. Science Reports, 2018; 8:2732.".

Geary et al. Identification of a Biomarker Panel for Early Detection of Lung Cancer patients. J. Proteome Res. 2019, 18, 9, 3369-3382.

Gould et al. Recent trends in the identification of incidental pulmonary nodules. Am J Respir Crit Care Med. Nov. 15, 2015;192(10):1208-14.

(56) References Cited

OTHER PUBLICATIONS

Graham et al. ST6GAL1: A key player in Cancer (Review). Oncol Lett. Aug. 2019; 18(2): 983-989.
"Guinney, et al., The Consensus Molecular subtypes of colorectal cancer. Nat. Med. Nov. 2015; 21(11): 1350-1356.".
Guler et al. Detection of Early Stage Pancreatic Cancer Using 5-Hydroxymethylcytosine Signatures in Circulating Cell Free DNA. Nature Communications 11(1):5270 (Dec. 2020).
Guo et al. Deep multiple instance learning classifies subtissue locations in mass spectrometry images from tissue-level annotations. Bioinformatics, vol. 36, Issue Supplement_1, Jul. 2020, pp. i300-i308.
"Gupta, et al., Recommendations for follow-up after colonoscopy and polypectomy: a consensus update by the US multi-society task force on colorectal cancer. Gastrointest Endosc. Mar. 2020; 91(3): 463-485.".
Hadjidemetriou, et al., A novel scavenging tool for cancer biomarker discovery based on the blood-circulating nanoparticle protein corona. Biomaterials. Jan. 2019; vol. 188: pp. 118-129.
Hamm et al. Frequent expression loss of Inter-alpha-trypsin inhibitor heavy chain (ITIH) genes in multiple human solid tumors: A systematic expression analysis. BMC Cancer, 2008, 8:25.
Hanahan et al. Hallmarks of cancer: the next generation. Cell 144:646-674 (2011).
"Haque, Is et al., Challenges in using ctDNA to achieve early detection of cancer. bioRxiv; Dec. 2017. DOI: 10.1101/237578".
"Hasan, et al., Advances in pancreatic cancer biomarkers. Oncol Rev. Jan. 2019; 13(410): 69-76.".
Havel et al. The evolving landscape of biomarkers for checkpoint inhibitor immunotherapy. Nat Rev Cancer 19(3): 133-150 (2019).
"Haynes, et al., Empowering multi-cohort gene expression analysis to increase reproducibility. Pac Symp Biocomput. 2016; 22: 144-153.".
"Huang, et al., Emerging trends and research foci in gastrointestinal microbiome. J Transl. Med. 2019; 17(67): 1-11.".
"Siegel, et al., Cancer Statistics, 2021. CA: A Cancer Journal for Clinicians. Jan. 2021; vol. 71 Issue 1: 7-33.".
"Silvestri GA, Tanner NT, Kearney P, Vachani A, Massion PP, Porter A, Springmeyer SC, Fang KC, Midthun D, Mazzone PjJ; Panoptic Trial Team. Assessment of Plasma Proteomics Biomarker's Ability to Distinguish Benign From Malignant Lung Nodules: Results of the PANOPTIC (Pulmonary Nodule Plasma Proteomic Classifier) Trial. Chest. Sep. 2018;154(3):491-500. doi: 10.1016/j.chest.2018.02.012. Epub Mar. 1, 2018. PMID: 29496499; PMCID: PMC6689113.".
"John, et al., "Predicting gene expression from plasma cell-free DNA using both the fragment length and fragment position." AACR Annual Meeting; Mar. 29-Apr. 3, 2019.".
Jong et al. Selecting a classification function for class prediction with gene expression data. Bioinformatics, vol. 32, Issue 12, Jun. 15, 2016, pp. 1814-1822.
"Kampf C et al., The human liver-specific proteome defined by transcriptomics and antibody-based profiling. FASEB J. (2014) PubMed: 24648543 DOI: 10.1096/fj.14-250555".
Keshishian, et al., Multiplexed, Quantitative Workflow for Sensitive Biomarker Discovery in Plasma Yields Novel Candidates for Early Myocardial Injury. Mol Cell Proteomics. Sep. 2015;14(9):2375-93. doi: 10.1074/mcp.M114.046813. Epub Feb. 27, 2015.
Keshishian, et al., Quantitative, multiplexed workflow for deep analysis of human blood plasma and biomarker discovery by mass spectrometry. Nat Protoc. Aug. 2017;12(8):1683-1701. doi:10.1038/nprot.2017.054. Epub Jul. 27, 2017.
"Klein, et al., Clinical validation of a targeted methylation-based multi-cancer early detection test using an independent validation set. Annals of Oncology, 2021; vol. 32 Issue 9: 1167-1177.".
Koh, H.M., et al., Prognostic Role of S100A8 and S100A9 Protein expressions in non-small cell carcinoma of the lung. Journal of pathology and translational medicine, 2019; 53:13-22.

"Koizumi, et al., Salivary cytokine panel indicative of non-small cell lung cancer. J Int Med Res. 2018; vol. 46(9): 3570-3582.".
"Li et al., PGAM1, regulated by miR-3614-5p, functions as an oncogene by activating transforming growth factor-B (TGF-B) signaling in the progression of non-small cell lung carcinoma. Cell death and Disease, 2011; 11(710): 1-16.".
Liu et al. High expression of NFAT2 contributes to carboplatin resistance in lung cancer. Experimental and Molecular Pathology, 2019; 110:104290.
Liu, et al., Human plasma N-glycoproteome analysis by immunoaffinity subtraction, hydrazide chemistry, and mass spectrometry. J Proteome Res. Nov.-Dec. 2005;4(6):2070-80. doi: 10.1021/pr0502065.
"Liu, et al., Sensitive and specific multi-cancer detection and localization using methylation signatures in cell-free DNA. Ann Oncol. Jun. 2020; 31(6): 745-759.".
"Liu et al., Spatial co-fragmentation pattern of cell-free DNA recapitulates in vivo chromatin organization and identifies tissues-of-origin. AACR. 2019".
"Lock, et al., Joint and individual variation explained (JIVE) for integrated analysis of multiple data types. Ann Appl Stat. Mar. 1, 2013;7(1):523-542. doi: 10.1214/12-AOAS597.".
"Luz-Crawford et al., Mesenchymal Stem Cell-Derived Interleukin 1 Receptor Antagonist Promotes Macrophage Polarization and Inhibits B Cell Differentiation. Stem Cells. Feb. 2016;34(2):483-92. doi: 10.1002/stem.2254. Epub Dec. 31, 2015. PMID: 26661518.".
Maples, et al., A highly accurate noninvasive multi-omics diagnostic test for nash. DiscernDx, Inc. Nash-Tag conference Abstract Book, Mar. 2021, p. 14.
"Massion P.P. and Walker R.C. Indeterminate pulmonary nodules: Risk for having or for developing lung cancer. Cancer Prev. Res. 2014; 7(12): 1173-1178.".
"Mathios, D., Johansen, U.S., Cristiano, S. et al. Detection and characterization of lung cancer using cell-free DNA fragmentomes. Nat Commun 12, 5060 (2021). https://doi.org/10.1038/s41467-021-24994-w".
McDonald et al. Suspected cancer symptoms and blood test results in primary care before a diagnosis of lung cancer: a case-control study. Future Oncol. (2019) 15(33), 3755-3762.
"McGuigan A, Kelly P, Turkington RC, Jones C, Coleman HG, McCain RS. Pancreatic cancer: A review of clinical diagnosis, epidemiology, treatment and outcomes. World J Gastroenterol. Nov. 21, 2018;24(43):4846-4861. doi: 10.3748/wjg.v24.i43.4846. PMID: 30487695; PMCID: PMC6250924.".
"Meester RG, Doubeni CA, Lansdorp-Vogelaar I, Goede SL, Levin TR, Quinn VP, Ballegooijen Mv, Corley DA, Zauber AG. Colorectal cancer deaths attributable to nonuse of screening in the United States. Ann Epidemiol. Mar. 2015;25(3):208-213.e1. doi: 10.1016/j.annepidem.2014.11.011. Epub Dec. 5, 2014. PMID: 25721748; PMCID: PMC4554530.".
Muller et al. Community-integrated omics links dominance of a microbial generalist to fine-tuned resource usage. Nature Communications vol. 5, Article No. 5603 (2014).
"Murakami M, Naraba H, Tanioka T, Semmyo N, Nakatani Y, Kojima F, Ikeda T, Fueki M, Ueno A, Oh S, Kudo I. Regulation of prostaglandin E2 biosynthesis by inducible membrane-associated prostaglandin E2 synthase that acts in concert with cyclooxygenase-2. J Biol Chem. Oct. 20, 2000;275(42):32783-92. doi: 10.1074/jbc.M003505200. PMID: 10869354.".
"Nakao, et al., Oncological problems in pancreatic cancer surgery. World J Gastroenterol 2006; 12(28): 4466-4472 [PMID: 16874856 DOI: 10.3748/wjg.v12.i28.4466]".
"Song, et al., Diagnostic and prognostic significance of serum apolipoprotein C-I in triple-negative breast cancer based on mass spectrometry. Cancer Biology & Therapy, 2016; 17(6): 635-647.".
Parimon et al. Syndecan-1 Controls Lung Tumorigenesis by Regulating miRNAs Packaged in Exosomes. Am J Pathol. 2018; 188(4): 1094-1103.
PCT/US2021/015339 International Search Report and Written Opinion dated Apr. 13, 2021.

(56) References Cited

OTHER PUBLICATIONS

"Pereira, S. P., Oldfield, L., Ney, A., Hart, P. A., Keane, M. G., Pandol, S. J., Li, D., Greenhalf, W., Jeon, C. Y., Koay, E. J., Almario, C. V., Halloran, C., Lennon, A. M., & Costello, E. (2020). Early detection of pancreatic cancer. The lancet. Gastroenterology & hepatology, 5(7), 698-710. https://doi.org/10.1016/S2468-1253(19)30416-9".

Polasky, et al., Fast and comprehensive N- and O-glycoproteomics analysis with MSFragger-Glyco. Nat Methods. Nov. 2020;17(11):1125-1132. doi: 10.1038/s41592-020-0967-9. Epub Oct. 5, 2020.

"Qu WQ, Liu L, Yu Z. Clinical value of microRNA-23a upregulation in non-small cell lung cancer. Int J Clin Exp Med. Aug. 15, 2015;8(8):13598-603. PMID: 26550300; PMCID: PMC4612985.".

"Ramos-Esquivel et al., Anti-PD-1/anti-PD-L1 immunotherapy versus docetaxel for previously treated advanced non-small cell lung cancer: a systematic review and meta-analysis of randomised clinical trials. ESMO Open 2017;2:e000236. doi:10.1136/esmoopen-2017-000236".

"Robinson, et al., A Systematic Investigation of the Malignant Functions and Diagnostic Potential of the Cancer Secretome. Cell Rep. Mar. 5, 2019; 26(10):2622-2635.e5. doi: 10.1016/j.celrep.2019.02.025.".

Roushan, et al., Peak Filtering, Peak Annotation, and Wildcard Search for Glycoproteomics. Mol Cell Proteomics. 2021;20:100011. doi: 10.1074/mcp.RA120.002260. Epub Dec. 8, 2020.

Roy et al. Multiomics data collection visualization and utilization for guiding metabolic engineering. Frontiers in bioengineering and biotechnology, 2021,9, Article 612983.

"Ruan H., Hu S., Zhang H., Du G., Li X., Li X., Li X. Upregulated SOX9 expression indicates worse prognosis in solid tumors: a systematic review and meta-analysis. Oncotarget. 2017; 8: 113163-113173. Retrieved from https://www.oncotarget.com/article/22635/text/".

Skyarysz, A., Alkhalifah, Y., Darnley, K., Eddleston, M., McLaren, D., Nailon, W. H., Salman, D., Sykora, M., Thomas, P., & Soltoggio, A. (2018). Convolutional neural networks for automated targeted analysis of raw gas chromatography-mass spectrometry data. In Proceedings of theInternational Joint Conference on Neural Networks (IJCNN 2018)At: Rio de Janeiro, Brazil https://doi.org/10.1109/IJCNN.2018.8489539.

"St. John et al., Predicting gene expression from plasma cell-free DNA using both the fragment length and fragment position. AACR. 2019.".

Telenti, A. et al. Deep sequencing of 10,000 human genomes. Proc. Natl. Acad. Sci. USA 113(42):11901-11906 (Oct. 18, 2016).

Tenzer, S., et al. Nanoparticle size is a critical physicochemical determinant of the human blood plasma corona: a comprehensive quantitative proteomic analysis. ACS Nano 5, 7155-7167 (2011).

"The 1000 Genomes Project Consortium. A global reference for human genetic variation. Nature 526, 68-74 (2015). https://doi.org/10.1038/nature15393".

"Uhlen, M. et al., A Pathology atlas of the human cancer transcriptome. Science. 2017. PubMed: 28818916 DOI: 10.1126/science.aan2507".

"Voronov, Elena et al. "Unique Versus Redundant Functions of IL-1α and IL-1β in the Tumor Microenvironment." Frontiers in immunology vol. 4 177. Jul. 8, 2013, doi:10.3389/fimmu.2013.00177".

Wang et al. MOGONET integrates multi-omics data using graph convolutional networks allowing patient classification and biomarker identification. Nature Communications, 2021; 12:3445.

Weinstein, et al. The cancer genome atlas pan-cancer analysis project. Nature genetics 45.10 (2013): 1113-1120.

"White A, Thompson TD, White MC, et al. Cancer Screening Test Use—United States, 2015. MMWR Morb Mortal Wkly Rep Mar. 2017;66(8):201-206. DOI: http://dx.doi.org/10.15585/mmwr.mm6608a1".

Xu et al. Calpain-2 Enhances non-small cell lung cancer progresion and Chemoresistance to paclitaxel via EGFR-pAKT pathway. Int J Biol Sci. 2019; 15(1): 127-137.

"Yigit M, Değirmencioglu S, Ugurlu E, Yaren A. Effect of serum interleukin-1 receptor antagonist level on survival of patients with non-small cell lung cancer. Mol Clin Oncol. May 2017;6(5):708-712. doi: 10.3892/mco.2017.1195. Epub Mar. 15, 2017. PMID: 28515924; PMCID: PMC5431311.".

Yoon et al. NOTUM Is Involved in the Progression of Colorectal Cancer Cancer Genomics & Proteomics, 2018; 15:485-497.

Yu et al. Prognostic and clinicopathological significance of Cacna2d1 expression in epithelial ovarian cancers: a retrospective study. Am J Cancer Res 2016;6(9):2088-2097.

Yuan et al. Modification of α2, 6-sialylation mediates the invasiveness and tumorigenicity of non-small cell lung cancer cells in vitro and in vivo via Notch 1/Hes1/MMPs pathway. Int J Cancer. 2018; 143(9):2319-2330.

Zhang et al. Identification of Apolipoprotein C-I as a Potential Wilms' Tumor Marker after Excluding inflammatory factors. Int. J. Mol. Sci. 2014, 15(9), 16186-16195.

Zhang et al. SMC4, which is essentially involved in lung development, is associated with lung adenocarcinoma progression. Scientific Reports, 2016, 6:34508.

"Zhang L, Zheng J, Ahmed R, Huang G, Reid J, Mandal R, Maksymuik A, Sitar DS, Tappia PS, Ramjiawan B, Joubert P, Russo A, Rolfo CD, Wishart DS. A High-Performing Plasma Metabolite Panel for Early-Stage Lung Cancer Detection. Cancers (Basel). Mar. 7, 2020;12(3):622. doi: 10.3390/cancers12030622. PMID: 32156060; PMCID: PMC7139410.".

"Zhang S., Che D., Yang F., Chi C., Meng H., Shen J., Qi L., Liu F., Lv L., Li Y., Meng Q., Liu J., Shang L., et al. Tumor-associated macrophages promote tumor metastasis via the TGF-β/SOX9 axis in non-small cell lung cancer. Oncotarget. 2017; 8: 99801-99815. Retrieved from https://www.oncotarget.com/article/21068/text/".

Andreeva, A.V., and Kutuzov, M.A. Cadherin 13 in cancer. Genes Chromosomes Cancer, 2010, 49(9):775-90.

Bludau, I., Aebersold, R. Proteomic and interactomic insights into the molecular basis of cell functional diversity. Nat Rev Mol Cell Biol 2020;21: 327-340. https://doi.org/10.1038/s41580-020-0231-2.

Capriotti et al.: Analytical methods for characterizing the nanoparticle-protein corona. Chromatographia 77(11-12):755-769 DOI:10.1007/s10337-014-2677-x (2014).

"Chantada-Vazquez, et al., Proteomic analysis of the bio-corona formed on the surface of (Au, Ag, Pt)-nanoparticles in human serum. Colloids Surf B Biointerfaces. May 1, 2019 ;177:141-148. doi: 10.1016/j.colsurfb.2019.01.056. Epub Jan. 29, 2019. PMID: 30721790.".

"Chantada-Vazquez et al., Proteomic investigation on bio-corona of Au, Ag and Fe nanoparticles for the discovery of triple negative breast cancer serum protein biomarkers. J Proteomics. Feb. 10, 2020;212:103581. doi: 10.1016/j.jprot.2019.103581. Epub Nov. 12, 2019. PMID: 31731051.".

Chen, et al., Glycoproteomics analysis of human liver tissue by combination of multiple enzyme digestion and hydrazide chemistry. J Proteome Res. Feb. 2009;8(2):651-61. doi: 10.1021/pr8008012.

Chen, T., Kornblith, S., Norouzi, M. et al. A Simple Framework for Contrastive Learning of Visual Representations. Proceedings of the 37 th International Conference on Machine Learning, Vienna, Austria, PMLR 119, 2020.

Cohen, et al., Detection and localization of surgically resectable cancers with a multi-analyte blood test. Science Feb. 23, 2018: vol. 359, Issue 6378, pp. 926-930. DOI: 10.1126/science.aar3247.

Co-pending U.S. Appl. No. 17/930,663, inventors Liu; Manway et al., filed Sep. 8, 2022.

Co-pending U.S. Appl. No. 17/931,469, inventors Wilcox; Bruce et al., filed Sep. 12, 2022.

"Corbo, et al., Analysis of the Human Plasma Proteome Using Multi-Nanoparticle Protein Corona for Detection of Alzheimer's Disease. Adv. Healthcare Mater. 2021, 10, 2000948. https://doi.org/10.1002/adhm.202000948".

Cox, et al., MaxQuant enables high peptide identification rates, individualized p.p.b.-range mass accuracies and proteome-wide protein quantification. Nat Biotechnol. Dec. 2008;26(12):1367-72. doi: 10.1038/nbt.1511. Epub Nov. 30, 2008.

(56) References Cited

OTHER PUBLICATIONS

Datta, S. et al., Statistical Analysis of Proteomics, Metabolomics, and Lipidomics Data Using Mass Spectrometry. Springer Cham, 2017; 295 Pages.
Haug U, Knudsen AB, Lansdorp-Vogelaar I, Kuntz KM. Development of new non-invasive tests for colorectal cancer screening: the relevance of information on adenoma detection. Int J Cancer. Jun. 15, 2015;136(12):2864-74. doi: 10.1002/ijc.29343. Epub Dec. 3, 2014. PMID: 25403937; PMCID: PMC4397119.
"Heitzer, E. et al., Current and future perspectives of liquid biopsies in genomics-driven oncology. Nat Rev Genet 20, 71-88 (2019). https://doi.org/10.1038/s41576-018-0071-5".
"Imperiale, et al., Multitarget stool DNA testing for colorectal-cancer screening. N Engl J Med. Apr. 2014;370:1287-1297.".
Jensen, M., and Berthold, F. Targeting the neural cell adhesion molecule in cancer. Cancer Lett., Dec. 2007., 258(1):9-21.
Lu, et al., The crucial role of multiomic approach in cancer research and clinically relevant outcomes. EPMA Journal (2018) 9; 77-102: https://doi.org/10.1007/s13167-018-0128-8.
Lu, J., and Gu, J. Significance of β-Galactoside α2,6 Sialyltranferase 1 in Cancers. Molecules, 2015, 20, 7509-7527.
Ludwig C, Gillet L, Rosenberger G, Amon S, Collins BC, Aebersold R. Data-independent acquisition-based SWATH-MS for quantitative proteomics: a tutorial. Mol Syst Biol. Aug. 13, 2018;14(8):e8126. doi: 10.15252/msb.20178126. PMID: 30104418; PMCID: PMC6088389.
"Mazzaschi G, Facchinetti F, Missale G, Canetti D, Madeddu D, Zecca A, Veneziani M, Gelsomino F, Goldoni M, Buti S, Bordi P, Aversa F, Ardizzoni A, Quaini F, Tiseo M. The circulating pool of functionally competent NK and CD8+ cells predicts the outcome of anti-PD1 treatment in advanced NSCLC. Lung Cancer. Jan. 2019;127:153-163. doi: 10.1016/j.lungcan.2018.11.038. Epub Nov. 29, 2018. PMID: 30642544.".
Pirinen et al. Versican in nonsmall cell lung cancer: Relation to hyaluronan, clinicopathologic factors, and prognosis. Human Pathology, 2004; 36(1):44-50.
Ponzi, et al., Integrative, multi-omics, analysis of blood samples improves model predictions: applications to cance. BMC Bioinformatics, 2021; 22:395 https://doi.org/10.1186/s12859-021-04296-0.
"Putcha, et al., Blood-based detection of early-stage colorectal cancer using multiomics and machine learning. Journal of clinical oncology, 2020; 38(4): 66.".
"Reel PS, Reel S, Pearson E, Trucco E, Jefferson E. Using machine learning approaches for multi-omics data analysis: A review. Biotechnol Adv. Jul.-Aug. 2021;49:107739. doi: 10.1016/j.biotechadv.2021. 107739. Epub Mar. 29, 2021. PMID: 33794304.".
Rubio, et al., Multi-omic analysis unveilsvbiological pathways in peripheral immune system associated to minimal hepatic encephalopathy appearance in cirrhotic patients. Scientific Reports, 2021; 11:1907.https://doi.org/10.1038/s41598-020-80941-7.
Stelzer, et al., The GeneCards Suite: From Gene Data Mining to Disease Genome Sequence Analyses. Curr Protoc Bioinformatics. Jun. 20, 2016;54:1.30.1-1.30.33. doi: 10.1002/cpbi.5.
Ulz, et al., Inference of transcription factor binding from cellfree DNA enables tumor subtype prediction and early detection. Nature Communications, (2019) 10:4666; https://doi.org/10.1038/s41467-019-12714-4, www.nature.com/naturecommunications.
Wainberg, et al., Multiomic blood correlates of genetic risk identify presymptomatic disease alterations. PNAS, Sep. 2020; vol. 117, No. 35: 21813-21820.
Wan, et al., Machine learning enables detection of early-stage colorectal cancer by whole-genome sequencing of plasma cell-free DNA. BMC Cancer (2019) 19:832 https://doi.org/10.1186/S12885-019-6003-8.
Zhang et al., Deep Learning-Based Multi-Omics Data Integration Reveals Two Prognostic Subtypes in High-Risk Neuroblastoma. Front. Genet., Oct. 18, 2018 https://doi.org/10.3389/fgene.2018. 00477.
Zhang, et al., Phenotype Prediction using a Tensor Representation and Deep Learning from Data Independent Acquisition Mass Spectrometry. bioRxiv 2020.03.05.978635; doi: https://doi.org/10.1101/2020.03.05.978635.
Zhu et al., Apolipoprotein M promotes proliferation and invasion in non-small cell lung cancers via upregulating S1PR1 and activating the ERK1/2 and PI3K/AKT signaling pathways. Biochemical and Biophysical Research Communications, 2018, 501(2):520-526.
GB2205544.6 Examination Report dated Jun. 14, 2022.
Demichev et al.: DIA-NN: neural networks and interference correction enable deep proteome coverage in high throughput. Nature Methods 17(1):41-44 DOI:10.1038/S41592-019-0638 (2020).
Gunther, O.P. et al. A computational pipeline for the development of multi-marker bio-signature panels and ensemble classifiers. BMC Bioinformatics 13,326 (2012), p. 1-17. (Year: 2012).
Kim, et al., A chemical with proven clinical safety rescues down-syndrome-related phenotypes in through DYRK1A inhibition. Disease Models & Mechanisms (2016) 9, 839-848.
Li, L. et al.; "Data mining techniques for cancer detection using serum proteomic profiling", Artificial Intelligence in Medicine, vol. 32, Issue 2, 2004, pp. 71-83 (Year: 2004).
Lin, E., Lane, HY. "Machine learning and systems genomics approaches for multi-omics data." Biomark Res 5, 2 (2017), p. 1-6 (Year: 2017).
Ocana, A., Pandiella, A. "Personalized therapies in the cancer omics era", Mol Cancer 9, 202 (2010), p. 1-12. (Year: 2010).
PCT/US2022/022654 International Search Report and Written Opinion dated Aug. 15, 2022.
U.S. Appl. No. 17/709,185 Office Action dated Sep. 15, 2022.
U.S. Appl. No. 17/720,197 Office Action dated Oct. 14, 2022.
Agajanian, et al., Integration of Random forest classifiers and deep convolutional neural networks for classification and Biomolecular modeling of cancer driver mutations. Frontiers in molecular biosciences 6 (2019): 44. Jun. 11, 2019, Retrieved on Oct. 30, 2022. From https://www.frontiersin.org/articles/10.3389/fmolb.2019.00044/full entire document.
Bakry et al. Protein profiling for cancer biomarker discovery using matrix-assisted laser desorption/ionization time-of-flight mass spectrometry and infrared imaging: A review. Analytica Chimica Acta 2011, vol. 690, pp. 26-34 (Year: 2011).
Bronsema, K. J. et al.; "Internal standards in the quantitative determination of protein biopharmaceuticals using liquidchromatography coupled to mass spectrometry", Journal of Chromatography B, vols. 893-894, 2012, pp. 1-14. (Year: 2012).
Cohen, et al., Combined circulating tumor DNA and protein biomarker-based liquid biopsy for the earlier detection of pancreatic cancers. PNAS, Sep. 5, 2017; 114 (38) 10202-10207, https://doi.org/10.1073/pnas.1704961114.
Co-pending U.S. Appl. No. 18/095,422, inventors Wilcox; Bruce et al., filed Jan. 10, 2023.
Co-pending U.S. Appl. No. 18/150,390, inventors Ma; Philip et al., filed Jan. 5, 2023.
Co-pending U.S. Appl. No. 18/164,446, inventors Ma; Philip et al., filed Feb. 3, 2023.
Co-pending U.S. Appl. No. 18/165,264, inventor Manway; Liu, filed Feb. 6, 2023.
Correia, et al., Machine learning modeling of blood lipid biomarkers in familial hypercholesterolaemia versus polygenic/environmental dyslipidaemia. Nature portfolio, Scientific Reports (2021) 11:3801; 9 Pages.
Grossi et al. Prognostic role of the VeriStrate test in first line patients with non-small cell lung cancer treated with platinum-based chemotherapy. Lung Cancer 2018, vol. 117, pp. 64-69 (Year: 2018).
Hasin, Yehudit, Marcus Seldin, and Aldons Lusis. "Multi-omics approaches to disease." Genome biology 18.1 (2017): 1-15. (Year:2017).
Havlis, Jan, and Andrej Shevchenko. "Absolute quantification of proteins in solutions and in polyacrylamide gels by massspectrometry." Analytical chemistry 76.11 (2004): 3029-3036. (Year: 2004).
Jiang et al. "Surface-Enhanced Raman Nanoprobes with Embedded Standards for Quantitative Cholesterol Detection" small methods, vol. 2 Issue 11 (Nov. 13, 2018): pp. 1-14; entire document.

(56) References Cited

OTHER PUBLICATIONS

Katzke, et al., Blood lipids and lipoproteins in relation to incidence and mortality risks for CVD and cancer in the prospective EPIC-Heidelberg cohort, BMC Medicine (2017) 15:218; 13 Pages.
Khlebtsov et al. "Gap-enhanced Raman tags: fabrication, optical properties, and theranostic' applications" Theranostics, vol. 10 Issue 5 (2020): pp. 2067-2094; entire document.
Leal et al. Prognostic performance of proteomic testing in advanced non-small cell lung cancer: a systematic literature review and meta-analysis. Current Medical Research and Opinion 2020, vol. 36, No. 9, pp. 1497-1505 (Year: 2020).
Lee et al. The clinical role of VeriStrat testing in patients with advanced non-small cell lung cancer considered unfit for first-line platinum-based chemotherapy. European Journal of Cancer 2019, vol. 120, pp. 86-96 (Year: 2019).
Lemjabbar-Alaoui et al. Lung Cancer: Biology and Treatment options. Biochimica et Biophysica Acta 2015, 1856, pp. 189-210 (Year: 2015).
Liu, et al., Machine Learning Protocols in Early Cancer Detection Based on Liquid Biopsy: A Survey. Life 2021, 11,638,39 Pages, https://doi.org/ 10.3390/life11070638.
Nguyen, et al., Protein corona: a new approach for nanomedicine design, International Journal of Nanomedicine 2017:12; 3137-3151.
PCT/US2022/076125 International Search Report and Written Opinion dated Jan. 12, 2023.
PCT/US2022/076297 International Search Report and Written Opinion dated Nov. 30, 2022.
Qian et al. Screening for early stage lung cancer and its correlation with lung nodule detection. J Thorac Dis 2018, 1 0(Suppl 7): S846-859 (Year: 2018).
Ritz, et al.,, Protein Corona of Nanoparticles: Distinct Proteins Regulate the Cellular Uptake, Biomacromolecules 2015:16(4); 1311-1321 DOI: 10.1021/acs.biomac.5b00108.
Song, M. et al.; "A Review of Integrative Imputation for Multi-Omics Datasets" Front. Genet. vol. 11, article 570255, Oct. 15, 2020, p. 1-15 (Year: 2020).
Trivedi et al. Risk assessment for indeterminate pulmonary nodules using a novel, plasma-protein based biomarker assay. Biomed Res Clin Pract 2018, 3(4), pp. 1-17 (Year: 2018).
Unger, Klaus K., et al. "Liquid chromatography—its development and key role in life science applications." Angewandte ChemieInternational Edition 49.13 (2010): 2300-2312 (Year: 2010).
U.S. Appl. No. 17/709,185 Office Action dated Dec. 7, 2022.
U.S. Appl. No. 17/709,202 Office Action dated Jan. 26, 2023.
U.S. Appl. No. 17/709,202 Office Action dated Nov. 23, 2022.
U.S. Appl. No. 17/720,197 Office Action dated Jan. 5, 2023.
U.S. Appl. No. 17/931,469 Office Action dated Dec. 28, 2022.
Yuan et al. "Antimicrobial peptide based magnetic recognition elements and Au@Ag-GO SERS tags with stable internal standards: a three in one biosensor for isolation, discrimination andkilling of multiple bacteria in whole blood" Chemical Science, vol. 9 (Nov. 2, 2018): pp. 8781-8795; entire document.
Zhang et al., Phenotype Classification using Proteome Data in a Data-independent Acquisition Tensor Format. J Am Soc Mass Spectrom. Nov. 4, 2020;31(11):2296-2304. doi: 10.1021/jasms. 0c00254. Epub Oct. 26, 2020. PMID: 33104352.
Li, Xiao-jun et al., A Blood-Based Proteomic Classifier for the Molecular Characterization of Pulmonary Nodules. Sci Transl Med. Oct. 16, 2013; 5(207): 207ra142. doi:10.1126/scitranslmed. 3007013.
Pearson, Ryan M., Vanessa V. Juettner, and Seungpyo Hong. "Biomolecular corona on nanoparticles: a survey of recent literature and its implications in targeted drug delivery." Frontiers in chemistry 2 (2014): 108.
U.S. Appl. No. 17/709,185 Office Action dated Mar. 16, 2023.
Walkey et al. ("Protein Corona Fingerprinting Predicts the Cellular Interaction of Gold and Silver Nanoparticles," ACS NANO, vol. 8, No. 3, pp. 2439-2455, published 2014) (Year: 2014).
Wan et al. ("Highly Specific Electrochemical Analysis of Cancer Cells using Multi-Nanoparticle Labeling," Angew. Chem. Int. Ed. 2014, vol. 53, pp. 13145-13149) (Year: 2014).
Kuang, M. et al., Proteomic analysis of plasma exosomes to differentiate malignant from benign pulmonary nodules. Clin Proteom 16, 5 (2019). https://doi.org/10.1186/s12014-019-9225-5.
"SEER, Inc. Form 10-Q For Quarterly period ended Jun. 30, 2021." EDGAR. Securities and Exchange Commission, 2021, https://www.sec.gov/ix?doc=/Archives/edgar/data/0001726445/000162828021016865/seer-20210630.htm.
U.S. Appl. No. 17/931,469 Office Action dated Apr. 3, 2023.

\* cited by examiner

Sample iteration AUC 0.53 ± 0.03

| Protein | Function | Linkage to cancer |
|---|---|---|
| ANGPTL6 | Secreted glycoprotein, involved in angiogenesis | • Globlastoma<br>• Colorectal cancer<br>• Gastric cancer |
| ANTXR2 | Secreted cell adhesion molecular involved in capillary morphogenesis | • Gliomas<br>• Gastric cancer<br>• Head and neck cancers |
| CCL18 | Secreted protein involved in chemotactic responses and immune function | Involved in tumor microenvironment for multiple cancers, including breast, bladder, pancreas, lung and oral cancers |
| HTRA1 | Secreted protein, involved in regulation of TGF-beta signaling, apoptosis, and EGFR/AKT pathway | Involved in mediating anti-tumor efficacy, including correlation of over-expression with cisplatin-resistance in NSCLC |
| TUBA1A | Structural protein and component of tubulin, the major constituent of microtubules | Drug target for cancer drugs paclitaxel and vinflunine |

FIG. 15

LUNG BIOMARKERS AND METHODS OF USE THEREOF

CROSS-REFERENCE

This application is a continuation of International Patent Application No. PCT/US2021/015339 filed Jan. 27, 2021, which claims the benefit of U.S. Provisional Application No. 62/967,995 filed Jan. 30, 2020, each of which is incorporated herein by reference in its entirety.

BACKGROUND

Early detection of NSCLC is key to a favorable prognosis, but there has been little progress in the development of useful clinical tests. Proteins in plasma should be a valuable biomarker discovery matrix given plasma's contact with almost all tissues in the body. However, plasma proteins can be problematic due to several factors including a wide range of concentration (e.g., 10-orders of magnitude). Complex biochemical workflows have attempted to circumvent these challenges but may not be practical for discovery studies of sufficient size to ensure validation and replication. Alternatively, biomarker studies have been limited to evaluating or re-evaluating known markers without substantive improvement in clinical performance.

SUMMARY

Disclosed herein are systems and methods for analyzing protein-particle interactions and protein-protein interactions. Interactions between biological molecules and particles and protein-protein interactions on particles may provide insights on protein-protein interactions across biological samples.

In various aspects, the present disclosure provides a method comprising: obtaining a data set comprising protein information from biomolecule coronas that correspond to physicochemically distinct particles incubated with a biofluid sample from a subject; and using a classifier to identify the biofluid sample being indicative of a healthy state, a cancer state, or a comorbidity thereof in the subject, based on the data set.

In some aspects, the cancer is non-small cell lung cancer (NSCLC) and the comorbidity is a pulmonary comorbidity. In some aspects, the pulmonary comorbidity is a chronic lung disease other than non-small cell lung cancer. In some aspects, the pulmonary comorbidity is selected from the group consisting of: chronic obstructive pulmonary disease (COPD), emphysema, cardiovascular disease, hypertension, pulmonary fibrosis, asthma, a chronic lung disease, and any combination thereof. In some aspects, the cancer state is identified with a sensitivity or specificity of about 80% or greater.

In some aspects, the protein information comprises expression information for a protein selected from the group consisting of: Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some aspects, the protein information comprises expression information for a protein selected from the group consisting of: ANGL6, HTRA1, PXDN, ANTR2, CSPG2, ANTR1, NOTUM, CILP1, CAN2, and GP1BB.

In some aspects, obtaining a data set comprises contacting the biofluid sample with the physicochemically distinct particles to form the biomolecule coronas. In some aspects, the physicochemically distinct particles comprise lipid particles, metal particles, silica particles, or polymer particles. In some aspects, the physicochemically distinct particles comprise carboxylate particles, poly acrylic acid particles, dextran particles, polystyrene particles, dimethylamine particles, amino particles, silica particles, or N-(3-trimethoxysilylpropyl)diethylenetriamine particles.

In some aspects, obtaining a data set comprises detecting proteins of the biomolecule coronas by mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. In some aspects, obtaining a data set comprises detecting the proteins of the biomolecule coronas by mass spectrometry. In some aspects, obtaining a data set comprises measuring a readout indicative of the presence, absence or amount of proteins of the biomolecule coronas.

In some aspects, the classifier is generated by removing or filtering out biomolecules associated with acute phase response. In some aspects, the NSCLC comprises early stage NSCLC (stage 1, stage 2, or stage 3). In some aspects, the NSCLC comprises late stage NSCLC (stage 4). In some aspects, the method further comprises administering a NSCLC treatment to the subject based on the disease state. In some aspects, the classifier has an increased protein detection consistency relative to a second classifier generated using proteomic data from depleted plasma samples.

In some aspects, the biofluid comprises a blood sample that has had red blood cells removed. In some aspects, the biofluid comprises plasma.

In various aspects, the present disclosure provides a method of evaluating a status of a cancer, comprises: measuring biomarkers in a biofluid sample from a subject suspected of having the cancer to obtain biomarker measurements, wherein the biomarkers comprise one or more biomarkers selected from the group consisting of: Angiopoietin-related protein 6 (ANGL6), Serine protease HTRA1 (HTRA1), Peroxidasin homolog (PXDN), Anthrax toxin receptor 2 (ANTR2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), Platelet glycoprotein Ib beta chain (GP1BB).

In some aspects, measuring the one or more biomarkers comprises using a detection reagent that binds to a protein and yields a detectable signal. In some aspects, measuring the one or more biomarkers comprises measuring a readout indicative of the presence, absence or amounts of the one or more biomarkers. In some aspects, measuring the biomarkers comprises performing mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. In some aspects, measuring the biomarkers comprises performing mass spectrometry. In some aspects, measuring the biomarkers comprises performing an immunoassay. In some aspects, measuring the biomarkers comprises contacting the biofluid sample with a plurality of physicochemically distinct nanoparticles.

In some aspects, the cancer comprises lung cancer. In some aspects, the method further comprises applying a classifier to the biomarker measurements. In some aspects, the classifier distinguishes the cancer from a chronic lung disorder, chronic obstructive pulmonary disease, emphysema, cardiovascular disease, hypertension, pulmonary fibrosis, or asthma.

In some aspects, the cancer comprises non-small cell lung cancer (NSCLC). In some aspects, the NSCLC comprises early stage NSCLC (stage 1, stage 2, or stage 3). In some aspects, the method further comprises applying a classifier to the biomarker measurements, wherein the classifier comprises features to distinguish between early stage NSCLC and late stage NSCLC. In some aspects, the features comprise one of more biomarkers selected from the group consisting of: SDC1, OC085, KV401, MYL6, JIP2, HV459, HV461, HV169, HNRPC, ROA1, STON2, LV301, KVD20, SAE1, PDE5A, RTN3, HV373, LV325, H2B1C, H2B1D, H2B1H, H2B1K, H2B1L, H2B1M, H2B1N, H2B2F, H2BFS, and NMT1. In some aspects, the method further comprises applying a classifier to the biomarker measurements, wherein the classifier comprises features to distinguish between the presence or absence of NSCLC. In some aspects, the features comprise one of more biomarkers selected from the group consisting of: SDC1, ANGL6, PXDN, ANTR1, OC085, SAA2, HTRA1, KPCB, KV401, OCL18, MYL6, ANTR2, GTPB2, HDGF, TBA1A, CSRP1, TCO2, CSPG2, PTPRZ, ILF2, SIAT1, ITA2B, DOK2, H31, H31T, H32, H33, H3C, RAC2, ARRB1, DHB4, HV102, RHG18, GDF15, PCSK6, FHOD1, OR ITLN2.

In some aspects, the method further comprises identifying the subject as having the cancer based on the biomarker measurements. In some aspects, the method further comprises administering a cancer treatment to the subject.

In some aspects, the biofluid comprises a blood sample that has had red blood cells removed, or comprises plasma. In some aspects, the subject is human.

In various aspects, the present disclosure provides a method, comprising: (a) assaying a biological sample from a subject to identify biomolecules; (b) using a classifier (e.g. a trained classifier) to identify that said sample or said subject is positive or negative for non-small cell lung cancer based on said biomolecules identified in (a), wherein said trained classifier is trained using data from training samples comprising known healthy samples and known non-small cell lung cancer samples, and wherein said training samples were assayed using a plurality of particles having physicochemically distinct properties to yield said data.

In some aspects, said biomolecules comprise proteins. In some aspects, said biomolecules are proteins. In some aspects, said data comprises proteomic data identifying a presence or an absence of proteins in said training samples. In some aspects, said trained classifier is configured to remove acute-phase-response bias or stress protein bias. In some aspects, said trained classifier comprises features that relate to proteins, wherein said features are selected to exclude acute-phase response and/or stress protein bias in said biological sample.

In some aspects, said features of said classifier exclude a protein selected from the group consisting of: C-Reactive Protein (CRP), haptoglobin, and S10a8/9. In some aspects, said features of said classifier exclude CRP, haptoglobin, and S10a8/9. In some aspects, said features of said classifier exclude proteins listed in TABLE 5. In some aspects, said features of said classifier comprise a plurality of proteins listed in TABLE 7. In some aspects, said features of said classifier are listed in TABLE 7. In some aspects, said features comprise tubulin alpha-1A chain (TBA1A) and syndecan-1 (SDC1).

In some aspects, the method further comprises obtaining a biological sample from a subject. In some aspects, said biological sample is a complex biological sample. In some aspects, said complex biological sample is a plasma sample or a serum sample. In some aspects, said plurality of particles having physicochemically distinct properties comprise two or more particles listed in TABLE 4. In some aspects, said plurality of particles having physicochemically distinct properties are listed in TABLE 4. In some aspects, said trained classifier has improved performance, based on area under curve (AUC), relative to a classifier that is trained using proteomic data from depleted plasma samples from the same subjects as said known healthy samples and said known non-small cell lung cancer samples.

In some aspects, the methods further comprise outputting a report indicating that said sample or said subject is positive or negative for said non-small cell lung cancer. In some aspects, said assaying comprises performing mass spectrometry or ELISA, and wherein said biomolecules comprise protein. In some aspects, said assaying comprises targeted mass spectrometry. In some aspects, said trained classifier is a trained algorithm. In some aspects, said known non-small cell lung cancer samples comprise early stage (stages 1-3) non-small cell lung cancer samples. In some aspects, said trained classifier identifies that said sample or said subject is positive for said non-small cell lung cancer and a stage of said non-small cell lung cancer.

In some aspects, the method further comprises identifying that said sample or said subject is positive or negative for non-small cell lung cancer with a sensitivity of greater than about 80%. In some aspects, the sensitivity is greater than about 85%, about 90%, about 95%, or about 99%. In some aspects, the method further comprises identifying that said sample or said subject is positive or negative for non-small cell lung cancer with a specificity of greater than about 80%. In some aspects, the specificity is greater than about 85%, about 90%, about 95%, or about 99%.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 15 shows examples of biomarkers.

DETAILED DESCRIPTION

Figure 1:
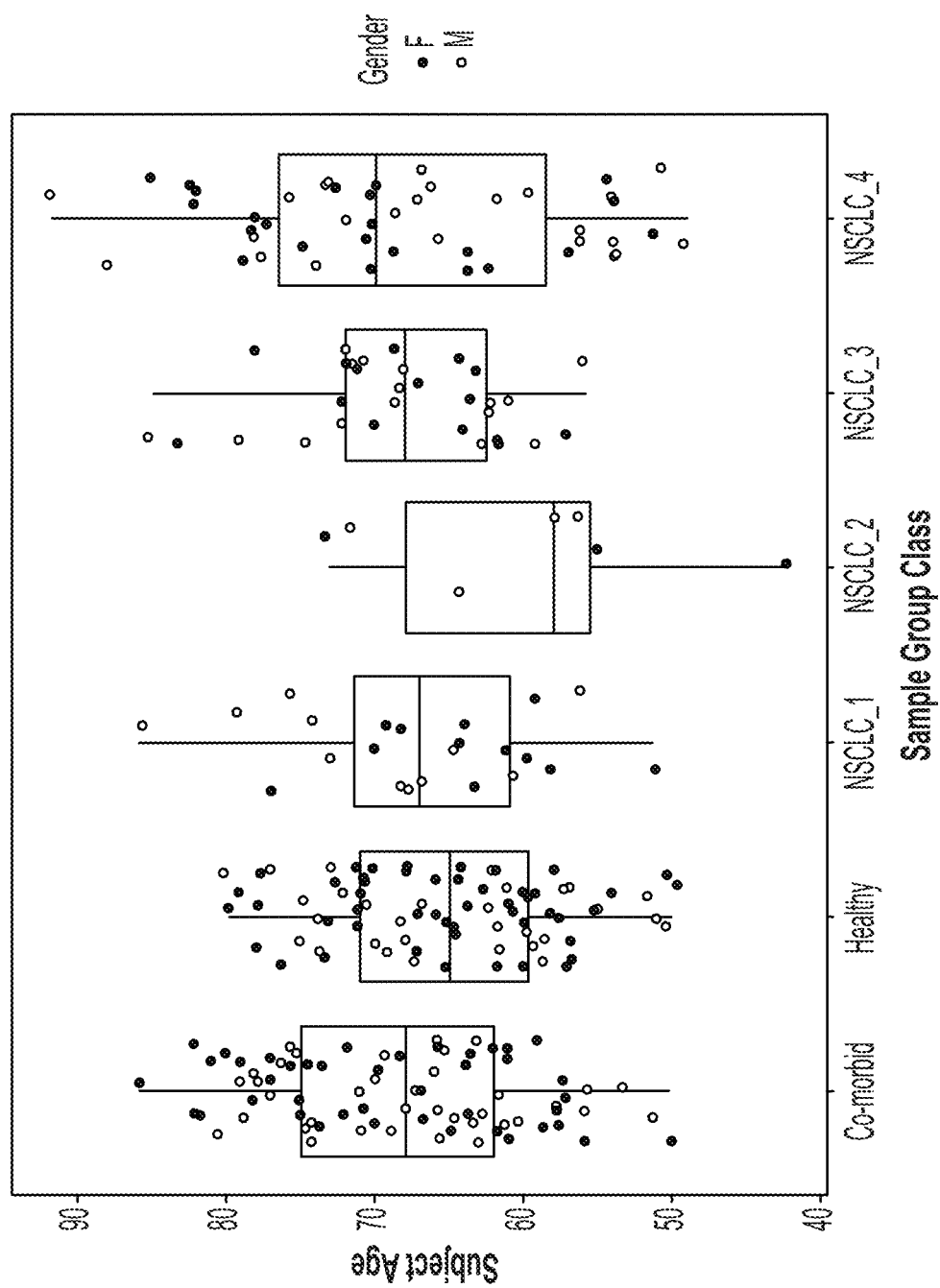
FIG. 1 shows the age and gender breakout for the 268 subjects in the NSCLC biomarker discovery study.

Disclosed herein are compositions and methods of identifying high-performance, protein-based classifiers for healthy versus non-small cell lung carcinoma (NSCLC) based on deep plasma protein profiling with a novel multi-particle type panel platform. The compositions and methods disclosed herein achieve superior protein-based NSCLC biomarker discovering using a novel proteomics profiling platform of panels of particle types disclosed herein for quantification of plasma proteins. Particles (e.g., nanoparticles) may specifically and reproducibly interrogate subsets of protein from biofluids, and have high efficiency and effectiveness for proteomics profiling. The low-complexity particle panel workflow disclosed herein enables studies of a size such as described herein and larger. By profiling NSCLC subjects against healthy and pulmonary co-morbidity control subjects, particle-based platforms were used to identify multi-protein classification panels. These classifiers include previously unknown proteins that play a role in NSCLC. Thus, particle panels disclosed herein were capable of identifying new markers for improved early disease detection.

In one trial, a particle panel disclosed herein identified 1,779 proteins in 288 subjects in 7 weeks, a throughput enabled by the simplicity and robustness of the particle platform. The performance of the healthy versus early NSCLC (Stages 1, 2, and 3) classifier (AUC 0.90), included proteins known and unknown to play a role in NSCLC. Thus, the proteins disclosed herein enable better assays for early disease detection. This marks the first time that a deep plasma protein biomarker profiling study has achieved a throughput that matches genomics-based studies and enables complementary studies including protein and nucleic-acid.

The present disclosure also provides methods of using trained classifiers for classifying a sample as healthy, co-morbid, or NSCLC by training said classifiers with the biomarkers discovered to be associated with NSCLC and which sensitively and specifically distinguish NSCLC from healthy and co-morbid states.

The biomarkers disclosed herein were discovered using particle panels having one or more different particle types, which were subsequently incubated with samples to form biomolecule coronas on the surface of said particles, and assayed for proteins in the biomolecule coronas. Particle panels can have multiple distinct particle types, which enrich proteins from a sample onto distinct biomolecule coronas formed on the surface of the distinct particle types. The particle types included in the particle panels disclosed herein are particularly well suited to enriching for a high number of proteins across a wide dynamic range in an unbiased fashion. The combinations of particle types selected for inclusion in a particle panel of the present disclosure are varied in their physicochemical properties (e.g., size, surface charge, core material, shell material, surface chemistry, porosity, morphology, and other properties). However, particle types may also share several of said physicochemical properties. "Biomolecule corona" as used herein can be used interchangeably with the term "protein corona," and refers to the formation of a layer of proteins on the surface of a particle after the particle has been contacted with a sample (e.g., plasma). This method may be referred to interchangeably as corona analysis or, in some examples, "Proteograph" analysis, which combines a multi-particle type protein corona strategy with mass spectrometry (MS). Particle types included in the particle panels disclosed herein can be superparamagnetic and are, thus, rapidly separated or isolated from unbound protein (proteins that have not adsorbed onto the surface of a particle to form the corona) in a sample, after incubation of the particle in the sample. A biomolecule may include a protein. Methods that include biomolecule coronas or protein coronas may include biomolecules or proteins, or vice versa.

Disclosed herein methods that include obtaining a data set comprising protein information from biomolecule coronas that correspond to physicochemically distinct particles incubated with a biofluid sample from a subject; and using a classifier to identify the biofluid sample being indicative of a healthy state, a cancer state, or a comorbidity thereof in the subject, based on the data set.

Disclosed herein methods that include obtaining a data set comprising proteins detected in biomolecule coronas corresponding to physicochemically distinct particles incubated with a biological sample comprising a biofluid or blood sample that has had red blood cells removed (e.g. a cell free biological sample such as plasma); and using a classifier to identify a disease state based on the data set.

Disclosed herein methods of evaluating a status of a cancer, comprising: measuring biomarkers in a biological sample from a subject suspected of having the cancer to obtain biomarker measurements from biomarkers such as those described herein. The biomarkers may comprise one or more biomarkers selected from the group consisting of: Angiopoietin-related protein 6 (ANGL6), Serine protease HTRA1 (HTRA1), Peroxidasin homolog (PXDN), Anthrax toxin receptor 2 (ANTR2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), Platelet glycoprotein Ib beta chain (GP1BB).

Disclosed herein methods for assaying one or more biomarkers in a sample from a subject suspected of having a lung cancer, comprising: measuring the one or more biomarkers such as a biomarker selected from the group consisting of: Angiopoietin-related protein 6 (ANGL6), Palmitoleoyl-protein carboxylesterase NOTUM (NOTUM), Cartilage intermediate layer protein 1 (CILP1), 60S acidic ribosomal protein P2 (RLA2), and Platelet glycoprotein Ib beta chain (GP1BB), or a peptide fragment thereof, in the sample to detect a presence, absence, or amount of the one or more biomarkers.

Disclosed herein methods for assaying one or more biomarkers in a sample from a subject suspected of having non-small cell lung carcinoma (NSCLC), comprising: measuring the one or more biomarkers such as a biomarker selected from the group consisting of: Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB), or a peptide fragment thereof, in the sample to detect a presence, absence, or amount of the one or more biomarkers.

Disclosed herein methods of treatment, comprising: (a) obtaining or receiving a measurement of one or more biomarkers such as a biomarker selected from the group consisting of: Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB), or a peptide fragment thereof, in a sample from a subject suspected of having a lung cancer; and (b) administering a lung cancer treatment to the subject based on a presence of the one or more biomarkers measured in (a), and monitoring the subject without providing the lung cancer treatment to the subject based on an absence of the one or more biomarkers in (a).

Disclosed herein methods that include (a) assaying a biological sample from a subject to identify biomolecules; and (b) using a classifier to identify that the sample is positive or negative for non-small cell lung cancer (NSCLC) based on the biomolecules identified in (a), wherein the classifier is generated with data from samples assayed using a plurality of particles having physicochemically distinct properties to yield the data.

Disclosed herein are systems that include: (a) a communication interface that receives, over a communication network, biomolecule data from a plurality of particles having physicochemically distinct properties and having been exposed to a sample from a subject comprising the biomolecules; and (b) a computer in communication with the communication interface, wherein the computer comprises a computer processor and a computer readable medium comprising machine-executable code that, upon execution by the computer processor, implements a method comprising: (i) receiving, over the communication network, the biomolecule data, (ii) combining the biomolecule data to generate a biomolecule fingerprint for the sample, and (iii) assigning a label to the biomolecule fingerprint, wherein the label corresponds to a presence of absence of a non-small cell lung cancer (NSCLC) in the subject.

Disclosed herein are systems that include: a communication interface that receives, over a communication network, biomarker data from a sample from a subject suspected of having a non-small cell lung cancer (NSCLC), wherein the sample comprises the biomarkers, and wherein the biomarkers comprise one or more biomarkers selected from the group consisting of: Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB), or a peptide fragment thereof.

Biomarkers

Biomarkers disclosed herein (e.g. related to a disease state such as NSCLC, a comorbidity, or a healthy state) can include at least one of the following: Protein S100-A9 (P06702; S10A9_HUMAN), C-reactive protein (P02741; CRP_HUMAN), Inter-alpha-trypsin inhibitor heavy chain H2 (P19823; ITIH2_HUMAN), Protein S100-A8 (P05109; S10A8_HUMAN), Serine protease HTRA1 (Q92743; HTRA1_HUMAN), Angiopoietin-related protein 6 (Q8NI99; ANGL6_HUMAN), Haptoglobin-related protein (P00739; HPTR_HUMAN), C—C motif chemokine 18 (P55774; CCL18_HUMAN), Actin, cytoplasmic 1 (P60709; ACTB_HUMAN), Actin, cytoplasmic 2 (P63261; ACTG_HUMAN), Serum amyloid A-1 protein (PODJI8; SAA1_HUMAN), Immunoglobulin kappa constant (P01834; IGKC_HUMAN), Angiopoietin-related protein 6 (Q8NI99; ANGL6_HUMAN), Peroxidasin homolog (Q92743; PXDN_HUMAN), Anthrax toxin receptor 2 (P58335; ANTR2_HUMAN), Tubulin alpha-1A chain (Q71U36; TBA1A_HUMAN), Syndecan-1 (P18827; SDC1_HUMAN), Serum amyloid A-2 protein (PODJI9; SAA2_HUMAN), Versican core protein (P13611; CSPG2_HUMAN), Anthrax toxin receptor 1 (Q9H6X2; ANTR1_HUMAN), Palmitoleoyl-protein carboxylesterase NOTUM (Q6P988; NOTUM_HUMAN), Cartilage intermediate layer protein 1 (O75339; CILP1_HUMAN), Calpain-2 catalytic subunit (P17655; CAN2_HUMAN), 60S acidic ribosomal protein P2 (P05387; RLA2_HUMAN), Beta-galactoside alpha-2,6-sialyltransferase 1 (P15907; SIAT1_HUMAN), and Platelet glycoprotein Ib beta chain (P13224; GP1BB_HUMAN). The biomarkers may include any biomarker or biomarkers in FIG. 11A-11C. Any one or more of the above biomarkers in various combinations can be used to train a classifier for distinguishing if a subject has lung cancer (e.g., NSCLC) or is co-morbid or healthy. In some embodiments, at least one of said biomarkers, at least two of said biomarkers, at least three of said biomarkers, at least four of said biomarkers, at least five of said biomarkers, at least six of said biomarkers, at least seven of said biomarkers, at least eight of said biomarkers, at least nine of said biomarkers, at least 10 of said biomarkers, at least 15 of said biomarkers, at least 20 of said biomarkers, at least 25 of said biomarkers, or all of said biomarkers together can be used to train a classifier for distinguishing if a subject has lung cancer (e.g., NSCLC) or is co-morbid or healthy. In some embodiments, at least one of said biomarkers, at least two of said biomarkers, at least three of said biomarkers, at least four of said biomarkers, at least five of said biomarkers, at least six of said biomarkers, at least seven of said biomarkers, at least eight of said biomarkers, at least nine of said biomarkers, at least 10 of said biomarkers, at least 15 of said biomarkers, at least 20 of said biomarkers, at least 25 of said biomarkers, or all of said biomarkers together can be used in a diagnostic assay to determine if a subject has lung cancer. The diagnostic assay can be carried out with the trained classifiers disclosed herein.

The present disclosure provides methods for detecting low abundance peptides in complex biological samples. Many of the diagnostic peptides of the present disclosure are inaccessible through traditional blood analysis methods due to the high concentrations of albumin, immunoglobulins, and other high abundance blood proteins. A diagnostic peptide may be present at 3-, 4-, 5-, 6-, 7-, 8-, 9-, 10-, 11-, 12- or more orders of magnitude lower concentration than the highest abundance proteins in a blood sample, and accordingly will cannot be detected by many traditional proteomic methods. The present disclosure not only provides methods for enriching low abundance biomolecules (e.g., proteins) from complex biological samples such as plasma, but also for quantifying the enriched biomolecules.

Examples of lung cancer diagnostic peptides are provided in TABLE 1. A method of the present disclosure may comprise assaying a sample from a subject to detect a presence, absence, or abundance of one or more peptides or fragments of peptides from among the peptides listed in TABLE 1. In some cases, a method comprises identifying a ratio between abundances of two peptides or fragments of peptides from among the peptides listed in TABLE 1. In some cases, a method comprises identifying a ratio between abundances of a peptide or fragment of a peptide from among the peptides listed in TABLE 1 and a separate peptide from the same biological sample. For example, a method may comprise identifying a ratio of the relative abundance of APOC1 and ceruloplasmin in a plasma sample from a subject suspected of having lung cancer. In some cases, the method comprises assaying the sample to detect a presence, absence, or abundance of one or more peptides or fragments of peptides from among the group consisting of Angiopoietin-related protein 6 (ANGL6), Palmitoleoyl-protein carboxylesterase NOTUM (NOTUM), Cartilage intermediate layer protein 1 (CILP1), 60S acidic ribosomal protein P2 (RLA2), and Platelet glycoprotein Ib beta chain (GP1BB). In some cases, the method comprises assaying a sample to detect a presence, absence, or abundance of at least 2, at least 3, at least 4, at least 5, at least 6, at least 8, at least 10, at least 12, at least 15, at least 20, at least 25, at least 30, or at least 35 peptides or fragments of peptides from among the peptides listed in TABLE 1.

The methods of the present disclosure enable quantification of disparate biomarkers spanning wide concentration ranges. In some cases, cancer (e.g., NSCLC) is evidenced by the relative concentrations of two or more proteins from a sample from a patient. In some cases, a method of the present disclosure comprises identifying abundance (e.g., concentration) ratios between at least 2 peptides from among the peptides listed in TABLE 1. In some cases, a method of the present disclosure comprises identifying abundance ratios between at least 3 peptides from among the peptides listed in TABLE 1. In some cases, a method of the present disclosure comprises identifying abundance ratios between at least 4 peptides from among the peptides listed in TABLE 1. In some cases, a method of the present disclosure comprises identifying abundance ratios between at least 5 peptides from among the peptides listed in TABLE 1. In some cases, a method of the present disclosure comprises identifying abundance ratios between at least 6 peptides from among the peptides listed in TABLE 1. In some cases, a method of the present disclosure comprises identifying abundance ratios between at least 7 peptides from among the peptides listed in TABLE 1. In some cases, a method of the present disclosure comprises identifying abundance ratios between at least 8 peptides from among the peptides listed in TABLE 1. In some cases, a method of the present disclosure comprises identifying abundance ratios between at least 9 peptides from among the peptides listed in TABLE 1. In some cases, a method of the present disclosure comprises identifying abundance ratios between at least 10 peptides from among the peptides listed in TABLE 1. In some cases, a method of the present disclosure comprises identifying abundance ratios between at least 12 peptides from among the peptides listed in TABLE 1. In some cases, a method of the present disclosure comprises identifying abundance ratios between at least 15 peptides from among the peptides listed in TABLE 1. In some cases, a method of the present disclosure comprises identifying abundance ratios between at least 20 peptides from among the peptides listed in TABLE 1. In some cases, a method of the present disclosure comprises identifying abundance ratios between at least 25 peptides from among the peptides listed in TABLE 1. In some cases, the sample is a blood sample (e.g., plasma).

In some cases, the method comprises assaying a sample to detect a presence, absence, or abundance of at least 2, at least 3, at least 4, or all 5 of ANGL6, NOTUM, CILP1, RLA2 or GP1BB. In some cases, one or more peptides or fragments of peptides from among the peptides listed in TABLE 1 are selected from the group consisting of actin (e.g., beta actin), anthrax toxin receptor 2, cartilage intermediate layer protein 1, collectin 11, and kallistatin. In some cases, one or more peptides or fragments of peptides from among the peptides listed in TABLE 1 are selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some cases, one or more peptides or fragments of peptides from among the peptides listed in TABLE 1 are selected from the group consisting of wherein the one or more biomarkers further comprise Leucine-rich alpha-2-glycoprotein (A2GL), Actin, cytoplasmic 1 (ACTB), Actin, cytoplasmic 2 (ACTG), Apolipoprotein C-I (APOC1), Apolipoprotein M (APOM), Voltage-dependent calcium channel subunit alpha-2/delta-1 (CA2D1), Cadherin-13 (CAD13), Beta-Ala-His dipeptidase (CNDP1), Ciliary neurotrophic factor receptor subunit alpha (CNTFR), Collectin-11 (COL11), C-reactive protein (CRP), Hemoglobin subunit alpha (HBA), Haptoglobin-related protein (HPT), Haptoglobin-related protein (HPTR), Inter-alpha-trypsin inhibitor heavy chain H2 (ITIH2), Kallistatin (KAIN), Plasma kallikrein (KLKB1), Neural cell adhesion molecule 1 (NCAM1), Protein S100-A8 (S10A8), Protein S100-A9 (S10A9), and Structural maintenance of chromosomes protein 4 (SMC4). In some cases, one or more peptides or fragments of peptides from among the peptides listed in TABLE 1 are selected from the group consisting of A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 or SMC4. In some cases, one or more peptides or fragments of peptides from among the peptides listed in TABLE 1 comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 or SMC4.

TABLE 1

Diagnostic Peptides

| Peptide | Approximate Blood Plasma Concentration (mg/ml) in some average patient populations |
|---|---|
| 6 sialyltransferase 1 (SIAT1/ST6GAL1) | $1.5 \times 10^{-5}$ |
| 60 S acidic ribosomal protein P2 (RLA2) | $7.3 \times 10^{-7}$ |
| Actin | — |
| Angiopoietin related protein 6 (ANGL6) | $4.5 \times 10^{-7}$ |
| Anthrax toxin receptor 1 (ANTR1) | $4.1 \times 10^{-6}$ |
| Anthrax toxin receptor 2 (ANTR2) | $6.6 \times 10^{-6}$ |
| Apolipoprotein C I (APOC1) | $4.0 \times 10^{-4}$ |
| Apolipoprotein M (APOM); | $8.6 \times 10^{-6}$ |
| Beta Ala His dipeptidase (CNDP1) | $1.9 \times 10^{-3}$ |
| Beta-galactoside alpha-2,6-sialyltransferase 1 (SIAT1/ST6Gal I) | $1.5 \times 10^{-5}$ |
| C motif chemokine 18 (CCL18) | $5.3 \times 10^{-5}$ |
| C reactive protein (CRP) | $1.7 \times 10^{-3}$ |
| Cadherin 13 (CAD13) | $2.3 \times 10^{-4}$ |
| Calpain 2 Catalytic Subunit (CAN2) | $1.5 \times 10^{-6}$ |
| Cartilage intermediate layer protein 1 (CILP1) | $1.1 \times 10^{-5}$ |
| Ciliary neurotrophic factor receptor subunit alpha (CNTFR) | $3.6 \times 10^{-5}$ |
| Collectin 11 (COL11) | $3.0 \times 10^{-5}$ |
| Cytoplasmic 1 (ACTB) | — |
| Cytoplasmic 2 (ACTG) | — |
| Haptoglobin related protein (HPT/HPR) | $4.9 \times 10^{-2}$ |
| Hemoglobin subunit alpha (HBA) | $1.7 \times 10^{-2}$ |
| Inter alpha trypsin inhibitor heavy chain H2 (ITIH2) | $2.2 \times 10^{-2}$ |
| Kallistatin (KAIN) | $2.2 \times 10^{-3}$ |
| Leucine rich alpha glycoprotein (A2GL) | — |
| Neural cell adhesion molecule 1 (NCAM1) | $2.8 \times 10^{-3}$ |
| Palmitoleoyl protein carboxylesterase (NOTUM) | $5.9 \times 10^{-8}$ |
| Peroxidasin homolog (PXDN) | $4.0 \times 10^{-6}$ |
| Plasma kallikrein (KLKB1) | $2.9 \times 10^{-2}$ |
| Platelet glycoprotein Ib beta chain (GP1BB) | $1.1 \times 10^{-4}$ |
| Protein S100 A8 (S10A8) | $3.0 \times 10^{-6}$ |
| Protein S100 A9 (S10A9) | $8.4 \times 10^{-6}$ |
| Serine protease HTRA1 (HTRA1) | $1.2 \times 10^{-6}$ |
| Serum amyloid A2 protein (SAA2) | $1.1 \times 10^{-2}$ |
| Syndecan 1 (SDC1) | $6.3 \times 10^{-5}$ |
| Structural maintenance of chromosomes protein 4 (SMC4) | — |
| Tubulin alpha 1A chain (TBA1A) | — |
| Versican core protein (CSPG2) | $5.2 \times 10^{-6}$ |
| Voltage dependent calcium channel subunit alpha 2/delta 1 (CA2D1) | — |

In some cases, a method comprises detecting a presence, absence, or abundance of one or more peptides selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some cases, a method comprises identifying a ratio between abundances of two peptides selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some cases, a method comprises detecting a presence, absence, or abundance of at least 2, at least 3, at least 4, at least 5, at least 6, at least 8, at least 10, at least 12, or at least 15 peptides selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB).

The biomarkers (e.g. proteins) may include an angiopoietin-related protein, a serine protease, a peroxidasin homolog, a C—C motif chemokine, an anthrax toxin receptor, a tubulin protein, a syndecan protein, a serum amyloid A protein, a versican protein, an anthrax toxin receptor protein, a palmitoleoyl-protein carboxylesterase protein, a cartilage intermediate layer protein, a calpain protein or subunit, a 60S acidic ribosomal protein, a beta-galactoside alpha-2,6-sialyltransferase protein, or a platelet glycoprotein, or a subunit or fragment of any of the aforementioned proteins. A biomarker may include an angiopoietin-related protein. A biomarker may include a serine protease. A biomarker may include a peroxidasin homolog. A biomarker may include a C—C motif chemokine. A biomarker may include an anthrax toxin receptor. A biomarker may include a tubulin protein. A biomarker may include a syndecan protein. A biomarker may include a serum amyloid A protein. A biomarker may include a versican protein. A biomarker may include an anthrax toxin receptor protein. A biomarker may include a palmitoleoyl-protein carboxylesterase protein. A biomarker may include a cartilage intermediate layer protein. A biomarker may include a calpain protein or subunit. A biomarker may include a 60S acidic ribosomal protein. A biomarker may include a beta-galactoside alpha-2,6-sialyltransferase protein. A biomarker may include a platelet glycoprotein. A biomarker may be secreted.

The biomarkers (e.g. proteins) may include Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB). The biomarkers (e.g. proteins) may include Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some cases, the biomarker is a secreted protein.

The biomarkers may include ANGL6, HTRA1, PXDN, ANTR2, CSPG2, ANTR1, NOTUM, CILP1, CAN2, or GP1BB. The biomarkers may include ANGL6, HTRA1, PXDN, ANTR2, CSPG2, ANTR1, NOTUM, CILP1, CAN2, and GP1BB.

In some cases, a method comprises assaying a plasma sample to detect a presence, absence, or abundance of one or more peptides or fragments of peptides from among the peptides listed in TABLE 1. In some cases, a method comprises assaying a buffy coat sample to detect a presence, absence, or abundance of one or more peptides or fragments of peptides from among the peptides listed in TABLE 1. In some cases, a method comprises assaying a granulocyte sample to detect a presence, absence, or abundance of one or more peptides or fragments of peptides from among the peptides listed in TABLE 1. In some cases, a method comprises assaying homogenized tissue (e.g. a homogenized lung biopsy tissue sample) to detect a presence, absence, or abundance of one or more peptides or fragments of peptides from among the peptides listed in TABLE 1.

The present methods enable rapid and deep biomolecule profiling from complex biological samples. In many cases, a method detects and identifies hundreds or thousands of distinct biomolecules. Such broad analysis not only enables deeper profiling of complex samples, but also increases the diagnostic utility of individual peptides. A method of the present disclosure may comprise assaying a sample from a subject to detect a presence, absence, or abundance of at least 50 peptides from a biological sample along with one or more additional peptides or fragments of peptides from among the peptides listed in TABLE 1. A method of the present disclosure may comprise assaying a sample from a subject to detect a presence, absence, or abundance of at least 100 peptides from a biological sample along with one or more additional peptides or fragments of peptides from among the peptides listed in TABLE 1. A method of the present disclosure may comprise assaying a sample from a subject to detect a presence, absence, or abundance of at least 200 peptides from a biological sample along with one or more additional peptides or fragments of peptides from among the peptides listed in TABLE 1. A method of the present disclosure may comprise assaying a sample from a subject to detect a presence, absence, or abundance of at least 400 peptides from a biological sample along with one or more additional peptides or fragments of peptides from among the peptides listed in TABLE 1. A method of the present disclosure may comprise assaying a sample from a subject to detect a presence, absence, or abundance of at least 600 peptides from a biological sample along with one or more additional peptides or fragments of peptides from among the peptides listed in TABLE 1. A method of the present disclosure may comprise assaying a sample from a subject to detect a presence, absence, or abundance of at least 800 peptides from a biological sample along with one or more additional peptides or fragments of peptides from among the peptides listed in TABLE 1. A method of the present disclosure may comprise assaying a sample from a subject to detect a presence, absence, or abundance of at least 1000 peptides from a biological sample along with one or more additional peptides or fragments of peptides from among the peptides listed in TABLE 1. A method of the present disclosure may comprise assaying a sample from a subject to detect a presence, absence, or abundance of at least 1200 peptides from a biological sample along with one or more additional peptides or fragments of peptides from among the peptides listed in TABLE 1. A method of the present disclosure may comprise assaying a sample from a subject to detect a presence, absence, or abundance of at least 1400 peptides from a biological sample along with one or more additional peptides or fragments of peptides from among the peptides listed in TABLE 1. A method of the present disclosure may comprise assaying a sample from a subject to detect a presence, absence, or abundance of at least 1600 peptides from a biological sample along with one or more additional peptides or fragments of peptides from among the peptides listed in TABLE 1. A method of the present disclosure may comprise assaying a sample from a subject to detect a presence, absence, or abundance of at least 1800 peptides from a biological sample along with one or more additional peptides or fragments of peptides from among the peptides listed in TABLE 1. A method of the present disclosure may comprise identifying abundance or signal intensity (e.g., mass spectrometric signal intensity) ratios between at least a subset of the at least 50, at least 100, at least 200, at least 400, at least 600, at least 800, at least 1000, at least 1200, at least 1400, at least 1600, or at least 1800 peptides and one or more additional peptides or fragments of peptides from among the peptides listed in TABLE 1.

A method of the present disclosure may comprise monitoring a lung cancer progression over time. A method may comprise collecting two samples from a patient at two different points in time, and detecting at least two peptides from among the peptides listed in TABLE 1 in each of the samples. A method may comprise collecting two samples from a patient at two different points in time, and detecting at least three peptides from among the peptides listed in TABLE 1 in each of the samples. A method may comprise collecting two samples from a patient at two different points in time, and detecting at least four peptides from among the peptides listed in TABLE 1 in each of the samples. A method may comprise collecting two samples from a patient at two different points in time, and detecting at least five peptides from among the peptides listed in TABLE 1 in each of the samples. A method may comprise collecting two samples from a patient at two different points in time, and detecting at least six peptides from among the peptides listed in TABLE 1 in each of the samples. A method may comprise collecting two samples from a patient at two different points in time, and detecting at least seven peptides from among the peptides listed in TABLE 1 in each of the samples. A method may comprise collecting two samples from a patient at two different points in time, and detecting at least eight peptides from among the peptides listed in TABLE 1 in each of the samples. A method may comprise collecting two samples from a patient at two different points in time, and detecting at least nine peptides from among the peptides listed in TABLE 1 in each of the samples. A method may comprise collecting two samples from a patient at two different points in time, and detecting at least ten peptides from among the peptides listed in TABLE 1 in each of the samples. A method may comprise collecting two samples from a patient at two different points in time, and detecting at least twelve peptides from among the peptides listed in TABLE 1 in each of the samples. A method may comprise collecting two samples from a patient at two different points in time, and detecting at least fifteen peptides from among the peptides listed in TABLE 1 in each of the samples. A method may comprise collecting two samples from a patient at two different points in time, and detecting at least twenty peptides from among the peptides listed in TABLE 1 in each of the samples. The second of the two samples may be collected at least 1 week, at least 2 weeks, at least 3 weeks, at least 4 weeks, at least 5 weeks, at least 6 weeks, at least 8 weeks, at least 12 weeks, at least 15 weeks, at least 18 weeks, at least 24 weeks, at least 36 weeks, at least 52 weeks, at least 78 weeks, at least 104 weeks, at least 130 weeks, at least 156 weeks, at least 208 weeks, or at least 260 weeks apart. A sample or both samples may be collected during the course of a cancer treatment, such as chemotherapy, to determine the efficacy of the treatment. A sample may be collected during a cancer remission stage in order to detect the reemergence, dormancy, or progression to complete remission.

Disclosed herein are methods that include biomarkers. The biomarkers may include Angiopoietin-related protein 6 (ANGL6), Palmitoleoyl-protein carboxylesterase NOTUM (NOTUM), Cartilage intermediate layer protein 1 (CILP1), 60S acidic ribosomal protein P2 (RLA2), and Platelet glycoprotein Ib beta chain (GP1BB), or a peptide fragment thereof. The biomarkers may include at least 1, at least 2, at least 3, or at least 4, of: ANGL6, NOTUM, CILP1, RLA2 or GP1BB. The biomarkers may include ANGL6, NOTUM, CILP1, RLA2 and GP1BB. In some cases, any of these biomarkers are useful for identifying a lung cancer. The biomarkers may be included in a classifier for distinguishing the lung cancer.

Disclosed herein are methods that include biomarkers. The biomarkers may include Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB), or a peptide fragment thereof. The biomarkers may include at least 1, at least 2, at least 3, at least 4, at least 5, at least 6, at least 7, at least 8, at least 9, at least 10, at least 11, at least 12, at least 13, at least 14, or at least 15, of: ANGL6, HTRA1, PXDN, CCL18, ANTR2, TBA1A, SDC1, SAA2, CSPG2, ANTR1, NOTUM, CILP1, CAN2, RLA2, SIAT1 or GP1BB. The biomarkers may include ANGL6, HTRA1, PXDN, CCL18, ANTR2, TBA1A, SDC1, SAA2, CSPG2, ANTR1, NOTUM, CILP1, CAN2, RLA2, SIAT1 and GP1BB. The biomarkers may be included in a classifier.

Disclosed herein are methods that include biomarkers. The biomarkers may include Leucine-rich alpha-2-glycoprotein (A2GL), Actin, cytoplasmic 1 (ACTB), Actin, cytoplasmic 2 (ACTG), Apolipoprotein C-I (APOC1), Apolipoprotein M (APOM), Voltage-dependent calcium channel subunit alpha-2/delta-1 (CA2D1), Cadherin-13 (CAD13), Beta-Ala-His dipeptidase (CNDP1), Ciliary neurotrophic factor receptor subunit alpha (CNTFR), Collectin-11 (COL11), C-reactive protein (CRP), Hemoglobin subunit alpha (HBA), Haptoglobin-related protein (HPT), Haptoglobin-related protein (HPTR), Inter-alpha-trypsin inhibitor heavy chain H2 (ITIH2), Kallistatin (KAIN), Plasma kallikrein (KLKB1), Neural cell adhesion molecule 1 (NCAM1), Protein S100-A8 (S10A8), Protein S100-A9 (S10A9), or Structural maintenance of chromosomes protein 4 (SMC4). The biomarkers may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, of: A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 or SMC4. The biomarkers may include A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 and SMC4. The biomarkers may be included in a classifier.

Disclosed herein are methods or classifiers that include a biomarker (or multiple biomarkers). The biomarker may include ANGL6. The biomarker may include HTRA1. The biomarker may include PXDN. The biomarker may include CCL18. The biomarker may include ANTR2. The biomarker may include TBA1A. The biomarker may include SDC1. The biomarker may include SAA2. The biomarker may include CSPG2. The biomarker may include ANTR1. The biomarker may include NOTUM. The biomarker may include CILP1. The biomarker may include CAN2. The biomarker may include RLA2. The biomarker may include SIAT1. The biomarker may include GP1BB. The biomarker may include A2GL. The biomarker may include ACTB. The biomarker may include ACTG. The biomarker may include APOC1. The biomarker may include APOM. The biomarker may include CA2D1. The biomarker may include CAD13. The biomarker may include CNDP1. The biomarker may include CNTFR. The biomarker may include COL11. The biomarker may include CRP. The biomarker may include HBA. The biomarker may include HPT. The biomarker may include HPTR. The biomarker may include ITIH2. The biomarker may include KAIN. The biomarker may include KLKB1. The biomarker may include NCAM1. The biomarker may include S10A8. The biomarker may include S10A9. The biomarker may include SMC4.

Disclosed herein are methods or classifiers that include biomarkers. The biomarkers may exclude ANGL6. The biomarkers may exclude HTRA1. The biomarkers may exclude PXDN. The biomarkers may exclude CCL18. The biomarkers may exclude ANTR2. The biomarkers may exclude TBA1A. The biomarkers may exclude SDC1. The biomarkers may exclude SAA2. The biomarkers may exclude CSPG2. The biomarkers may exclude ANTR1. The biomarkers may exclude NOTUM. The biomarkers may exclude CILP1. The biomarkers may exclude CAN2. The biomarkers may exclude RLA2. The biomarkers may exclude SIAT1. The biomarkers may exclude GP1BB. The biomarkers may exclude A2GL. The biomarkers may exclude ACTB. The biomarkers may exclude ACTG. The biomarkers may exclude APOC1. The biomarkers may exclude APOM. The biomarkers may exclude CA2D1. The biomarkers may exclude CAD13. The biomarkers may exclude CNDP1. The biomarkers may exclude CNTFR. The biomarkers may exclude COL11. The biomarkers may exclude CRP. The biomarkers may exclude HBA. The biomarkers may exclude HPT. The biomarkers may exclude HPTR. The biomarkers may exclude ITIH2. The biomarkers may exclude KAIN. The biomarkers may exclude KLKB1. The biomarkers may exclude NCAM1. The biomarkers may exclude S10A8. The biomarkers may exclude S10A9. The biomarkers may exclude SMC4.

Classifiers

A method described herein may include use of a classifier. A method described herein may include generating a classifier. A method described herein may include using a classifier to identify a disease state based on the data set. A method described herein may include applying a classifier to biomarker measurements.

The method of determining a set of proteins associated with the disease or disorder and/or disease state include the analysis of the biomarkers (e.g. a corona or proteins) of the at least one or two samples. This determination, analysis or statistical classification is done by methods known in the art, including, but not limited to, for example, a wide variety of supervised and unsupervised data analysis, machine learning, deep learning, and clustering approaches including hierarchical cluster analysis (HCA), principal component analysis (PCA), Partial least squares Discriminant Analysis (PLS-DA), random forest, logistic regression, decision trees, support vector machine (SVM), k-nearest neighbors, naive bayes, linear regression, polynomial regression, SVM for regression, K-means clustering, and hidden Markov models, among others. In other words, the proteins (e.g. in the corona) of each sample are compared/analyzed with each other to determine with statistical significance what patterns are common between the proteins of the subject to determine a set of proteins that is associated with the disease or disorder or disease state. Any of such methods may be used to generate a classifier for use herein.

A model may be trained with the one or more biomarkers using deep learning, a hierarchical cluster analysis, a principal component analysis, a partial least squares discriminant analysis, a random forest classification analysis, a support vector machine analysis, a k-nearest neighbors analysis, a naive bayes analysis, a K-means clustering analysis, or a hidden Markov analysis. A model may be trained with the one or more biomarkers using deep learning. A model may be trained with the one or more biomarkers using a hierarchical cluster analysis. A model may be trained with the one or more biomarkers using a principal component analysis. A model may be trained with the one or more biomarkers using a partial least squares discriminant analysis. A model may be trained with the one or more biomarkers using a random forest classification analysis. A model may be trained with the one or more biomarkers using a support vector machine analysis. A model may be trained with the one or more biomarkers using a k-nearest neighbors analysis. A model may be trained with the one or more biomarkers using a naive bayes analysis. A model may be trained with the one or more biomarkers using a K-means clustering analysis. A model may be trained with the one or more biomarkers using a hidden Markov analysis. A method described herein may include use of the model. A method may include generating the model.

The model may be trained with measurements of biomarkers (such as any of those described herein) in a control sample from a control subject. In some cases, the one or more biomarkers the model is trained with do not include depleted plasma proteins. The control subject may have a specific stage of NSCLC.

Generally, machine learning algorithms are used to construct models that accurately assign class labels to examples based on the input features that describe the example (e.g., healthy, co-morbid, or NSCLC Stage 1, 2, or 3). In some case it may be advantageous to employ machine learning and/or deep learning approaches for the methods described herein. For example, machine learning can be used to associate a ser of biomarkers with various disease states (e.g. no disease, precursor to a disease, having early or late stage of the disease, etc.). For example, in some cases, one or more machine learning algorithms are employed in connection with a method of the invention to analyze data detected and obtained by the protein coronas and sets of proteins derived therefrom. For example, in one embodiment, machine learning can be coupled with the particle panels described herein to determine not only if a subject has a pre-stage of cancer, cancer or does not have or develop cancer, but also to distinguish the type of cancer, for example, distinguish a lung cancer such as NSCLC. The classifier may have an increased protein detection consistency relative to a second classifier generated using proteomic data from depleted plasma samples. For example, the classifier may be generated by contacting samples with particles, and may have an increased protein detection consistency relative to a second classifier generated using proteomic data from depleted plasma samples not contacted with the particles.

Determination, analysis or statistical classification is done by methods known in the art, including, but not limited to, for example, a wide variety of supervised and unsupervised data analysis and clustering approaches such as hierarchical cluster analysis (HCA), principal component analysis (PCA), Partial least squares Discriminant Analysis (PLSDA), machine learning (also known as random forest), logistic regression, decision trees, support vector machine (SVM), k-nearest neighbors, naive bayes, linear regression, polynomial regression, SVM for regression, K-means clustering, and hidden Markov models, among others. A system or method may analyze biomarkers such as a protein set or protein corona of the present disclosure. The analysis may include comparing/analyzing the biomarkers of one or more (e.g. several) samples to determine with statistical significance what patterns are common between the biomarkers to determine biomarkers (e.g. a protein set) that is associated with the biological state. The system or method can develop classifiers to detect and discriminate different protein sets or protein corona (e.g., characteristic of the composition of a protein corona). Data collected from a method or system described herein (e.g. a system including a sensor array) can be used to train a machine learning algorithm, for example an algorithm that receives array measurements from a patient and outputs specific biomolecule corona compositions from each patient.

Machine learning can be generalized as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FPgrowth algorithm; Hierarchical clustering, such as Singlelinkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory.

The methods described herein may include use of a classifier to identify or distinguish a disease state such as cancer (e.g. lung cancer or NSCLC). The classifier may distinguish the disease state from a comorbidity such as a chronic lung disorder, chronic obstructive pulmonary disease, emphysema, cardiovascular disease, hypertension, pulmonary fibrosis, or asthma.

The classifier may be generated by removing or filtering out biomolecules associated with acute phase response. In some aspects, said classifier is configured to remove acute-phase-response bias or stress protein bias. In some aspects, said classifier comprises features that relate to proteins. Said features may be selected to exclude acute-phase response and/or stress protein bias in said biological sample.

Figure 11A:
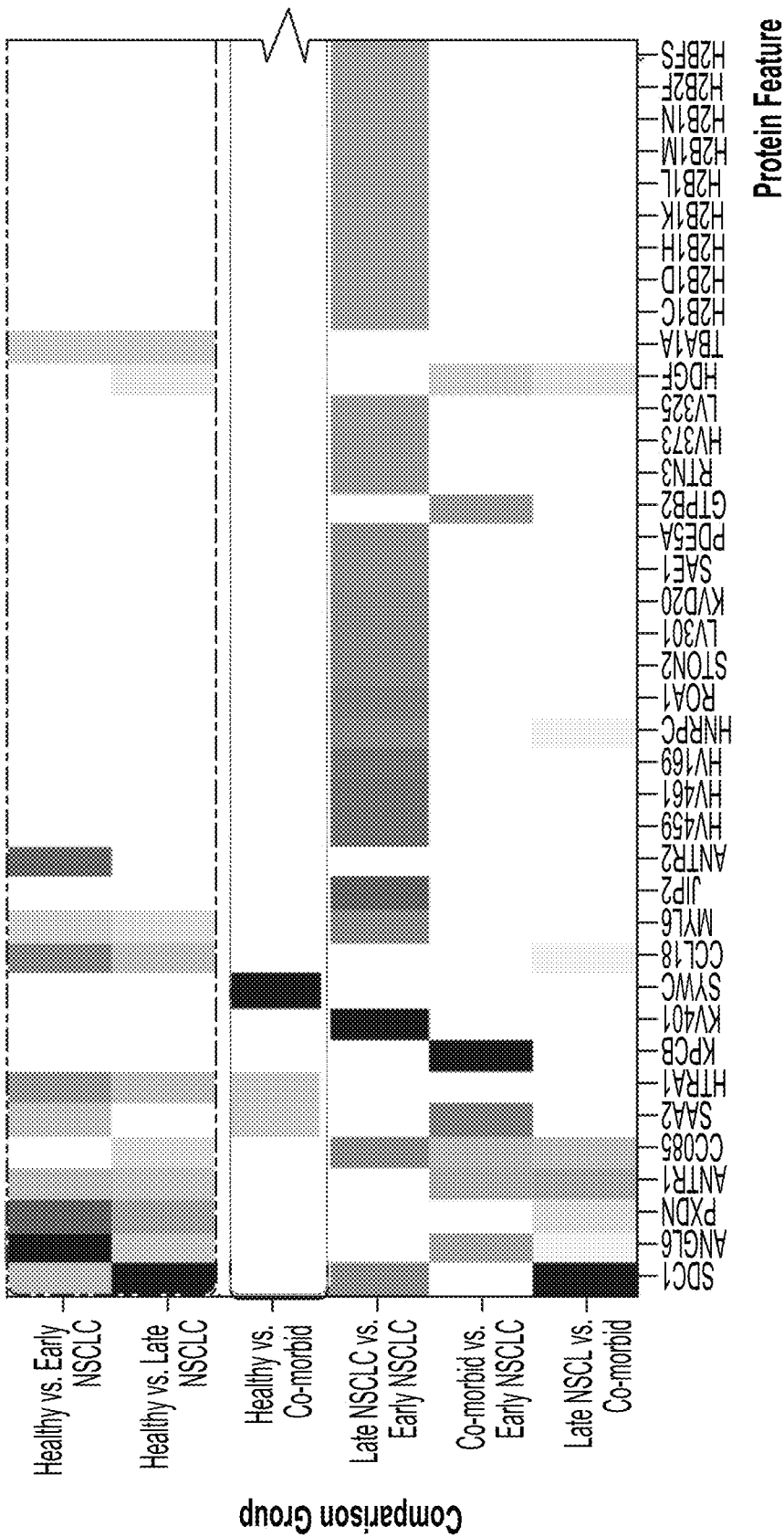
FIG. 11A-11B show the differentiation of important features in study group comparisons.
Figure 11B:
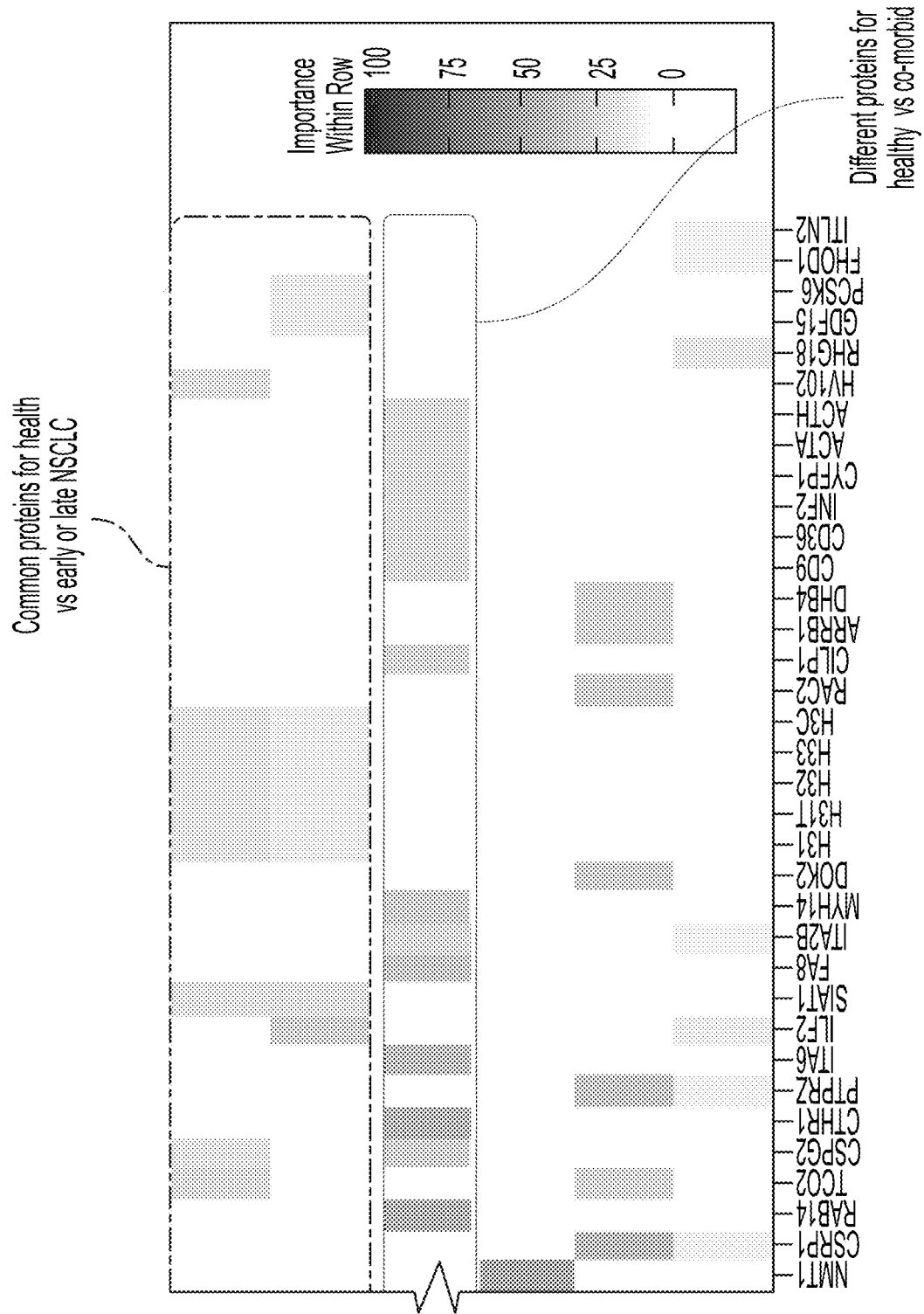

The classifier may comprises features (e.g. biomarker information) to distinguish between a disease state or other state (e.g. a healthy or comorbid state) in FIG. 11A-11B. Any of the features or biomarkers in FIG. 11A-11B may be used in a method that distinguishes between the disease state or other state. The biomarker information may include information comprising an expression level or an amount of a biomarker.

The classifier may comprises features to distinguish between the presence or absence of NSCLC. For example, the features may include information on one of more biomarkers including: SDC1, ANGL6, PXDN, ANTR1, CC085, SAA2, HTRA1, KPCB, KV401, CCL18, MYL6, ANTR2, GTPB2, HDGF, TBA1A, CSRP1, TCO2, CSPG2, PTPRZ, ILF2, SIAT1, ITA2B, DOK2, H31, H31T, H32, H33, H3C, RAC2, ARRB1, DHB4, HV102, RHG18, GDF15, PCSK6, FHOD1, or ITLN2, or any combination thereof. Any of these features or biomarkers may be included in a method that distinguishes between the presence or absence of NSCLC.

The classifier may comprises features to distinguish between a healthy state and early stage NSCLC (e.g. NSCLC stage 1, 2, and/or 3). Such features may include information on one of more biomarkers including: SDC1, ANGL6, PXDN, ANTR1, SAA2, HTRA1, CCL18, MYL6, ANTR2, TBA1A, TCO2, CSPG2, SIAT1, H31, H31T, H32, H33, H3C, or HV102, or any combination thereof. Any of these features or biomarkers may be included in a method that distinguishes between a healthy state and early stage NSCLC.

The classifier may comprises features to distinguish between a healthy state and late stage NSCLC (e.g. NSCLC stage 4). Such features may include information on one of more biomarkers including: SDC1, ANGL6, PXDN, ANTR1, CC085, HTRA1, CCL18, MYL6, HDGF, TBA1A, ILF2, SIAT1, H31, H31T, H32, H33, H3C, GDF15, or PCSK6, or any combination thereof. Any of these features or biomarkers may be included in a method that distinguishes between a healthy state and late stage NSCLC.

The classifier may comprises features to distinguish between a healthy state and a comorbidity. Such features may include information on one of more biomarkers including: SAA2, HTRA1, SYWC, RAB14, CSPG2, CTHR1, ITA6, FAB, ITA2B, DOK2, CILP1, CD9, CD36, INF2, CYFP1, ACTA, or ACTH, or any combination thereof. Any of these features or biomarkers may be included in a method that distinguishes between a healthy state and a comorbidity.

The classifier may comprises features to distinguish between early stage NSCLC and late stage NSCLC. For example, the features may include information on one of more biomarkers including: SDC1, CC085, KV401, MYL6, JIP2, HV459, HV461, HV169, HNRPC, ROA1, STON2, LV301, KVD20, SAE1, PDE5A, RTN3, HV373, LV325, H2B1C, H2B1D, H2B1H, H2B1K, H2B1L, H2B1M, H2B1N, H2B2F, H2BFS, or NMT1, or any combination thereof. Any of these features or biomarkers may be included in a method that distinguishes between early stage NSCLC and late stage NSCLC.

The classifier may comprises features to distinguish between early stage NSCLC and a comorbidity. For example, the features may include information on one of more biomarkers including: ANGL6, ANTR1, CC085, SAA2, KPCB, GTPB2, HDGF, CSRP1, TCO2, PTPRZ, DOK2, RAC2, ARRB1, or DHB4, or any combination thereof. Any of these features or biomarkers may be included in a method that distinguishes between early stage NSCLC and a comorbidity.

The classifier may comprises features to distinguish between late stage NSCLC and a comorbidity. For example, the features may include information on one of more biomarkers including: SDC1, ANGL6, PXDN, ANTR1, CC085, CCL18, HNRPC, HDGF, CSRP1, PTPRZ, ILF2, ITA2B, RHG18, FHOD1, or ITLN2, or any combination thereof. Any of these features or biomarkers may be included in a method that distinguishes between late stage NSCLC and a comorbidity.

Disease Detection

One or more of the biomarkers disclosed herein can be used in an assay for detection of cancer in a sample from a subject. For example, in some embodiments, the biomarkers disclosed herein can be used for detection of lung cancer in a sample from the subject. The lung cancer can be non-small cell lung cancer (NSCLC). The lung cancer can be adenosquamous carcinoma of the lung. The lung cancer can comprise a lung nodule. The lung cancer can be or include metastatic lung cancer. The lung cancer can be large cell neuroendocrine carcinoma. The lung cancer can be salivary gland-type lung carcinoma. The lung cancer can be mesothelioma. In some cases, the present disclosure provides methods of identifying a lung cancer biomarker disclosed herein from a sample from a patient (e.g., by mass spectrometry or ELISA). In some cases, the present disclosure provides methods of obtaining a sample from a subject, incubating said sample with the particle panels disclosed herein, and performing targeted mass spectrometry on the biomolecule corona formed on various particle types of the particle panel to assess for the presence or absence of one or more of the biomarkers disclosed herein associated with NSCLC. A classifier disclosed herein can be used to further process the protein data obtained using the methods described above to classify the sample as healthy, co-morbid, or NSCLC.

The biomarkers of the present disclosure may not only be used to detect the presence of lung cancer, but may also identify the type and stage of lung cancer in a patient. Determining lung cancer stage, type, and malignancy is often beyond the scope of present methods, as little is known about the genetic and molecular factors which mediate lung cancer progression. While treatment success is highly dependent on accurate lung cancer characterization, current methods for ascertaining information on the state of lung cancer in a patient are often slow, invasive, expensive, and time intensive. There is a long outstanding need for rapid, non-invasive methods which can accurately diagnose lung cancer stage and type. The present compositions and methods bridge this shortcoming by enabling lung cancer identification and characterization from small volumes of patient samples.

In many cases, a composition or method of the present disclosure can identify lung cancer from less than 100 mL, less than 50 mL, less than 30 mL, less than 25 mL, less than 20 mL, less than 15 mL, less than 10 mL, less than 8 mL, less than 6 mL, less than 5 mL, less than 3 mL, less than 2 mL, or less than 1 mL of blood (e.g., plasma) from a patient. Furthermore, a number of a compositions and methods of the present disclosure may determine a type of lung cancer from a patient from less than 100 mL, less than 50 mL, less than 30 mL, less than 25 mL, less than 20 mL, less than 15 mL, less than 10 mL, less than 8 mL, less than 6 mL, less than 5 mL, less than 3 mL, less than 2 mL, or less than 1 mL of blood (e.g., plasma) from the patient. The methods and compositions of the present disclosure may also determine a stage of a lung cancer from a patient from less than 100 mL, less than 50 mL, less than 30 mL, less than 25 mL, less than 20 mL, less than 15 mL, less than 10 mL, less than 8 mL, less than 6 mL, less than 5 mL, less than 3 mL, less than 2 mL, or less than 1 mL of blood (e.g., plasma) from the patient.

A method of the present disclosure may comprise monitoring cancer progression in a patient. Various methods of the present disclosure are able to distinguish between healthy, early stage, and late stage cancers. A method of the present disclosure may also be capable of determining whether a patient is in complete or partial remission. A method may thus comprise analyzing samples from a patient collected at separate points in time. Such methods may identify and then track health or cancer progression in a patient without the need for invasive or expensive procedures. Tracking early phase cancers can be particularly challenging and time intensive for a patient, as small, localized cancers often require biopsies or lengthy imaging sessions for detection. Conversely, the present disclosure provides a variety of methods for tracking small and localized cancers through blood analysis alone. For example, a patient with a stage 0 or stage 1 lung cancer may undergo bimonthly plasma analyses consistent with methods of the present disclosure to monitor for cancer metastasis or progression. A patient may undergo diagnostic analyses of the present disclosure in daily, twice weekly, weekly, biweekly, monthly, bimonthly, quarterly (once every 3 months), twice yearly, yearly, or biyearly intervals. A patient may be regularly monitored to track remission, early phase cancer status, late phase cancer status, or maintenance of a healthy or pre-cancerous status. In some cases, the particles and methods of the present disclosure can be used to diagnose lung cancer up to one year prior, up to two years prior, up to three years prior, up to four years prior, up to five years prior, up to six years prior, up to seven years prior, up to eight years prior, up to nine years prior, up to 10 years prior, up to 15 years prior, up to 20 years prior, or up to 25 years prior to development of symptoms of the lung cancer.

In some cases, the entire assay time from obtaining a sample, sample preparation, incubation of a particle panel with the sample, and LC-MS (e.g., targeted mass spectrometry) to identify proteins or protein groups, can be about 8 hours. In some embodiments, the entire assay time from a single pooled sample, including sample preparation and LC-MS, can be about at least 1 hour, at least 2 hours, at least 3 hours, at least 4 hours, at least 5 hours, at least 6 hours, at least 7 hours, at least 8 hours, at least 9 hours, at least 10 hours, under 20 hours, under 19 hours, under 18 hours, under 17 hours, under 16 hours, under 15 hours, under 14 hours, under 13 hours, under 12 hours, under 11 hours, under 10 hours, under 9 hours, under 8 hours, under 7 hours, under 6 hours, under 5 hours, under 4 hours, under 3 hours, under 2 hours, under 1 hour, at least 5 min to 10 min, at least 10 min to 20 min, at least 20 min to 30 min, at least 30 min to 40 min, at least 40 min to 50 min, at least 50 min to 60 min, at least 1 hour to 1.5 hours, at least 1.5 hour to 2 hours, at least 2 hour to 2.5 hours, at least 2.5 hour to 3 hours, at least 3 hour to 3.5 hours, at least 3.5 hour to 4 hours, at least 4 hour to 4.5 hours, at least 4.5 hour to 5 hours, at least 5 hour to 5.5 hours, at least 5.5 hour to 6 hours, at least 6 hour to 6.5 hours, at least 6.5 hour to 7 hours, at least 7 hour to 7.5 hours, at least 7.5 hour to 8 hours, at least 8 hour to 8.5 hours, at least 8.5 hour to 9 hours, at least 9 hour to 9.5 hours, or at least 9.5 hour to 10 hours.

A disease state may be identified with a sensitivity or specificity of about 80% or greater. The disease state may be identified with a sensitivity or specificity of about 85% or greater. The disease state may be identified with a sensitivity or specificity of about 90% or greater. The disease state may be identified with a sensitivity or specificity of about 95% or greater.

In some embodiments, any of the classifiers disclosed herein can be build using any of the biomarkers disclosed herein to determine whether a sample from a subject has a disease state selected from: healthy, co-morbid, NSCLC Stage 1, NSCLC Stage 2, NSCLC Stage 3, NSCLC Stage 4, or NSCLC Stages 1, 2, or 3. In some embodiments, the classifier is capable of distinguishing samples as healthy versus NSCLC Stages 1, 2, or 3 with a high sensitivity and high specificity. In some embodiments, the classifier is capable of distinguishing samples as co-morbid versus NSCLC Stages 1, 2, or 3 with a high sensitivity and high specificity.

The present disclosure provides a number of peptides which can be diagnostic of various cancers, including lung cancer. In some cases, the absence, presence, or abundance of a single peptide may be indicative of a particular cancer. However, in many cases, collective analysis of a plurality of peptides disclosed herein may yield considerably higher accuracy diagnoses. A method of the present disclosure may not only identify a cancer in a patient, but also the stage (e.g., stage I versus stage II, stage I versus stage III, early stage versus late stage), the degree of metastasis, and the tissue or site of origin. Furthermore, a method of the present disclosure may complement another form of analysis. For example, an immunohistological analysis of a tissue biopsy may be paired with a plasma proteomic analysis to increase the accuracy of a cancer diagnosis. Alternatively, a single method of the present disclosure may be sufficient for accurate cancer diagnosis.

An advantage of many of the methods of the present disclosure may be low invasiveness and minimal patient participation. In many cases, diagnostic peptides of the present disclosure may be identified in blood (e.g., whole blood, granulocyte, buffy coat, or plasma) samples, and may provide equal or greater diagnostic insight than intensive tissue biopsies or lengthy and expensive imaging procedures.

The methods described herein may include detection or discernment of a disease state. The disease state may comprise a cancer. The disease state may comprise lung cancer. The disease state may comprise non-small cell lung cancer (NSCLC). The lung cancer may include NSCLC. The NSCLC may comprise early stage NSCLC (e.g. stage 1 NSCLC, stage 2 NSCLC, or stage 3 NSCLC). The NSCLC may comprise late stage NSCLC (e.g. stage 4 NSCLC).

A method described herein may include identifying a subject as having a disease state such as a cancer based on the biomarker measurements. Disclosed herein are methods of evaluating a status of a cancer. The method may include measuring biomarkers in a biological sample. The sample may be from a subject suspected of having the cancer. The measurements may be to obtain biomarker measurements. The method may include obtaining the biomarker measurements. The biomarkers may include biomarkers described herein.

A method described herein may include identifying a biological sample from a subject as being indicative of a healthy state, a cancer state, or a comorbidity thereof in the subject, based on biomarker measurements obtained in the subject. The cancer may be a lung cancer such as NSCLC. The method may include use of a classifier such as a classifier described herein. The method may distinguish the comorbidity from the cancer state. The method may distinguish the healthy state from the cancer state. The method may distinguish the comorbidity from the healthy state. The pulmonary comorbidity may include a disease other than the cancer.

A method described herein may identify or distinguish a comorbidity. The comorbidity may be a pulmonary comorbidity. The pulmonary comorbidity may include a lung disease other than the cancer. The pulmonary comorbidity may be selected from the group consisting of: chronic obstructive pulmonary disease (COPD), emphysema, cardiovascular disease, hypertension, pulmonary fibrosis, asthma, a chronic lung disease, and any combination thereof. The pulmonary comorbidity may include COPD. The pulmonary comorbidity may include emphysema. The pulmonary comorbidity may include a cardiovascular disease. The pulmonary comorbidity may include hypertension. The pulmonary comorbidity may include pulmonary fibrosis. The pulmonary comorbidity may include asthma. The pulmonary comorbidity may include a chronic lung disease.

Disclosed herein is a method for assaying one or more biomarkers in a sample from a subject suspected of having a lung cancer. The method may include measuring the one or more biomarkers in the sample. The measurement may include detecting a presence of the one or more biomarkers. The measurement may include detecting an absence of the one or more biomarkers. The measurement may include detecting an amount of the one or more biomarkers. The biomarkers may include a biomarker selected from the group consisting of: Angiopoietin-related protein 6 (ANGL6), Palmitoleoyl-protein carboxylesterase NOTUM (NOTUM), Cartilage intermediate layer protein 1 (CILP1), 60S acidic ribosomal protein P2 (RLA2), and Platelet glycoprotein Ib beta chain (GP1BB), or a peptide fragment thereof.

Disclosed herein is a method for assaying one or more biomarkers in a sample from a subject suspected of having a lung cancer comprising non-small cell lung carcinoma (NSCLC). The measurement may include detecting a presence of the one or more biomarkers. The measurement may include detecting an absence of the one or more biomarkers. The measurement may include detecting an amount of the one or more biomarkers. The biomarkers may include a biomarker selected from the group consisting of: Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB), or a peptide fragment thereof.

A method may include comparing an amount of a biomarker to a control. The control may include an index. The control may include a threshold. The control may include a control sample from a control subject. In some cases, the control sample comprises a blood sample, a plasma sample, or a serum sample. In some cases, the control subject does not have the lung cancer.

In some cases, the lung cancer comprises a stage 1-4 NSCLC. In some cases, the subject has the lung cancer. In some cases, the control subject has a stage 1-4 NSCLC. In some cases, the NSCLC of the subject comprises a different stage than the NSCLC of the control subject.

The control subject may have a chronic lung disorder, chronic obstructive pulmonary disease, emphysema, cardiovascular disease, hypertension, pulmonary fibrosis, or asthma. The control subject may have a lung disorder. The control subject may have a chronic lung disorder. The control subject may have chronic obstructive pulmonary disease. The control subject may have emphysema. The control subject may have a cardiovascular disease. The control subject may have hypertension. The control subject may have fibrosis. The control subject may have pulmonary fibrosis. The control subject may have asthma.

A method may include identifying the subject as having the lung cancer, or as not having the lung cancer, based on the measurement of the one or more biomarkers. A method may include identifying a presence or absence of lung cancer cells or components thereof in the sample based on the measurement of the one or more biomarkers. A presence of the one or more biomarkers may be indicative of a presence of NSCLC cells or components thereof in the sample. A method may include identifying a likelihood of the subject having the lung cancer based on the measurement of the one or more biomarkers. A method may include identifying the subject as having the lung cancer based on the measurement of the one or more biomarkers. A method may include identifying the stage of the cancer based on the measurement.

A method may include assaying a biological sample from a subject to identify biomolecules. A method may include using a classifier to identify that the sample is positive for non-small cell lung cancer (NSCLC) based on the biomolecules identified. A method may include using a classifier to identify that the sample is negative for non-small cell lung cancer (NSCLC) based on the biomolecules identified. The classifier may be generated with data from samples assayed using a plurality of particles having physicochemically distinct properties to yield the data. The classifier may be trained using data from the sample, wherein the samples comprise known healthy samples and known NSCLC samples. The biomolecules may include proteins or biomarkers described herein. The data may include proteomic data identifying a presence or an absence of proteins in the samples.

Detection Methods

The present disclosure provides a variety of methods for detecting biomolecules (e.g. protein biomarkers) from a biological sample. Biomolecular (e.g., proteomic) data of the biological sample can be identified, measured, and quantified using a number of different analytical techniques. For example, proteomic data can be analyzed using SDS-PAGE or any gel-based separation technique. Alternatively, proteomic data can be identified, measured, and quantified using mass spectrometry, high performance liquid chromatography, LC-MS/MS, Edman Degradation, an immunoaffinity technique, binding reagent analysis (e.g., immunostaining or an aptamer binding assay), an enzyme linked immunosorbent assay (ELISA), chromatography, western blot analysis, mass spectrometric analysis, or any combination thereof. The biomolecules may be enriched on a particle or particle panel prior to analysis. A subset of biomolecules from a biological sample may be collected on a particle, optionally eluted into a solution, optionally treated (e.g., digested or chemically reduced), and analyzed. Particle-based biomolecule collection may enrich a biomolecule from a biological sample, thereby enabling rapid detection and quantification of a low abundance biomolecule.

Various methods of the present disclosure for detecting a biomolecule comprise binding reagent analysis. A biological sample or collection of biomolecules from a biological sample may be contacted with a target-specific binding reagent, such as an antibody, an affibody, an affimer, an alphabody, an avimer, a DARPin, a chimeric antigen receptor, a T-cell receptor, an aptamer, or a fragment thereof. A binding reagent may be detectable. A binding reagent may comprise a barcode sequence that enables detection and quantification of the binding reagent by nucleic acid sequencing analysis. A binding reagent may comprise an optically detectable label or moiety (e.g., a fluorescent protein such as GFP or YFP or a fluorescent dye). Binding reagent analysis may comprise a plurality of binding reagents targeting a plurality of biomolecules and comprising different detectable signals (e.g., nucleic acid barcode sequences or optically detectable moieties), thereby enabling multiplexed detection and quantification of selected biomarkers from the sample. For example, a sample may be contacted with a plurality of antibodies comprising distinct detectable labels and targeting different proteins from among the proteins listed in TABLE 1. In some cases, a binding reagent may contact a biomolecule covalently or non-covalently immobilized to a substrate (e.g., a membrane, a surface, a resin, or a slide). In some cases, a binding reagent may contact a biomolecule adsorbed to a particle (e.g., disposed in a biomolecule corona of a particle).

Various methods of the present disclosure for detecting a biomolecule comprise ELISA. A method may comprise sandwich ELISA analysis, in which a biomolecule (e.g., a peptide from among the peptides listed in TABLE 1) is contacted to a first antibody immobilized to a solid phase and a second antibody coupled to a detectable moiety (e.g., an optically detectable dye molecule), wherein the first antibody comprises a first paratope for a first epitope on the biomolecule and the second antibody comprises a second paratope for a second epitope on the biomolecule. An ELISA assay may comprise immobilizing a biomolecule of interest to a substrate (e.g., a glass slide or the bottom of a well of a multiwell plate), and contacting the biomolecule with a first antibody comprising a binding affinity for the biomolecule. The first antibody may be coupled to a detectable moiety, or may be contacted to a second antibody that is coupled to a detectable moiety and which binds to the first antibody. ELISA assays can comprise low detection limits (e.g., >1 pg/ml) for target detection and quantitation, and may thus be suitable for analyzing a cancer biomarker disclosed herein.

A method of the present disclosure may comprise mass spectrometric analysis of a biomolecule such as a protein, a peptide, or a portion thereof. The mass spectrometric analysis can be performed in tandem with a chromatographic separation technique, such as liquid chromatography, such that biomolecules or biomolecule fragments are subjected to mass spectrometric analysis at different points in time. Mass spectrometric analysis may comprise two or more mass analysis steps (e.g., tandem mass spectrometry), such that an ion is fragmented and then subjected to further analysis.

The methods described herein may include measuring a biomarker (e.g. one or more biomarkers) in a sample from a subject. Measuring a biomarker may include performing an assay method. Measuring a biomarker may include performing mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. Measuring a biomarker may include performing mass spectrometry. Measuring a biomarker may include performing chromatography. Measuring a biomarker may include performing liquid chromatography. Measuring a biomarker may include performing high-performance liquid chromatography. Measuring a biomarker may include performing solid-phase chromatography. Measuring a biomarker may include performing a lateral flow assay. Measuring a biomarker may include performing an immunoassay. Measuring a biomarker may include performing an enzyme-linked immunosorbent assay. Measuring a biomarker may include performing a blot such as a western blot. Measuring a biomarker may include performing dot blot. Measuring a biomarker may include performing immunostaining. Measuring a biomarker may include contacting a biological sample with a plurality of physicochemically distinct nanoparticles. Measuring a biomarker may include performing a combination of assay methods. For example, a method described herein may include use of particles followed by an immunoassay such as an ELISA to assess proteins or biomolecules of biomolecule or protein coronas. The methods described herein may include detecting the proteins of the biomolecule coronas by mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. The methods described herein may include detecting the proteins of the biomolecule coronas by mass spectrometry.

Measuring a biomarker may include using a detection reagent that binds to a protein and yields a detectable signal. The methods described herein may include detecting the proteins comprises measuring a readout indicative of the presence, absence or amounts of the proteins. Measuring a biomarker may include measuring a readout indicative of the presence, absence or amounts of the one or more biomarkers.

A method may include concentrating biomarkers in a sample prior to measuring the biomarkers. Measuring a biomarker may include concentrating a sample. Measuring a biomarker may include filtering a sample. Measuring a biomarker may include centrifuging a sample.

Measuring a biomarker may include contacting the sample with an assay reagent. The assay reagent may include a particle. The assay reagent may include an antibody. The assay reagent may include a biomolecule binding molecule.

Particles and Types

A disease detection method may include use of particles. The methods described herein may include contacting the biological sample with the physicochemically distinct particles to form the biomolecule coronas. A particle may adsorb biomolecules from a biological sample, thereby forming a biomolecule corona on the surface of the particle. Upon contact with the biological sample, a particle may adsorb a plurality of peptides, proteins, nucleic acids, lipids, saccharides, small molecules (such as metabolites (native and foreign), terpenes, polyketides, and cyclic peptides), or any combination thereof. Accordingly, a method may comprise collecting a subset of biomolecules from a biological sample (e.g., a complex biological sample such as human plasma) on a particle, and analyzing the biomolecules collected on the particle, analyzing the biomolecules remaining in the biological sample, or analyzing the biomolecules collected on the particle and the biomolecules remaining in the biological sample. A biomolecule, a biomolecule corona, or a portion thereof may be eluted from a particle and into a solution prior to analysis.

The relationship between particle properties and biomolecule corona composition can be leveraged to manipulate biomolecule collection from a sample. In some cases, a set of particle properties may favor binding of a particular biomolecule type, family, or superfamily. For example, humans express over 100 proteins from the Ras superfamily, which share a conserved GTP-binding motif within a 20 kilodalton (kDa) N-terminal domain. A particle or collection of particles (e.g., a mixture containing 5 types of particles) may be functionalized so as to favor Ras protein adsorption, and thus may be tuned to preferentially adsorb Ras proteins from complex biological samples, enabling their enrichment for further analysis.

A particle or a mixture of different particles may be tailored to broadly profile a sample. In many biological samples, a small number of biomolecules constitute the majority of biological material. For example, over 99% of the protein mass in human plasma is accounted for by just 20 of the roughly 3500 human plasma proteins. Analysis of such samples can be exceedingly challenging, as the small number of abundant biomolecules can saturate a detection or enrichment scheme. A particle or a collection of multiple particle types may be tuned to broadly profile complex biological, such that low abundance biomolecules are preferentially enriched over or along with high abundance biomolecules from complex biological samples. A particle or collection of multiple particle types may comprise similar binding affinities for a large number of biomolecules, thus favoring adsorption of a large number of biomolecules from a sample. A particle may comprise a low affinity for a high abundance or set of high abundance proteins in a sample, and may therefore preferentially adsorb and enrich low abundance biomolecules. A collection of particles may comprise particle types with affinities for different types or classes of biomolecules, such that the collection of particles adsorbs a broad range of biomolecules from the sample. Accordingly, the present disclosure provides a wide range of particle types with distinct physicochemical properties.

Particle types consistent with the methods disclosed herein can be made from various materials. For example, particle materials consistent with the present disclosure include metals, polymers, magnetic materials, and lipids. Magnetic particles may be iron oxide particles. Examples of metal materials include any one of or any combination of gold, silver, copper, nickel, cobalt, palladium, platinum, iridium, osmium, rhodium, ruthenium, rhenium, vanadium, chromium, manganese, niobium, molybdenum, tungsten, tantalum, iron and cadmium, or any other material described in U.S. Pat. No. 7,749,299, the contents of which are herein incorporated by reference in their entirety. A particle may be magnetic (e.g., ferromagnetic or ferrimagnetic). For example, a particle may comprise a superparamagnetic iron oxide nanoparticle (SPION).

The particles may include multiple physicochemically distinct particles (for example, 2 or more sets of physicochemically particles where 1 set of particles is physicochemically distinct from another set of particles. The physicochemically distinct particles may comprise lipid particles, metal particles, silica particles, or polymer particles. The physicochemically distinct particles may comprise carboxylate particles, poly acrylic acid particles, dextran particles, polystyrene particles, dimethylamine particles, amino particles, silica particles, or N-(3-Trimethoxysilylpropyl)diethylenetriamine particles.

A particle may comprise a polymer. Examples of polymers include any one of or any combination of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers, such as a copolymer of a polyalkylene glycol (e.g., PEG) and a polyester (e.g., PLGA). The polymer may be a lipid-terminated polyalkylene glycol and a polyester, or any other material disclosed in U.S. Pat. No. 9,549,901, the contents of which are herein incorporated by reference in their entirety.

A particle may comprise a lipid. Examples of lipids that can be used to form the particles of the present disclosure include cationic, anionic, and neutrally charged lipids. For example, particles can be made of any one of or any combination of dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidylethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol, or any other material listed in U.S. Pat. No. 9,445,994, which is incorporated herein by reference in its entirety.

Examples of particles of the present disclosure are provided in TABLE 2.

An example of a particle type of the present disclosure may be a carboxylate (Citrate) superparamagnetic iron oxide nanoparticle (SPION), a phenol-formaldehyde coated SPION, a silica-coated SPION, a polystyrene coated SPION, a carboxylated poly(styrene-co-methacrylic acid) coated SPION, a N-(3-Trimethoxysilylpropyl)diethylenetriamine coated SPION, a poly(N-(3-(dimethylamino)propyl) methacrylamide) (PDMAPMA)-coated SPION, a 1,2,4,5-Benzenetetracarboxylic acid coated SPION, a poly(Vinylbenzyltrimethylammonium chloride) (PVBTMAC) coated SPION, a carboxylate, PAA coated SPION, a poly(oligo (ethylene glycol) methyl ether methacrylate) (POEGMA)-coated SPION, a carboxylate microparticle, a polystyrene carboxyl functionalized particle, a carboxylic acid coated particle, a silica particle, a carboxylic acid particle of about 150 nm in diameter, an amino surface microparticle of about 0.4-0.6 µm in diameter, a silica amino functionalized microparticle of about 0.1-0.39 µm in diameter, a Jeffamine surface particle of about 0.1-0.39 µm in diameter, a polystyrene microparticle of about 2.0-2.9 µm in diameter, a silica particle, a carboxylated particle with an original coating of about 50 nm in diameter, a particle coated with a dextran based coating of about 0.13 µm in diameter, or a silica silanol coated particle with low acidity.

Particles that are consistent with the present disclosure can be made and used in methods of forming protein coronas after incubation in a biofluid at a wide range of sizes. A particle of the present disclosure may be a nanoparticle. A nanoparticle of the present disclosure may be from about 10 nm to about 1000 nm in diameter. For example, the nanoparticles disclosed herein can be at least 10 nm, at least 100 nm, at least 200 nm, at least 300 nm, at least 400 nm, at least 500 nm, at least 600 nm, at least 700 nm, at least 800 nm, at least 900 nm, from 10 nm to 50 nm, from 50 nm to 100

TABLE 2

Example particles of the present disclosure

| Batch No. | Type | Particle ID | Description |
| --- | --- | --- | --- |
| S-001-001 | HX-13 | SP-001 | Carboxylate (Citrate) superparamagnetic iron oxide NPs (SPION) |
| S-002-001 | HX-19 | SP-002 | Phenol-formaldehyde coated SPION |
| S-003-001 | HX-20 | SP-003 | Silica-coated superparamagnetic iron oxide NPs (SPION) |
| S-004-001 | HX-31 | SP-004 | Polystyrene coated SPION |
| S-005-001 | HX-38 | SP-005 | Carboxylated Poly(styrene-co-methacrylic acid), P(St-co-MAA) coated SPION |
| S-006-001 | HX-42 | SP-006 | N-(3-Trimethoxysilylpropyl)diethylenetriamine coated SPION |
| S-007-001 | HX-56 | SP-007 | poly(N-(3-(dimethylamino)propyl) methacrylamide) (PDMAPMA)-coated SPION |
| S-008-001 | HX-57 | SP-008 | 1,2,4,5-Benzenetetracarboxylic acid coated SPION |
| S-009-001 | HX-58 | SP-009 | poly(vinylbenzyltrimethylammonium chloride) (PVBTMAC) coated SPION |
| S-010-001 | HX-59 | SP-010 | Carboxylate, PAA coated SPION |
| S-011-001 | HX-86 | SP-011 | poly(oligo(ethylene glycol) methyl ether methacrylate) (POEGMA)-coated SPION |
| P-033-001 | P33 | SP-333 | Carboxylate microparticle, surfactant free |
| P-039-003 | P39 | SP-339 | Polystyrene carboxyl functionalized |
| P-041-001 | P41 | SP-341 | Carboxylic acid |
| P-047-001 | P47 | SP-365 | Silica |
| P-048-001 | P48 | SP-348 | Carboxylic acid, 150 nm |
| P-053-001 | P53 | SP-353 | Amino surface microparticle, 0.4-0.6 µm |
| P-056-001 | P56 | SP-356 | Silica amino functionalized microparticle, 0.1-0.39 µm |
| P-063-001 | P63 | SP-363 | Jeffamine surface, 0.1-0.39 µm |
| P-064-001 | P64 | SP-364 | Polystyrene microparticle, 2.0-2.9 µm |
| P-065-001 | P65 | SP-365 | Silica |
| P-069-001 | P69 | SP-369 | Carboxylated Original coating, 50 nm |
| P-073-001 | P73 | SP-373 | Dextran based coating, 0.13 µm |
| P-074-001 | P74 | SP-374 | Silica Silanol coated with lower acidity | nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm in diameter. A nanoparticle may be less than 1000 nm in diameter.

A particle of the present disclosure may be a microparticle. A microparticle may be a particle that is from about 1 μm to about 1000 μm in diameter. For example, the microparticles disclosed here can be at least 1 μm, at least 10 μm, at least 100 μm, at least 200 μm, at least 300 μm, at least 400 μm, at least 500 μm, at least 600 μm, at least 700 μm, at least 800 μm, at least 900 μm, from 10 μm to 50 μm, from 50 μm to 100 μm, from 100 μm to 150 μm, from 150 μm to 200 μm, from 200 μm to 250 μm, from 250 μm to 300 μm, from 300 μm to 350 μm, from 350 μm to 400 μm, from 400 μm to 450 μm, from 450 μm to 500 μm, from 500 μm to 550 μm, from 550 μm to 600 μm, from 600 μm to 650 μm, from 650 μm to 700 μm, from 700 μm to 750 μm, from 750 μm to 800 μm, from 800 μm to 850 μm, from 850 μm to 900 μm, from 100 μm to 300 μm, from 150 μm to 350 μm, from 200 μm to 400 μm, from 250 μm to 450 μm, from 300 μm to 500 μm, from 350 μm to 550 μm, from 400 μm to 600 μm, from 450 μm to 650 μm, from 500 μm to 700 μm, from 550 μm to 750 μm, from 600 μm to 800 μm, from 650 μm to 850 μm, from 700 μm to 900 μm, or from 10 μm to 900 μm in diameter. A microparticle may be less than 1000 μm in diameter.

The ratio between surface area and mass can be a determinant of a particle's properties. For example, the number and types of biomolecules that a particle adsorbs from a solution may vary with the particle's surface area to mass ratio. The particles disclosed herein can have surface area to mass ratios of 3 to 30 $cm^2/mg$, 5 to 50 $cm^2/mg$, 10 to 60 $cm^2/mg$, 15 to 70 $cm^2/mg$, 20 to 80 $cm^2/mg$, 30 to 100 $cm^2/mg$, 35 to 120 $cm^2/mg$, 40 to 130 $cm^2/mg$, 45 to 150 $cm^2/mg$, 50 to 160 $cm^2/mg$, 60 to 180 $cm^2/mg$, 70 to 200 $cm^2/mg$, 80 to 220 $cm^2/mg$, 90 to 240 $cm^2/mg$, 100 to 270 $cm^2/mg$, 120 to 300 $cm^2/mg$, 200 to 500 $cm^2/mg$, 10 to 300 $cm^2/mg$, 1 to 3000 $cm^2/mg$, 20 to 150 $cm^2/mg$, 25 to 120 $cm^2/mg$, or from 40 to 85 $cm^2/mg$. Small particles (e.g., with diameters of 50 nm or less) can have significantly higher surface area to mass ratios, stemming in part from the higher order dependence on diameter by mass than by surface area. In some cases (e.g., for small particles), the particles can have surface area to mass ratios of 200 to 1000 $cm^2/mg$, 500 to 2000 $cm^2/mg$, 1000 to 4000 $cm^2/mg$, 2000 to 8000 $cm^2/mg$, or 4000 to 10000 $cm^2/mg$. In some cases (e.g., for large particles), the particles can have surface area to mass ratios of 1 to 3 $cm^2/mg$, 0.5 to 2 $cm^2/mg$, 0.25 to 1.5 $cm^2/mg$, or 0.1 to 1 $cm^2/mg$.

In some cases, a plurality of particles (e.g., of a particle panel) used with the methods described herein may have a range of surface area to mass ratios. In some cases, the range of surface area to mass ratios for a plurality of particles is less than 100 $cm^2/mg$, 80 $cm^2/mg$, 60 $cm^2/mg$, 40 $cm^2/mg$, 20 $cm^2/mg$, 10 $cm^2/mg$, 5 $cm^2/mg$, or 2 $cm^2/mg$. In some cases, the surface area to mass ratios for a plurality of particles varies by no more than 40%, 30%, 20%, 10%, 5%, 3%, 2%, or 1% between the particles in the plurality. In some cases, the plurality of particles may comprise at least 2, 3, 4, 5, 6, 7, 8, 9, 10, 12, 15, 20, or more different types of particles.

In some cases, a plurality of particles (e.g., in a particle panel) may have a wider range of surface area to mass ratios. In some cases, the range of surface area to mass ratios for a plurality of particles is greater than 100 $cm^2/mg$, 150 $cm^2/mg$, 200 $cm^2/mg$, 250 $cm^2/mg$, 300 $cm^2/mg$, 400 $cm^2/mg$, 500 $cm^2/mg$, 800 $cm^2/mg$, 1000 $cm^2/mg$, 1200 $cm^2/mg$, 1500 $cm^2/mg$, 2000 $cm^2/mg$, 3000 $cm^2/mg$, 5000 $cm^2/mg$, 7500 $cm^2/mg$, 10000 $cm^2/mg$, or more. In some cases, the surface area to mass ratios for a plurality of particles (e.g., within a panel) can vary by more than 100%, 200%, 300%, 400%, 500%, 1000%, 10000% or more. In some cases, the plurality of particles with a wide range of surface area to mass ratios comprises at least 2, 3, 4, 5, 6, 7, 8, 9, 10, 12, 15, 20, or more different types of particles.

A surface functionality may comprise a polymerizable functional group, a positively or negatively charged functional group, a zwitterionic functional group, an acidic or basic functional group, a polar functional group, or any combination thereof. A surface functionality may comprise carboxyl groups, hydroxyl groups, thiol groups, cyano groups, nitro groups, ammonium groups, alkyl groups, imidazolium groups, sulfonium groups, pyridinium groups, pyrrolidinium groups, phosphonium groups, aminopropyl groups, amine groups, boronic acid groups, N-succinimidyl ester groups, PEG groups, streptavidin, methyl ether groups, triethoxylpropylaminosilane groups, PCP groups, citrate groups, lipoic acid groups, BPEI groups, or any combination thereof. A particle from among the plurality of particles may be selected from the group consisting of: micelles, liposomes, iron oxide particles, silver particles, gold particles, palladium particles, quantum dots, platinum particles, titanium particles, silica particles, metal or inorganic oxide particles, synthetic polymer particles, copolymer particles, terpolymer particles, polymeric particles with metal cores, polymeric particles with metal oxide cores, polystyrene sulfonate particles, polyethylene oxide particles, polyoxyethylene glycol particles, polyethylene imine particles, polylactic acid particles, polycaprolactone particles, polyglycolic acid particles, poly(lactide-co-glycolide polymer particles, cellulose ether polymer particles, polyvinylpyrrolidone particles, polyvinyl acetate particles, polyvinylpyrrolidone-vinyl acetate copolymer particles, polyvinyl alcohol particles, acrylate particles, polyacrylic acid particles, crotonic acid copolymer particles, polyethlene phosphonate particles, polyalkylene particles, carboxy vinyl polymer particles, sodium alginate particles, carrageenan particles, xanthan gum particles, gum acacia particles, Arabic gum particles, guar gum particles, pullulan particles, agar particles, chitin particles, chitosan particles, pectin particles, karaya tum particles, locust bean gum particles, maltodextrin particles, amylose particles, corn starch particles, potato starch particles, rice starch particles, tapioca starch particles, pea starch particles, sweet potato starch particles, barley starch particles, wheat starch particles, hydroxypropylated high amylose starch particles, dextrin particles, levan particles, elsinan particles, gluten particles, collagen particles, whey protein isolate particles, casein particles, milk protein particles, soy protein particles, keratin particles, polyethylene particles, polycarbonate particles, polyanhydride particles, polyhydroxyacid particles, polypropylfumerate particles, polycaprolactone particles, polyamine particles, polyacetal particles, polyether particles, polyester particles, poly(orthoester) particles, polycyanoacrylate particles, polyurethane particles, polyphosphazene particles, polyacrylate particles, polymethacrylate particles, polycyanoacrylate particles, polyurea particles, polyamine particles, polystyrene particles, poly(lysine) particles, chitosan particles, dextran particles, poly(acrylamide) particles, derivatized poly(acrylamide) particles, gelatin particles, starch particles, chitosan particles, dextran particles, gelatin particles, starch particles, poly-β-amino-ester particles, poly(amido amine) particles, poly lactic-co-glycolic acid particles, polyanhydride particles, bioreducible polymer particles, and 2-(3-aminopropylamino)ethanol particles, and any combination thereof.

A plurality of particles (e.g. physicochemically distinct particles) may include one or more particle types selected from the group consisting of carboxylate (Citrate) superparamagnetic iron oxide nanoparticle (SPION), a phenol-formaldehyde coated SPION, a silica-coated SPION, a polystyrene coated SPION, a carboxylated poly(styrene-co-methacrylic acid) coated SPION, a N-(3-Trimethoxysilylpropyl)diethylenetriamine coated SPION, a poly(N-(3-(dimethylamino)propyl) methacrylamide) (PDMAPMA)-coated SPION, a 1,2,4,5-Benzenetetracarboxylic acid coated SPION, a poly(Vinylbenzyltrimethylammonium chloride) (PVBTMAC) coated SPION, a carboxylate, PAA coated SPION, a poly(oligo(ethylene glycol) methyl ether methacrylate) (POEGMA)-coated SPION, a carboxylate microparticle, a polystyrene carboxyl functionalized particle, a carboxylic acid coated particle, a silica particle, a carboxylic acid particle, an amino surface particle, a silica amino functionalized particle, a Jeffamine surface particle, a polystyrene particle, a particle coated with a dextran based coating of about 0.13 µm in diameter, or a silica silanol coated particle.

A plurality of particles (e.g. physicochemically distinct particles) may include one or more particle types selected from the group consisting of carboxylate (Citrate) superparamagnetic iron oxide nanoparticle (SPION), a phenol-formaldehyde coated SPION, a silica-coated SPION, a polystyrene coated SPION, a carboxylated poly(styrene-co-methacrylic acid) coated SPION, a N-(3-Trimethoxysilylpropyl)diethylenetriamine coated SPION, a poly(N-(3-(dimethylamino)propyl) methacrylamide) (PDMAPMA)-coated SPION, a 1,2,4,5-Benzenetetracarboxylic acid coated SPION, a poly(Vinylbenzyltrimethylammonium chloride) (PVBTMAC) coated SPION, a carboxylate, PAA coated SPION, a poly(oligo(ethylene glycol) methyl ether methacrylate) (POEGMA)-coated SPION, a carboxylate microparticle, a polystyrene carboxyl functionalized particle, a carboxylic acid coated particle, a silica particle, a carboxylic acid particle, an amino surface particle, a silica amino functionalized particle, a Jeffamine surface particle, a polystyrene particle, a particle coated with a dextran based coating of about 0.13 µm in diameter, or a silica silanol coated particle.

A plurality of particles (e.g. physicochemically distinct particles) may include one or more particle types selected from the group consisting of silica particles, poly(acrylamide) particles, polyethylene glycol particles, or a combination thereof. One or more of the particles may include a paramagnetic or superparamagnetic core material. Particles may include silica particles. Particles may include poly(acrylamide) particles. Particles may include polyethylene glycol particles.

A plurality of particles may comprise multiple particle types. In some cases, a plurality of particles comprises at least 2 types of particles. In some cases, a plurality of particles comprises at least 3 types of particles. In some cases, a plurality of particles comprises at least 5 types of particles. In some cases, a plurality of particles comprises at least 6 types of particles. In some cases, a plurality of particles comprises at least 8 types of particles. In some cases, a plurality of particles comprises at least 10 types of particles. In some cases, a plurality of particles comprises at least 12 types of particles. In some cases, a plurality of particles comprises at least 15 types of particles. In some cases, a plurality of particles comprises at least 18 types of particles. In some cases, a plurality of particles comprises at least 20 types of particles.

A Particle may comprise layers with distinct properties. A particle may comprise a core with a first set of properties and a shell with a second set of properties. A particle may comprise multiple shells with distinct properties (e.g., a core comprising a first material, an inner shell comprising a second material, and an outer shell comprising a third material). A layer of a particle may comprise a plurality of materials. For example, a layer of a particle may comprise a plurality of polymers. The polymers may be homogeneously interspersed within the layer, may be phase separated, or may be unevenly applied.

In some cases, the one or more physicochemical properties are selected from the group consisting of: composition, size, surface charge, hydrophobicity, hydrophilicity, surface functionality, surface topography, surface curvature, shape, and any combination thereof. In some embodiments, the surface functionality comprises a chemical functionalization. In some embodiments, the small molecule functionalization comprises an amine functionalization, a carboxylate functionalization, a monosaccharide functionalization, an oligosaccharide functionalization, a phosphate sugar functionalization, a sulfate sugar functionalization, an alcohol functionalization, a ether functionalization, an ester functionalization, an amide functionalization, a carbonate functionalization, a carbamate functionalization, a urea functionalization, a benzyl functionalization, a phenyl functionalization, a phenol functionalization, an aniline functionalization, an imidazole functionalization, an indole functionalization, a fluoride functionalization, a chloride functionalization, a bromide functionalization, a sulfide functionalization, a nitro functionalization, a thiol functionalization, a nitrogenous base functionalization, an aminopropyl functionalization, a boronic acid functionalization, an N-succinimidyl ester functionalization, a PEG functionalization, a methyl ether functionalization, a triethoxylpropylaminosilane functionalization, a silicon alkoxide functionalization, a phenol-formaldehyde functionalization, an organosilane functionalization, an ethylene glycol functionalization, a PCP functionalization, a citrate functionalization, a lipoic acid functionalization, or any combination thereof. In some embodiments, the small molecule functionalization comprises a silica functionalized particle, an amine functionalized particle, a silicon alkoxide functionalized particle, a polystyrene functionalized particle, and a saccharide functionalized particle. In some embodiments, the small molecule functionalization comprises an amine functionalization, a phosphate sugar functionalization, a carboxylate functionalization, a silica functionalization, an organosilane functionalization, or any combination thereof. In some embodiments, the small molecule functionalization comprises a silica functionalization, an ethylene glycol functionalization, and an amine functionalization, or any combination thereof.

A particle of the present disclosure may be synthesized, or a particle of the present disclosure may be purchased from a commercial vendor. For example, particles consistent with the present disclosure may be purchased from commercial vendors including Sigma-Aldrich, Life Technologies, Fisher Biosciences, nanoComposix, Nanopartz, Spherotech, and other commercial vendors. A suitable particle of the present disclosure may be purchased from a commercial vendor and further modified, coated, or functionalized.

The present disclosure includes compositions and methods that comprise two or more particles from among differing in at least one physicochemical property. Such compositions and methods may comprise at least 2 to at least 20 particles from among the plurality of particles differ in at least one physicochemical property. Such compositions and methods may comprise at least 3 to at least 6 particles from among the plurality of particles differ in at least one physicochemical property. Such compositions and methods may comprise at least 4 to at least 8 particles from among the plurality of particles differ in at least one physicochemical property. Such compositions and methods may comprise at least 4 to at least 10 particles from among the plurality of particles differ in at least one physicochemical property. Such compositions and methods may comprise at least 5 to at least 12 particles from among the plurality of particles differ in at least one physicochemical property. Such compositions and methods may comprise at least 6 to at least 14 particles from among the plurality of particles differ in at least one physicochemical property. Such compositions and methods may comprise at least 8 to at least 15 particles from among the plurality of particles differ in at least one physicochemical property. Such compositions and methods may comprise at least 10 to at least 20 particles from among the plurality of particles differ in at least one physicochemical property. Such compositions and methods may comprise at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 20 distinct particle types, at least 25 particle types, or at least 30 distinct particle types.

A particle of the present disclosure may be contacted with a biological sample (e.g., a biofluid) to form a biomolecule corona. Upon contacting the complex biological sample, one or more types of particles of a plurality of particles may adsorb 100 or more types of proteins (e.g., in a 100 µl aliquot of a biological sample comprising 100 pM of a type of particle, the about $10^{10}$ particles of the given type collectively may adsorb 100 or more types of proteins). The particle and biomolecule corona may be separated from the biological sample, for example by centrifugation, magnetic separation, filtration, or gravitational separation. The particle types and biomolecule corona may be separated from the biological sample using a number of separation techniques. Non-limiting examples of separation techniques include comprises magnetic separation, column-based separation, filtration, spin column-based separation, centrifugation, ultracentrifugation, density or gradient-based centrifugation, gravitational separation, or any combination thereof. A protein corona analysis may be performed on the separated particle and biomolecule corona. A protein corona analysis may comprise identifying one or more proteins in the biomolecule corona, for example by mass spectrometry. A method may comprise contacting a single particle type (e.g., a particle of a type listed in TABLE 2) to a biological sample. A method may also comprise contacting a plurality of particle types (e.g., a plurality of the particle types provided in TABLE 2) to a biological sample. The plurality of particle types may be combined and contacted to the biological sample in a single sample volume. The plurality of particle types may be sequentially contacted to a biological sample and separated from the biological sample prior to contacting a subsequent particle type to the biological sample. Protein corona analysis of the biomolecule corona may compress the dynamic range of the analysis compared to a total protein analysis method.

Contacting a biological sample with a particle or plurality of particles may comprise adding a defined concentration of particles to the biological sample. Contacting a biological sample with a particle or plurality of particles may comprise adding from 1 pM to 100 nM of particles to the biological sample. Contacting a biological sample with a particle or plurality of particles may comprise adding from 1 pM to 500 pM of particles to the biological sample. Contacting a biological sample with a particle or plurality of particles may comprise adding from 10 pM to 1 nM of particles to the biological sample. Contacting a biological sample with a particle or plurality of particles may comprise adding from 100 pM to 10 nM of particles to the biological sample. Contacting a biological sample with a particle or plurality of particles may comprise adding from 500 pM to 100 nM of particles to the biological sample. Contacting a biological sample with a particle or plurality of particles may comprise adding from 50 µg/ml to 300 µg/ml (particle mass to biological sample volume) of particles to the biological sample. Contacting a biological sample with a particle or plurality of particles may comprise adding from 100 µg/ml to 500 µg/ml of particles to a biological sample. Contacting a biological sample with a particle or plurality of particles may comprise adding from 250 µg/ml to 750 µg/ml of particles to the biological sample. Contacting a biological sample with a particle or plurality of particles may comprise adding from 400 µg/ml to 1 mg/ml of particles to the biological sample. Contacting a biological sample with a particle or plurality of particles may comprise adding from 600 µg/ml to 1.5 mg/ml of particles to the biological sample. Contacting a biological sample with a particle or plurality of particles may comprise adding from 800 µg/ml to 2 mg/ml of particles to the biological sample. Contacting a biological sample with a particle or plurality of particles may comprise adding from 1 mg/ml to 3 mg/ml of particles to the biological sample. Contacting a biological sample with a particle or plurality of particles may comprise adding from 2 mg/ml to 5 mg/ml of particles to the biological sample. Contacting a biological sample with a particle or plurality of particles may comprise adding than 5 mg/ml of particles to the biological sample.

Particles in a plurality of particles may have varying degrees of size and shape uniformity. The standard deviation in diameter for a collection of particles of a particular type may be less than 20%, 10%, 5%, or 2% of the average diameter for the particle type (e.g., less than 2 nm for a particle with an average diameter of 100 nm). This may correspond to a low polydispersity index for a sample comprising a plurality of particles, less than 2, less than 1, less than 0.8, less than 0.6, less than 0.5, less than 0.4, less than 0.3, less than 0.2, less than 0.1, or less than 0.05. Conversely, a plurality of particles may have a high degree of variance in average size and shape. The polydispersity index for a sample comprising a plurality of particles may be greater than 3, greater than 4, greater than 5, greater than 8, greater than 10, greater than 12, greater than 15, or greater than 20. Size and shape uniformity among a plurality of particles can affect the number and types of biomolecules that adsorb to the particles. For some methods, size uniformity (e.g., a low polydispersity index) among particles enables greater enrichment of particular biomolecules, and a stronger correspondence between enriched biomolecule abundance and particle type. For some methods, low size uniformity enables collection of a greater number of types of biomolecules.

Disclosed herein methods that include obtaining a data set comprising proteins detected in biomolecule coronas corresponding to physicochemically distinct particles incubated with a biological sample. The biological sample may include a blood sample that has had red blood cells removed (e.g. a cell-free sample). The physicochemically distinct types of particles yield different biomolecule coronas. The physicochemically distinct types of particles yield different biomarkers. The physicochemically distinct types of particles yield different mass spectral patterns.

Particle Panels

The present disclosure provides compositions and methods of use thereof for assaying a sample for proteins. Compositions described herein include particle panels comprising one or more than one distinct particle types. Particle panels described herein can vary in the number of particle types and the diversity of particle types in a single panel. For example, particles in a panel may vary based on size, polydispersity, shape and morphology, surface charge, surface chemistry and functionalization, and base material. Panels may be incubated with a sample to be analyzed for proteins and protein concentrations. Proteins in the sample adsorb to the surface of the different particle types in the particle panel to form a protein corona. The exact protein and the concentration of protein that adsorbs to a certain particle type in the particle panel may depend on the composition, size, and surface charge of said particle type. Thus, each particle type in a panel may have different protein coronas due to adsorbing a different set of proteins, different concentrations of a particular protein, or a combination thereof. Each particle type in a panel may have mutually exclusive protein coronas or may have overlapping protein coronas. Overlapping protein coronas can overlap in protein identity, in protein concentration, or both.

The present disclosure also provides methods for selecting a particle types for inclusion in a panel depending on the sample type. Particle types included in a panel may be a combination of particles that are optimized for removal of highly abundant proteins. Particle types also consistent for inclusion in a panel are those selected for adsorbing particular proteins of interest. The particles can be nanoparticles. The particles can be microparticles. The particles can be a combination of nanoparticles and microparticles.

The particle panels disclosed herein can be used to identify the number of distinct proteins disclosed herein, and/or any of the specific proteins disclosed herein, over a wide dynamic range. For example, the particle panels disclosed herein comprising distinct particle types, can enrich for proteins in a sample over the entire dynamic range at which proteins are present in a sample (e.g., a plasma sample). In some cases, a particle panel including any number of distinct particle types disclosed herein, enriches proteins over a dynamic range of at least 2 orders of magnitude. In some cases, a particle panel including any number of distinct particle types disclosed herein, enriches proteins over a dynamic range of at least 3 orders of magnitude. In some cases, a particle panel including any number of distinct particle types disclosed herein, enriches proteins over a dynamic range of at least 4 orders of magnitude. In some cases, a particle panel including any number of distinct particle types disclosed herein, enriches proteins over a dynamic range of at least 5 orders of magnitude. In some cases, a particle panel including any number of distinct particle types disclosed herein, enriches proteins over a dynamic range of at least 6 orders of magnitude. In some cases, a particle panel including any number of distinct particle types disclosed herein, enriches proteins over a dynamic range of at least 7 orders of magnitude. In some cases, a particle panel including any number of distinct particle types disclosed herein, enriches proteins over a dynamic range of at least 8 orders of magnitude. In some cases, a particle panel including any number of distinct particle types disclosed herein, enriches proteins over a dynamic range of at least 9 orders of magnitude. In some cases, a particle panel including any number of distinct particle types disclosed herein, enriches proteins over a dynamic range of at least 10 orders of magnitude. In some cases, a particle panel including any number of distinct particle types disclosed herein, enriches proteins over a dynamic range of at least 11 orders of magnitude. In some cases, a particle panel including any number of distinct particle types disclosed herein, enriches proteins over a dynamic range of at least 12 orders of magnitude. In some cases, a particle panel including any number of distinct particle types disclosed herein, enriches proteins over a dynamic range of from 3 to 5 orders of magnitude. In some cases, a particle panel including any number of distinct particle types disclosed herein, enriches proteins over a dynamic range of from 3 to 6 orders of magnitude. In some cases, a particle panel including any number of distinct particle types disclosed herein, enriches proteins over a dynamic range of from 4 to 8 orders of magnitude. In some cases, a particle panel including any number of distinct particle types disclosed herein, enriches proteins over a dynamic range of from 5 to 8 orders of magnitude. In some cases, a particle panel including any number of distinct particle types disclosed herein, enriches proteins over a dynamic range of from 6 to 10 orders of magnitude. In some cases, a particle panel including any number of distinct particle types disclosed herein, enriches proteins over a dynamic range of from 8 to 12 orders of magnitude. For example, a particle panel may collect proteins at mM and a fM concentrations in a sample, thereby enriching proteins over a 12 order of magnitude range.

A particle panel including any number of distinct particle types disclosed herein, enriches a single protein or protein group. In some cases, the single protein or protein group may comprise proteins having different post-translational modifications. For example, a first particle type in the particle panel may enrich a protein or protein group having a first post-translational modification, a second particle type in the particle panel may enrich the same protein or same protein group having a second post-translational modification, and a third particle type in the particle panel may enrich the same protein or same protein group lacking a post-translational modification. In some cases, the particle panel including any number of distinct particle types disclosed herein, enriches a single protein or protein group by binding different domains, sequences, or epitopes of the single protein or protein group. For example, a first particle type in the particle panel may enrich a protein or protein group by binding to a first domain of the protein or protein group, and a second particle type in the particle panel may enrich the same protein or same protein group by binding to a second domain of the protein or protein group.

A particle panel may comprise a combination of particles with silica and polymer surfaces. For example, a particle panel may comprise a SPION coated with a thin layer of silica, a SPION coated with poly(dimethyl aminopropyl methacrylamide) (PDMAPMA), and a SPION coated with poly(ethylene glycol) (PEG). A particle panel consistent with the present disclosure could also comprise two or more particles selected from the group consisting of silica coated SPION, an N-(3-Trimethoxysilylpropyl) diethylenetriamine coated SPION, a PDMAPMA coated SPION, a carboxyl-functionalized polyacrylic acid coated SPION, an amino surface functionalized SPION, a polystyrene carboxyl functionalized SPION, a silica particle, and a dextran coated SPION. A particle panel consistent with the present disclosure may also comprise two or more particles selected from the group consisting of a surfactant free carboxylate microparticle, a carboxyl functionalized polystyrene particle, a silica coated particle, a silica particle, a dextran coated particle, an oleic acid coated particle, a boronated nanopowder coated particle, a PDMAPMA coated particle, a Poly(glycidyl methacrylate-benzylamine) coated particle, and a Poly(N-[3-(Dimethylamino)propyl]methacrylamide-co-[2-(methacryloyloxy)ethyl]dimethyl-(3-sulfopropyl)ammonium hydroxide, P(DMAPMA-co-SBMA) coated particle. A particle panel consistent with the present disclosure may comprise silica-coated particles, N-(3-Trimethoxysilyl-propyl)diethylenetriamine coated particles, poly(N-(3-(dimethylamino)propyl) methacrylamide) (PDMAPMA)-coated particles, phosphate-sugar functionalized polystyrene particles, amine functionalized polystyrene particles, polystyrene carboxyl functionalized particles, ubiquitin functionalized polystyrene particles, dextran coated particles, or any combination thereof.

The particle panels disclosed herein can be used to identifying a number of proteins, peptides, or protein groups using the workflow described herein (MS analysis of distinct biomolecule coronas corresponding to distinct particle types in the particle panel, collectively referred to as the "Proteograph" workflow). Feature intensities, as disclosed herein, are derived from the intensity of a discrete spike ("feature") seen on a plot of mass to charge ratio versus intensity from a mass spectrometry run of a sample. These features can correspond to variably ionized fragments of peptides and/or proteins. Using the data analysis methods described herein, feature intensities can be sorted into protein groups. Protein groups refer to two or more proteins that are identified by a shared peptide sequence. Alternatively, a protein group can refer to one protein that is identified using a unique identifying sequence. For example, if in a sample, a peptide sequence is assayed that is shared between two proteins (Protein 1: XYZZX and Protein 2: XYZYZ), a protein group could be the "XYZ protein group" having two members (protein 1 and protein 2). Alternatively, if the peptide sequence is unique to a single protein (Protein 1), a protein group could be the "ZZX" protein group having one member (Protein 1). Each protein group can be supported by more than one peptide sequence. Protein detected or identified according to the instant disclosure can refer to a distinct protein detected in the sample (e.g., distinct relative other proteins detected using mass spectrometry). Thus, analysis of proteins present in distinct coronas corresponding to the distinct particle types in a particle panel, yields a high number of feature intensities. This number decreases as feature intensities are processed into distinct peptides, further decreases as distinct peptides are processed into distinct proteins, and further decreases as peptides are grouped into protein groups (two or more proteins that share a distinct peptide sequence).

Particle panels disclosed herein for assessing the presence or absence of one or more biomarkers associated with lung cancer (e.g., NSCLC) can have at least 1 distinct particle type, at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 16 distinct particle types, at least 17 distinct particle types, at least 18 distinct particle types, at least 19 distinct particle types, at least 20 distinct particle types, at least 25 distinct particle types, at least 30 distinct particle types, at least 35 distinct particle types, at least 40 distinct particle types, at least 45 distinct particle types, at least 50 distinct particle types, at least 55 distinct particle types, at least 60 distinct particle types, at least 65 distinct particle types, at least 70 distinct particle types, at least 75 distinct particle types, at least 80 distinct particle types, at least 85 distinct particle types, at least 90 distinct particle types, at least 95 distinct particle types, at least 100 distinct particle types, from 1 to 5 distinct particle types, from 5 to 10 distinct particle types, from 10 to 15 distinct particle types, from 15 to 20 distinct particle types, from 20 to 25 distinct particle types, from 25 to 30 distinct particle types, from 30 to 35 distinct particle types, from 35 to 40 distinct particle types, from 40 to 45 distinct particle types, from 45 to 50 distinct particle types, from 50 to 55 distinct particle types, from 55 to 60 distinct particle types, from 60 to 65 distinct particle types, from 65 to 70 distinct particle types, from 70 to 75 distinct particle types, from 75 to 80 distinct particle types, from 80 to 85 distinct particle types, from 85 to 90 distinct particle types, from 90 to 95 distinct particle types, from 95 to 100 distinct particle types, from 1 to 100 distinct particle types, from 20 to 40 distinct particle types, from 5 to 10 distinct particle types, from 3 to 7 distinct particle types, from 2 to 10 distinct particle types, from 6 to 15 distinct particle types, or from 10 to 20 distinct particle types. In particular embodiments, the present disclosure provides a panel size of from 3 to 10 particle types. In particular embodiments, the present disclosure provides a panel size of from 4 to 11 distinct particle types. In particular embodiments, the present disclosure provides a panel size of from 5 to 15 distinct particle types. In particular embodiments, the present disclosure provides a panel size of from 5 to 15 distinct particle types. In particular embodiments, the present disclosure provides a panel size of from 8 to 12 distinct particle types. In particular embodiments, the present disclosure provides a panel size of from 9 to 13 distinct particle types. In particular embodiments, the present disclosure provides a panel size of 10 distinct particle types. The particle types may include nanoparticle types.

A particle panel may be designed to broadly profile a proteome, such as the human plasma proteome. A major challenge in analyzing the human proteome is that more than 99% of mass of the roughly 3500 proteins in human plasma is accounted for by just 20 proteins. Plasma analysis methods are often saturated by these 20 proteins, and provide minimal profiling depth into the remaining proteins. A particle panel of the present disclosure may comprise a combination of particles that facilitates collection of at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 2100, or at least 2200 distinct proteins from a single biological sample. A particle panel of the present disclosure may comprise a combination of particles that facilitates collection of at least 4%, at least 5%, at least 6%, at least 8%, at least 10%, at least 12%, at least 15%, at least 20%, at least 25%, at least 30%, at least 35%, at least 40%, at least 45%, at least 50%, at least 55%, at least 60%, at least 65%, or at least 70% of the types of proteins from a complex biological sample, such as human plasma. This may be achieved by providing a plurality of particles (e.g., as a particle panel) with distinct protein binding profiles. A particle panel may comprise two particles which, upon contact with a biological sample, form protein coronas with fewer than 80%, fewer than 70%, fewer than 60%, fewer than 50%, fewer than 40%, fewer than 30%, fewer than 25%, fewer than 20%, fewer than 15%, or fewer than 10% of proteins in common. In some cases, the biological sample is human plasma.

Figure 12:
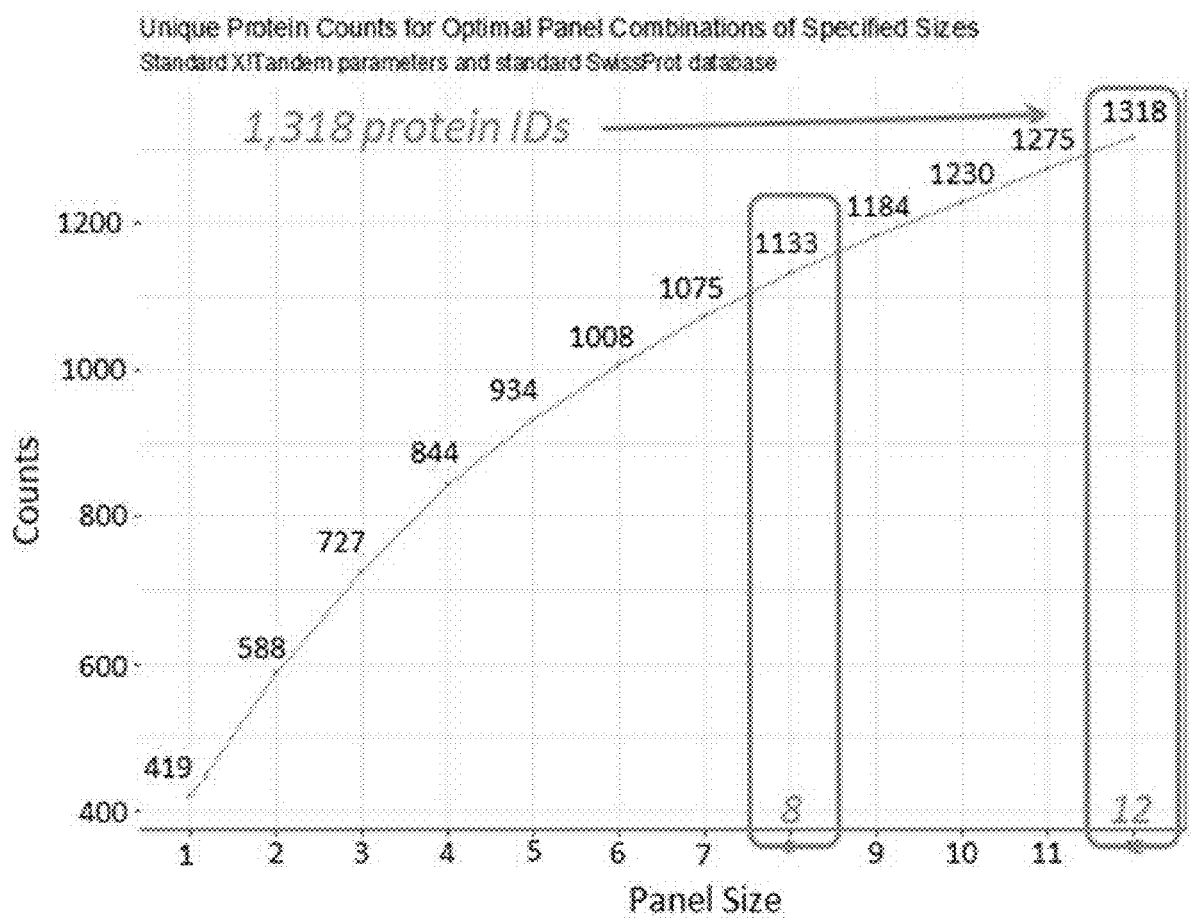
FIG. 12 shows protein counts (e.g. number of proteins identified from corona analysis) for panel sizes ranging from 1 particle type to 12 particle types.

Increasing the number of particle types in a panel can increase the number of proteins that can be identified in a given sample. An example of how increasing panel size may increase the number of identified proteins is shown in FIG. 12, in which a panel size of one particle type identified 419 different proteins, a panel size of two particle types identified 588 different proteins, a panel size of three particle types identified 727 different proteins, a panel size of four particle types identified 844 proteins, a panel size of five particle types identified 934 different proteins, a panel size of six particle types identified 1008 different proteins, a panel size of seven particle types identified 1075 different proteins, a panel size of eight particle types identified 1133 different proteins, a panel size of nine particle types identified 1184 different proteins, a panel size of 10 particle types identified 1230 different proteins, a panel size of 11 particle types identified 1275 different proteins, and a panel size of 12 particle types identified 1318 different proteins.

Biomarker Analysis in Biological Samples

The compositions and methods of use thereof disclosed herein can identify a large number of unique proteins in a biological sample (e.g., a biofluid). Non-limiting examples of biological samples that may be analyzed using the methods (e.g. protein corona analysis) described herein include biofluid samples (e.g., cerebral spinal fluid (CSF), synovial fluid (SF), urine, plasma, serum, tears, semen, whole blood, milk, nipple aspirate, ductal lavage, vaginal fluid, nasal fluid, ear fluid, gastric fluid, pancreatic fluid, trabecular fluid, lung lavage, prostatic fluid, sputum, fecal matter, bronchial lavage, fluid from swabbings, bronchial aspirants, sweat or saliva), fluidized solids (e.g., a tissue homogenate), or samples derived from cell culture. For example, a particle disclosed herein can be incubated with any biological sample disclosed herein to form a protein corona comprising at least 100 unique proteins, at least 120 unique proteins, at least 140 unique proteins, at least 160 unique proteins, at least 180 unique proteins, at least 200 unique proteins, at least 220 unique proteins, at least 240 unique proteins, at least 260 unique proteins, at least 280 unique proteins, at least 300 unique proteins, at least 320 unique proteins, at least 340 unique proteins, at least 360 unique proteins, at least 380 unique proteins, at least 400 unique proteins, at least 420 unique proteins, at least 440 unique proteins, at least 460 unique proteins, at least 480 unique proteins, at least 500 unique proteins, at least 520 unique proteins, at least 540 unique proteins, at least 560 unique proteins, at least 580 unique proteins, at least 600 unique proteins, at least 620 unique proteins, at least 640 unique proteins, at least 660 unique proteins, at least 680 unique proteins, at least 700 unique proteins, at least 720 unique proteins, at least 740 unique proteins, at least 760 unique proteins, at least 780 unique proteins, at least 800 unique proteins, at least 820 unique proteins, at least 840 unique proteins, at least 860 unique proteins, at least 880 unique proteins, at least 900 unique proteins, at least 920 unique proteins, at least 940 unique proteins, at least 960 unique proteins, at least 980 unique proteins, at least 1000 unique proteins, from 100 to 1000 unique proteins, from 150 to 950 unique proteins, from 200 to 900 unique proteins, from 250 to 850 unique proteins, from 300 to 800 unique proteins, from 350 to 750 unique proteins, from 400 to 700 unique proteins, from 450 to 650 unique proteins, from 500 to 600 unique proteins, from 200 to 250 unique proteins, from 250 to 300 unique proteins, from 300 to 350 unique proteins, from 350 to 400 unique proteins, from 400 to 450 unique proteins, from 450 to 500 unique proteins, from 500 to 550 unique proteins, from 550 to 600 unique proteins, from 600 to 650 unique proteins, from 650 to 700 unique proteins, from 700 to 750 unique proteins, from 750 to 800 unique proteins, from 800 to 850 unique proteins, from 850 to 900 unique proteins, from 900 to 950 unique proteins, from 950 to 1000 unique proteins. Similar numbers of proteins may be assessed in some cases without the use of particles, or with an assay method described herein. In some embodiments, several different types of particles can be used, separately or in combination, to identify large numbers of proteins in a particular biological sample. In other words, particles can be multiplexed in order to bind and identify large numbers of proteins in a biological sample.

The compositions and methods disclosed herein can be used to identify various biological states in a particular biological sample. For example, a biological state can refer to an elevated or low level of a particular protein or a set of proteins, or may be evidenced by a ratio between the abundances of two or more biomolecules. In other examples, a biological state can refer to identification of a disease, such as cancer. One or more particle types can be incubated with a biological sample, such as human plasma, allowing for formation of a protein corona. Said protein corona can then be analyzed in order to identify a pattern of proteins. The analysis may comprise gel electrophoresis, mass spectrometry, chromatography, ELISA, immunohistology, or any combination thereof. Analysis of protein corona (e.g., by mass spectrometry or gel electrophoresis) may be referred to as corona analysis. The pattern of proteins can be compared to the same methods carried out on a control sample. Upon comparison of the patterns of proteins, it may be identified that the first sample comprises an elevated level of markers corresponding to a particular type of lung cancer. The particles and methods of use thereof, can thus be used to diagnose a particular disease state.

An assay may comprise protein collection of particles, protein digestion, and mass spectrometric analysis (e.g., MS, LC-MS, LC-MS/MS). The digestion may comprise chemical digestion, such as by cyanogen bromide or 2-Nitro-5-thiocyanatobenzoic acid (NTCB). The digestion may comprise enzymatic digestion, such as by trypsin or pepsin. The digestion may comprise enzymatic digestion by a plurality of proteases. The digestion may comprise a protease selected from among the group consisting of trypsin, chymotrypsin, Glu C, Lys C, elastase, subtilisin, proteinase K, thrombin, factor X, Arg C, papaine, Asp N, thermolysine, pepsin, aspartyl protease, cathepsin D, zinc metalloprotease, glycoprotein endopeptidase, proline, aminopeptidase, prenyl protease, caspase, kex2 endoprotease, or any combination thereof. A digestion method may randomly cleave peptides or may cleave peptides at a specific position or set of positions. An assay may utilize a plurality of digestion methods (e.g., two or more proteases). An assay may comprise splitting a sample into multiple portions, and subjecting the portions to different digestion methods and separate analyses (e.g., separate mass spectrometric analyses). The digestion may cleave peptides at a specific position (e.g., at methionines) or sequence (e.g., glutamate-histidine-glutamate). The digestion may enable similar proteins to be distinguished. For example, an assay may resolve 8 distinct proteins as a single protein group with a first digestion method, and as 8 separate proteins with distinct signals with a second digestion method. The digestion may generate an average peptide fragment length of 8 to 15 amino acids. The digestion may generate an average peptide fragment length of 12 to 18 amino acids. The digestion may generate an average peptide fragment length of 15 to 25 amino acids. The digestion may generate an average peptide fragment length of 20 to 30 amino acids. The digestion may generate an average peptide fragment length of 30 to 50 amino acids.

Various methods of the present disclosure enable measurement over a broad concentration range. Biomolecule analysis methods are often limited to narrow concentration ranges. For example, mass spectrometric proteomic analyses are often limited to 3, 4, or 5 orders of magnitude in concentration. Thus, the presence of relatively high concentration biomolecules (e.g., present at mg/ml concentrations) may mask detection of lower concentration biomolecules, and furthermore may limit the accuracy of low concentration biomolecule quantitation. Methods of the present disclosure may enable detection of molecules spanning at least 5, at least 6, at least 7, at least 8, at least 9, at least 10, at least 11, or at least 12 orders of magnitude in concentration. Thus, a method of the present disclosure may detect and quantitate a relatively high concentration biomolecule and a relatively low concentration biomolecule from a single sample without first depleting biomolecules from the sample. For example, a plasma assay consistent with the present disclosure may simultaneously quantitate albumin (present at around 40 mg/ml) and interleukin 10 (present at around 6 pg/ml) from a single, non-depleted plasma sample, thereby simultaneously detecting two species who concentrations differ by about 10 orders of magnitude.

Dynamic Range

Some methods described herein (e.g. biomolecule corona analysis) may comprise assaying biomolecules in a sample of the present disclosure across a wide dynamic range. The dynamic range of biomolecules assayed in a sample may be a range of biomolecule abundances as measured by an assay method (e.g., mass spectrometry, chromatography, gel electrophoresis, spectroscopy, or immunoassays) for the biomolecules contained within a sample. For example, an assay capable of detecting proteins across a wide dynamic range may be capable of detecting proteins of very low abundance to proteins of very high abundance. The dynamic range of an assay may be directly related to the slope of assay signal intensity as a function of biomolecule abundance. For example, an assay with a low dynamic range may have a low (but positive) slope of the assay signal intensity as a function of biomolecule abundance, e.g., the ratio of the signal detected for a high abundance biomolecule to the ratio of the signal detected for a low abundance biomolecule may be lower for an assay with a low dynamic range than an assay with a high dynamic range. In specific cases, dynamic range may refer to the dynamic range of proteins within a sample or assaying method.

The methods described herein may compress the dynamic range of an assay. The dynamic range of an assay may be compressed relative to another assay if the slope of the assay signal intensity as a function of biomolecule abundance is lower than that of the other assay. For example, a plasma sample assayed using protein corona analysis with mass spectrometry may have a compressed dynamic range compared to a plasma sample assayed using mass spectrometry alone, directly on the sample or compared to provided abundance values for plasma proteins in databases (e.g., the database provided in Keshishian et al., Mol. Cell Proteomics 14, 2375-2393 (2015), also referred to herein as the "Carr database"). The compressed dynamic range may enable the detection of more low abundance biomolecules in a biological sample using biomolecule corona analysis with mass spectrometry than using mass spectrometry alone.

Collecting biomolecules on a particle prior to analysis (e.g., mass spectrometric or ELISA analysis) may compress the dynamic range of the analysis. Two proteins present at a ratio of $10^6$:1 within a biological sample may be differentially adsorbed on a particle and eluted into a solution such that their new ratio is $10^4$:1. Such differential adsorption may enable simultaneous detection of two biomolecules with a concentration difference greater than the dynamic range of an analytical technique. For example, mass spectrometric analysis is often limited to measuring species within a 4-6 order of magnitude concentration range, and thus can be unable to simultaneously detect two biomolecules present at a $10^8$-fold concentration difference. Biomolecule corona-based enrichment of a sample may concentrate a dilute biomolecule (e.g., a first protein) relative to a second biomolecule (e.g., a second protein), thereby enabling simultaneous detection of the two biomolecules with one analytical method. Analogously, particle-based enrichment may enable quantification of a low concentration biomolecule in a sample. The dynamic range over which an analyte may be quantified is often narrower than the dynamic range over which an analyte may be detected. For example, ELISA often covers a dynamic range spanning 2-3 orders of magnitude, while providing accurate concentration quantitation over less than 2 orders of magnitude. Particle-based enrichment may increase the number of biomolecule targets within a desired concentration range, thereby enabling simultaneous quantification of two or more biomolecules present in a biological sample at concentrations outside of the dynamic range for concentration quantitation of an analytical technique.

Accordingly, various methods of the present disclosure comprise detecting two biomolecules present in a biological sample with a concentration difference greater than a dynamic range of a detection method. Many of the biomarker pairs disclosed herein span concentration ranges beyond the limits of detection of biomolecule analysis techniques (e.g., immunostaining or LC-MS/MS), and accordingly can be unidentifiable or unquantifiable without the enrichment-based methods of the present disclosure. In some cases, a method of the present disclosure comprises detecting two biomolecules (e.g., two proteins) at concentrations differing by at least 3-orders of magnitude in a biological sample (e.g., 1 mg/ml and 1 µg/ml, or 50 and 50 nM). In some cases, a method of the present disclosure comprises detecting of two biomolecules (e.g., two proteins) at concentrations differing by at least 4-orders of magnitude in a biological sample (e.g., 1 mg/ml and 100 ng/ml, or 50

μM and 5 nM). In some cases, a method of the present disclosure comprises detecting of two biomolecules (e.g., two proteins) at concentrations differing by at least 5-orders of magnitude in a biological sample (e.g., detection of HBA and NOTUM in human plasma). In some cases, a method of the present disclosure comprises detecting of two biomolecules (e.g., two proteins) at concentrations differing by at least 5-orders of magnitude in a biological sample (e.g., detection of ITIH2 and ANGL6 in human plasma). In some cases, a method of the present disclosure comprises detecting of two biomolecules (e.g., two proteins) at concentrations differing by at least 6-orders of magnitude in a biological sample (e.g., detection of HBA and NOTUM in human plasma). In some cases, a method of the present disclosure comprises detecting of two biomolecules (e.g., two proteins) at concentrations differing by at least 7-orders of magnitude in a biological sample (e.g., detection of ceruloplasmin and RLA2 in human plasma). In some cases, a method of the present disclosure comprises detecting of two biomolecules (e.g., two proteins) at concentrations differing by at least 7-orders of magnitude in a biological sample (e.g., detection of human serum albumin and CAN2 in human plasma). In some cases, a method of the present disclosure comprises detecting of two biomolecules (e.g., two proteins) at concentrations differing by at least 7-orders of magnitude in a biological sample (e.g., detection of human serum albumin and Interleukin 6 in human plasma).

The dynamic range of a proteomic analysis assay may be the ratio of the signal produced by highest abundance proteins (e.g., the highest 10% of proteins by abundance) to the signal produced by the lowest abundance proteins (e.g., the lowest 10% of proteins by abundance). Compressing the dynamic range of a proteomic analysis may comprise decreasing the ratio of the signal produced by the highest abundance proteins to the signal produced by the lowest abundance proteins for a first proteomic analysis assay relative to that of a second proteomic analysis assay. The protein corona analysis assays disclosed herein may compress the dynamic range relative to the dynamic range of a total protein analysis method (e.g., mass spectrometry, gel electrophoresis, or liquid chromatography).

Provided herein are several methods for compressing the dynamic range of a biomolecular analysis assay to facilitate the detection of low abundance biomolecules relative to high abundance biomolecules. For example, a particle type of the present disclosure can be used to serially interrogate a sample. Upon incubation of the particle type in the sample, a biomolecule corona comprising forms on the surface of the particle type. If biomolecules are directly detected in the sample without the use of said particle types, for example by direct mass spectrometric analysis of the sample, the dynamic range may span a wider range of concentrations, or more orders of magnitude, than if the biomolecules are directed on the surface of the particle type. Thus, using the particle types disclosed herein may be used to compress the dynamic range of biomolecules in a sample. Without being limited by theory, this effect may be observed due to more capture of higher affinity, lower abundance biomolecules in the biomolecule corona of the particle type and less capture of lower affinity, higher abundance biomolecules in the biomolecule corona of the particle type.

A dynamic range of a proteomic analysis assay may be the slope of a plot of a protein signal measured by the proteomic analysis assay as a function of total abundance of the protein in the sample. Compressing the dynamic range may comprise decreasing the slope of the plot of a protein signal measured by a proteomic analysis assay as a function of total abundance of the protein in the sample relative to the slope of the plot of a protein signal measured by a second proteomic analysis assay as a function of total abundance of the protein in the sample. The protein corona analysis assays disclosed herein may compress the dynamic range relative to the dynamic range of a total protein analysis method (e.g., mass spectrometry, gel electrophoresis, or liquid chromatography).

Samples and Subjects

The methods described herein may include use of a sample such as a biological sample. For example, a method may include determining one or more biomarker measurements in the sample. The biological sample may be from a subject. The biological sample may include a blood sample that has had red blood cells removed. For example, the biological sample may comprise a plasma sample. The biological sample may comprise a serum sample. The biological sample may comprise blood or a blood constituent.

Samples consistent with the methods disclosed herein of assessing for the presence or absence of one or more biomarkers associated with disease state such as lung cancer (e.g., NSCLC) include biological samples from a subject. The subject may be a human or a non-human animal. Biological samples may be a biofluid. For example, the biofluid may be plasma, serum, CSF, urine, tear, cell lysates, tissue lysates, cell homogenates, tissue homogenates, nipple aspirates, fecal samples, synovial fluid and whole blood, or saliva. Samples can also be non-biological samples, such as water, milk, solvents, or anything homogenized into a fluidic state. Said biological samples can contain a plurality of proteins or proteomic data, which may be analyzed after adsorption of proteins to the surface of the various particle types in a panel and subsequent digestion of protein coronas. Proteomic data can comprise nucleic acids, peptides, or proteins. Any of the samples herein can contain a number of different analytes, which can be analyzed using the compositions and methods disclosed herein. The analytes can be proteins, peptides, small molecules, nucleic acids, metabolites, lipids, or any molecule that could potentially bind or interact with the surface of a particle type.

A biological sample may comprise a biofluid sample such as cerebrospinal fluid (CSF), synovial fluid (SF), urine, plasma, serum, tear, crevicular fluid, semen, whole blood, milk, nipple aspirate, ductal lavage, vaginal fluid, nasal fluid, ear fluid, gastric fluid, pancreatic fluid, trabecular fluid, lung lavage, prostatic fluid, sputum, fecal matter, bronchial lavage, fluid from swabbings, bronchial aspirants, sweat or saliva. A biofluid may be a fluidized solid, for example a tissue homogenate, or a fluid extracted from a biological sample. A biological sample may be, for example, a tissue sample or a fine needle aspiration (FNA) sample. A biological sample may be a cell culture sample. For example, a sample that may be used in the methods disclosed herein can either include cells grow in cell culture or can include acellular material taken from cell cultures. A biofluid may be a fluidized biological sample. For example, a biofluid may be a fluidized cell culture extract. A sample may be extracted from a fluid sample, or a sample may be extracted from a solid sample. For example, a sample may comprise gaseous molecules extracted from a fluidized solid (e.g., a volatile organic compound).

A Method consistent with the present disclosure may comprise collecting (e.g., isolating, enriching, or purifying) a species from biological sample. The species may be a biomolecule (e.g., a protein), a biomacromolecular structure (e.g., a peptide aggregate or a ribosome), a cell, or tissue. The species may be selectively collected from the biological sample. For example, a method may comprise isolating cancer cells from tissue (e.g., as a tissue biopsy) or from a biofluid (e.g., as a liquid biopsy) such as whole blood, plasma, or a buffy coat. The species may be treated prior to analysis. For example, a protein may be reduced and degraded, a nucleic acid may be separated from histones, or a cell may be lysed.

A method may comprise collecting tissue or a cell from a biological sample. The tissue or cell may be collected from a tissue or liquid biological sample. The tissue or cell may be collected directly from a patient. The tissue or cell may be collected from tissue suspected to be cancerous or premalignant. In some cases, the tissue or cell is selected from a biological sample isolated from a patient. The method may comprise identifying a cell or tissue subsection of interest from the biological sample. For example, a method may comprise isolating lung tissue in a transthoracic lung biopsy, identifying potentially cancerous cells through immunohistological staining, and isolating a potentially cancerous cell for further analysis.

A method may comprise parallel analysis of two or more species. The species may be compared to determine a disease state (e.g., the type and stage of a disease) of a sample. The species may originate from a single subject (e.g., a single patient suspected of having early stage non-small cell lung cancer), or from different subjects (e.g., a health patient and a lung cancer patient). The species may comprise a healthy species and a diseased or potentially diseased species. The species may be collected from the same biological sample, for example from a single tissue section, or from different biological samples, for example from separate blood and tissue samples.

Parallel analysis of two or more species may increase the accuracy of a diagnosis. In some cases, multi-species analysis comprises a known healthy species and a suspected or known diseased species (e.g., a cell from healthy tissue and a cell from cancerous tissue). Analysis of the healthy and diseased species may identify the stage of disease of the diseased species. In some cases, the first species may be suspected of comprising a disease and the second species (e.g., a portion of a plasma sample) may comprise potential biomarkers for that disease. In particular cases, the first species may be suspected of comprising a disease and the second species may comprise blood or a portion of a blood sample (e.g., plasma or a buffy coat). For example, a squamous cell may be identified as cancerous through DNA sequencing, and then identified as an early stage cancer cell based on a plasma proteomic profile of the patient.

Disclosed herein are compositions and methods for multi-omic analysis. "Multi-omic(s)" or "multiomic(s)" can refer to an analytical approach for analyzing biomolecules at a large scale, wherein the data sets are multiple omes, such as proteome, genome, transcriptome, lipidome, and metabolome. Non-limiting examples of multi-omic data includes proteomic data, genomic data, lipidomic data, glycomic data, transcriptomic data, or metabolomics data. "Biomolecule" in "biomolecule corona" can refer to any molecule or biological component that can be produced by, or is present in, a biological organism. Non-limiting examples of biomolecules include proteins (protein corona), polypeptides, polysaccharides, a sugar, a lipid, a lipoprotein, a metabolite, an oligonucleotide, a nucleic acid (DNA, RNA, micro RNA, plasmid, single stranded nucleic acid, double stranded nucleic acid), metabolome, as well as small molecules such as primary metabolites, secondary metabolites, and other natural products, or any combination thereof. In some embodiments, the biomolecule is selected from the group of proteins, nucleic acids, lipids, and metabolites.

In some cases, a sample may be depleted prior to biomarker analysis. A sample may be depleted using a commercially available kit. For example, a kit that may be used to deplete a sample may be a spin column-based depletion kit, an albumin depletion kit, an immunodepletion kit, or an abundant protein depletion kit. Non-limiting examples of kits that may be used for sample depletion include a PureProteome™ Human Albumin/Immunoglobulin depletion kit (EMD Millipore Sigma), a ProteoPrep® Immunoaffinity Albumin & IgG Depletion Kit (Millipore Sigma), a Seppro® Protein Depletion kit (Millipore Sigma), Top 12 Abundant Protein Depletion Spin Columns (Pierce), or a Proteome Purify™ Immunodepletion Kit (R&D Systems). Depletion may remove a high concentration biomolecule from a sample. For example, a method may comprise removing albumin from a plasma sample prior to low concentration biomarker analysis. The sample may include depleted plasma.

A sample described or used herein may be from a subject. The subject may be a vertebrate. The subject may be a mammal. The subject may be a human. The subject may be at least 18 years old.

Treatments

Disclosed herein are methods comprising administering a treatment or therapy to a subject in need thereof. Various methods of the present disclosure comprise treating disease states such as cancer in a patient in need thereof, wherein a biomarker such as a peptide from among the peptides listed in TABLE 1 is identified in a sample in the patient. The treatment or therapy may be administered in response to, or based on, the biomarker measurements described herein. The biomarkers may be measured using a method described herein.

A method described herein may include administering a cancer treatment to the subject. A method described herein may include administering a lung disease treatment to the subject. A method described herein may include administering a lung cancer treatment to the subject. A method described herein may include administering a lung disease treatment other than a cancer treatment to the subject. A method described herein may include administering a NSCLC treatment to the subject. A method described herein may include administering a cancer treatment to the subject based on the disease state of the subject. A method described herein may include administering a lung treatment to the subject based on the disease state of the subject. A method described herein may include administering a NSCLC treatment to the subject based on the disease state of the subject.

Disclosed herein are methods of treatment, comprising. The method may include obtaining or receiving a measurement of one or more biomarkers described herein. The measurements may be in a sample from a subject suspected of having a lung cancer. The method may include administering a lung cancer treatment to the subject based on a presence of the one or more biomarkers. The method may include monitoring the subject without providing the lung cancer treatment to the subject based on an absence of the one or more biomarkers. Some embodiments include identifying the subject as having the lung cancer and administering the treatment.

The biomarkers may include peptides. In some cases, at least two peptides, at least three peptides, four peptides, five peptides, eight peptides, ten peptides, fifteen peptides, or twenty peptides from among the peptides listed in TABLE 1 are identified in a sample in the patient. In some cases, the treatment type, duration, dosage, or frequency is determined by the combination or relative abundances of peptides from among the peptides listed in TABLE 1 which are identified in the sample from the patient. In some cases, the treatment efficacy is determined by the combination or relative abundances of peptides from among the peptides listed in TABLE 1 which are identified in the sample from the patient. In some cases, the combination or relative abundances of peptides from among the peptides listed in TABLE 1 diagnoses the patient as having or not having cancer. In some cases, the combination or relative abundances of peptides from among the peptides listed in TABLE 1 diagnoses the type of cancer. In some cases, the combination or relative abundances of peptides from among the peptides listed in TABLE 1 indicates whether a cancer treatment should or should not be administered to the patient. In some cases, the sample is a plasma sample. In some cases, the cancer is a lung cancer such as NSCLC.

Various methods of the present disclosure comprise tracking the progress of a cancer treatment. A method may comprise biomarker detection in a plurality of samples collected from a patient over a period of time. In some cases, a method comprises measuring changes in the level of at least one peptide from among the peptides listed in TABLE 1 in samples from the patient over a period of time to determine whether to discontinue or modify (e.g., adjust administration frequency or dose) a treatment. For example, a method may comprise measuring the concentrations of at least two proteins selected from the group consisting of ANGL6, NOTUM, CILP1, RLA2, and GP1BB in plasma samples collected in biweekly intervals from the patient, and determining when to discontinue a treatment or to start a secondary treatment based on the change in concentrations of the at least two proteins.

In some cases, the treatment comprises chemotherapy. In some cases, the chemotherapy comprises adriamycin, amsacrine, azathioprine, bleomycin, busulfan, capecitabine, carboplatin, chlorambucil, cisplatin, cyclophosphamide, cytarabine, daunorubicin, docetaxel, doxorubicin, epirubicin, etoposide, floxuridine, fludarabine, gemcitabine, ifosfamide, iproplatin, irinotecan, leucovorin, mechlorethamine, melphalan, mercaptopurine, methotrexate, mitomycin, mitoxantrone, nitrosoureas, oxaliplatin, paclitaxel, plicamycin, podophyllotoxin, satraplatin, spiroplatin, teniposide, thiotepa, topotecan, uramustine, vinblastine, vincristine, vindesine, vinorelbine, oxaliplatin, cisplatin, carboplatin, spiroplatin, iproplatin, satraplatin, cyclophosphamide, ifosfamide, chlorambucil, busulfan, melphalan, mechlorethamine, uramustine, thiotepa, nitrosoureas, 5-fluorouracil, azathioprine, 6-mercaptopurine, methotrexate, leucovorin, capecitabine, cytarabine, floxuridine, fludarabine, gemcitabinvincristine, vinblastine, vinorelbine, vindesine, podophyllotoxin, paclita docetaxel, irinotecan, topotecan, amsacrine, etoposide, teniposide, doxorubicin, adriamycin, daunorubicin, epirubicin, actinomycin, bleomycin, mitomycin, mitoxantrone, plicamycin or any combination thereof. In some cases, the treatment comprises an immunotherapy. In some cases, the treatment comprises hormone therapy. In some cases, the treatment comprises monoclonal antibody treatment. In some cases, the treatment comprises an mTOR inhibitor. In some cases, the treatment comprises a stem cell transplant. In some cases, the treatment comprises radiation therapy. In some cases, the treatment comprises gene therapy. In some cases, the treatment comprises chimeric antigen receptor (CAR)-T cell or transgenic T cell administration. In some cases, the treatment comprises resection surgery. For example, a CT scan may identify adenocarcinoma tumors in a patient, and analysis of a protein selected from the group consisting of ANGL6, NOTUM, CILP1, RLA2, and GP1BB from a blood sample from the patient may determine that the tumors are malignant, and therefore that removing the tumors is likely to lead to a favorable outcome.

In some cases, the treatment includes a cancer treatment. In some cases, the treatment includes multiple cancer treatments. Examples of cancer treatments include: Examples of anti-cancer agents include Abemaciclib, Abiraterone Acetate, Abraxane (Paclitaxel Albumin-stabilized Nanoparticle Formulation), ABVD, ABVE, ABVE-PC, AC, Acalabrutinib, AC-T, Actemra (Tocilizumab), Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alpelisib, Alunbrig (Brigatinib), Ameluz (Aminolevulinic Acid Hydrochloride), Amifostine, Aminolevulinic Acid Hydrochloride, Anastrozole, Apalutamide, Aprepitant, Aranesp (Darbepoetin Alfa), Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Asparlas (Calaspargase Pegolmknl), Atezolizumab, Avapritinib, Avastin (Bevacizumab), Avelumab, Axicabtagene Ciloleucel, Axitinib, Ayvakit (Avapritinib), Azacitidine, Azedra (Iobenguane I 131), Balversa (Erdafitinib), Bavencio (Avelumab), BEACOPP, Belantamab Mafodotin-blmf, Beleodaq (Belinostat), Belinostat, Bendamustine Hydrochloride, Bendeka (Bendamustine Hydrochloride), BEP, Besponsa (Inotuzumab Ozogamicin), Bevacizumab, Bexarotene, Bicalutamide, BiCNU (Carmustine), Binimetinib, Blenrep (Belantamab Mafodotin-blmf), Bleomycin Sulfate, Blinatumomab, Blincyto (Blinatumomab), Bortezomib, Bosulif (Bosutinib), Bosutinib, Braftovi (Encorafenib), Brentuximab Vedotin, Brexucabtagene Autoleucel, Brigatinib, Brukinsa (Zanubrutinib), BuMel, Busulfan, Busulfex (Busulfan), Cabazitaxel, Cablivi (Caplacizumab-yhdp), Cabometyx (Cabozantinib-S-Malate), Cabozantinib-S-Malate, CAF, Calaspargase Pegolmknl, Calquence (Acalabrutinib), Campath (Alemtuzumab), Camptosar (Irinotecan Hydrochloride), Capecitabine, Caplacizumab-yhdp, Capmatinib Hydrochloride, CAPDX, Carac (Fluorouracil-Topical), Carboplatin, CARBOPLATIN-TAXOL, Carfilzomib, Carmustine, Carmustine Implant, Casodex (Bicalutamide), CEM, Cemiplimab-rwlc, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clofarabine, Clolar (Clofarabine), CMF, Cobimetinib Fumarate, Cometriq (Cabozantinib-S-Malate), Copanlisib Hydrochloride, COPDAC, Copiktra (Duvelisib), COPP, COPP-ABV, Cosmegen (Dactinomycin), Cotellic (Cobimetinib Fumarate), Crizotinib, CVP, Cyclophosphamide, Cyramza (Ramucirumab), Cytarabine, Dabrafenib Mesylate, Dacarbazine, Dacogen (Decitabine), Dacomitinib, Dactinomycin, Daratumumab, Daratumumab and Hyaluronidase-fihj, Darbepoetin Alfa, Darolutamide, Darzalex (Daratumumab), Darzalex Faspro (Daratumumab and Hyaluronidase-fihj), Dasatinib, Daunorubicin Hydrochloride, Daunorubicin Hydrochloride and Cytarabine Liposome, Daurismo (Glasdegib Maleate), Decitabine, Decitabine and Cedazuridine, Defibrotide Sodium, Defitelio (Defibrotide Sodium), Degarelix, Denileukin Diftitox, Denosumab, Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Durvalumab, Duvelisib, Efudex (Fluorouracil-Topical), Eligard (Leuprolide Acetate), Elitek (Rasburicase), Ellence (Epirubicin Hydrochloride), Elotuzumab, Eloxatin (Oxaliplatin), Eltrombopag Olamine, Elzonris (Tagraxofusp-erzs), Emapalumab-lzsg, Emend (Aprepitant), Empliciti (Elotuzumab), Enasidenib Mesylate, Encorafenib, Enfortumab Vedotin-ejfv, Enhertu (Fam-Trastuzumab Deruxtecan-nxki), Entrectinib, Enzalutamide, Epirubicin Hydrochloride, EPOCH, Epoetin Alfa, Epogen (Epoetin Alfa), Erbitux (Cetuximab), Erdafitinib, Eribulin Mesylate, Erivedge (Vismodegib), Erleada (Apalutamide), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Everolimus, Evista (Raloxifene Hydrochloride), Evomela (Melphalan Hydrochloride), Exemestane, 5-FU (Fluorouracil Injection), 5-FU (Fluorouracil-Topical), Fam-Trastuzumab Deruxtecan-nxki, Fareston (Toremifene), Farydak (Panobinostat), Faslodex (Fulvestrant), FEC, Fedratinib Hydrochloride, Femara (Letrozole), Filgrastim, Firmagon (Degarelix), Fludarabine Phosphate, Fluoroplex (Fluorouracil-Topical), Fluorouracil Injection, Fluorouracil-Topical, Flutamide, FOLFIRI, FOLFIRI-BEVACIZUMAB, FOLFIRI-CETUXIMAB, FOLFIRINOX, FOLFOX, Folotyn (Pralatrexate), Fostamatinib Disodium, Fulphila (Pegfilgrastim), FU-LV, Fulvestrant, Gamifant (Emapalumab-lzsg), Gardasil (Recombinant HPV Quadrivalent Vaccine), Gardasil 9 (Recombinant HPV Nonavalent Vaccine), Gavreto (Pralsetinib), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gilteritinib Fumarate, Glasdegib Maleate, Gleevec (Imatinib Mesylate), Gliadel Wafer (Carmustine Implant), Glucarpidase, Goserelin Acetate, Granisetron, Granisetron Hydrochloride, Granix (Filgrastim), Halaven (Eribulin Mesylate), Hemangeol (Propranolol Hydrochloride), Herceptin Hylecta (Trastuzumab and Hyaluronidase-oysk), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin PFS (Idarubicin Hydrochloride), Idarubicin Hydrochloride, Idelalisib, Idhifa (Enasidenib Mesylate), Ifex (Ifosfamide), Ifosfamide, IL-2 (Aldesleukin), Imatinib Mesylate, Imbruvica (Ibrutinib), Imfinzi (Durvalumab), Imiquimod, Imlygic (Talimogene Laherparepvec), Infugem (Gemcitabine Hydrochloride), Inlyta (Axitinib), Inotuzumab Ozogamicin, Inqovi (Decitabine and Cedazuridine), Inrebic (Fedratinib Hydrochloride), Interferon Alfa-2b, Recombinant, Interleukin-2 (Aldesleukin), Intron A (Recombinant Interferon Alfa-2b), Iobenguane I 131, Ipilimumab, Iressa (Gefitinib), Irinotecan Hydrochloride, Irinotecan Hydrochloride Liposome, Isatuximab-irfc, Istodax (Romidepsin), Ivosidenib, Ixabepilone, Ixazomib Citrate, Ixempra (Ixabepilone), Jakafi (Ruxolitinib Phosphate), JEB, Jelmyto (Mitomycin), Jevtana (Cabazitaxel), Kadcyla (Ado-Trastuzumab Emtansine), Kepivance (Palifermin), Keytruda (Pembrolizumab), Kisqali (Ribociclib), Koselugo (Selumetinib Sulfate), Kymriah (Tisagenlecleucel), Kyprolis (Carfilzomib), Lanreotide Acetate, Lapatinib Ditosylate, Larotrectinib Sulfate, Lenvatinib Mesylate, Lenvima (Lenvatinib Mesylate), Letrozole, Leucovorin Calcium, Leukeran (Chlorambucil), Leuprolide Acetate, Levulan Kerastik (Aminolevulinic Acid Hydrochloride), Libtayo (Cemiplimab-rwlc), Lomustine, Lonsurf (Trifluridine and Tipiracil Hydrochloride), Lorbrena (Lorlatinib), Lorlatinib, Lumoxiti (Moxetumomab Pasudotox-tdfk), Lupron Depot (Leuprolide Acetate), Lurbinectedin, Luspatercept-aamt, Lutathera (Lutetium Lu 177-Dotatate), Lutetium (Lu 177-Dotatate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Mektovi (Binimetinib), Melphalan, Melphalan Hydrochloride, Mercaptopurine, Mesna, Mesnex (Mesna), Methotrexate Sodium, Methylnaltrexone Bromide, Midostaurin, Mitomycin, Mitoxantrone Hydrochloride, Mogamulizumab-kpkc, Monjuvi (Tafasitamab-cxix), Moxetumomab Pasudotox-tdfk, Mozobil (Plerixafor), MVAC, Mvasi (Bevacizumab), Myleran (Busulfan), Mylotarg (Gemtuzumab Ozogamicin), Nanoparticle Paclitaxel (Paclitaxel Albumin-stabilized Nanoparticle Formulation), Necitumumab, Nelarabine, Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nplate (Romiplostim), Nubeqa (Darolutamide), Nyvepria (Pegfilgrastim), Obinutuzumab, Odomzo (Sonidegib), OEPA, Ofatumumab, OFF, Olaparib, Omacetaxine Mepesuccinate, Oncaspar (Pegaspargase), Ondansetron Hydrochloride, Onivyde (Irinotecan Hydrochloride Liposome), Ontak (Denileukin Diftitox), Onureg (Azacitidine), Opdivo (Nivolumab), OPPA, Osimertinib Mesylate, Oxaliplatin, Paclitaxel, Paclitaxel Albumin-stabilized Nanoparticle Formulation, PAD, Padcev (Enfortumab Vedotin-ejfv), Palbociclib, Palifermin, Palonosetron Hydrochloride, Palonosetron Hydrochloride and Netupitant, Pamidronate Disodium, Panitumumab, Panobinostat, Pazopanib Hydrochloride, PCV, PEB, Pegaspargase, Pegfilgrastim, Peginterferon Alfa-2b, PEG-Intron (Peginterferon Alfa-2b), Pemazyre (Pemigatinib), Pembrolizumab, Pemetrexed Disodium, Pemigatinib, Perjeta (Pertuzumab), Pertuzumab, Pertuzumab, Trastuzumab, and Hyaluronidase-zzxf, Pexidartinib Hydrochloride, Phesgo (Pertuzumab, Trastuzumab, and Hyaluronidase-zzxf), Piqray (Alpelisib), Plerixafor, Polatuzumab Vedotin-piiq, Polivy (Polatuzumab Vedotin-piiq), Ponatinib Hydrochloride, Portrazza (Necitumumab), Poteligeo (Mogamulizumab-kpkc), Pralatrexate, Pralsetinib, Prednisone, Procarbazine Hydrochloride, Procrit (Epoetin Alfa), Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Qinlock (Ripretinib), Radium 223 Dichloride, Raloxifene Hydrochloride, Ramucirumab, Rasburicase, Ravulizumab-cwvz, Reblozyl (Luspatercept-aamt), R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Retacrit (Epoetin Alfa), Retevmo (Selpercatinib), Ribociclib, R-ICE, Ripretinib, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rozlytrek (Entrectinib), Rubidomycin (Daunorubicin Hydrochloride), Rubraca (Rucaparib Camsylate), Rucaparib Camsylate, Ruxolitinib Phosphate, Rydapt (Midostaurin), Sacituzumab Govitecan-hziy, Sancuso (Granisetron), Sarclisa (Isatuximab-irfc), Sclerosol Intrapleural Aerosol (Talc), Selinexor, Selpercatinib, Selumetinib Sulfate, Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sustol (Granisetron), Sutent (Sunitinib Malate), Sylatron (Peginterferon Alfa-2b), Sylvant (Siltuximab), Synribo (Omacetaxine Mepesuccinate), Tabloid (Thioguanine), Tabrecta (Capmatinib Hydrochloride), TAC, Tafasitamab-cxix, Tafinlar (Dabrafenib Mesylate), Tagraxofusp-erzs, Tagrisso (Osimertinib Mesylate), Talazoparib Tosylate, Talc, Talimogene Laherparepvec, Talzenna (Talazoparib Tosylate), Tamoxifen Citrate, Tarceva (Erlotinib Hydrochloride), Targretin (Bexarotene), Tasigna (Nilotinib), Tavalisse (Fostamatinib Disodium), Taxotere (Docetaxel), Tazemetostat Hydrobromide, Tazverik (Tazemetostat Hydrobromide), Tecartus (Brexucabtagene Autoleucel), Tecentriq (Atezolizumab), Temodar (Temozolomide), Temozolomide, Temsirolimus, Thioguanine, Thiotepa, Tibsovo (Ivosidenib), Tisagenlecleucel, Tocilizumab, Tolak (Fluorouracil-Topical), Topotecan Hydrochloride, Toremifene, Torisel (Temsirolimus), Totect (Dexrazoxane Hydrochloride), TPF, Trabectedin, Trametinib, Trastuzumab, Trastuzumab and Hyaluronidase-oysk, Treanda (Bendamustine Hydrochloride), Trexall (Methotrexate Sodium), Trifluridine and Tipiracil Hydrochloride, Trisenox (Arsenic Trioxide), Trodelvy (Sacituzumab Govitecan-hziy), Truxima (Rituximab), Tucatinib, Tukysa (Tucatinib), Turalio (Pexidartinib Hydrochloride), Tykerb (Lapatinib Ditosylate), Ultomiris (Ravulizumab-cwvz), Undencyca (Pegfilgrastim), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VeIP, Velcade (Bortezomib), Vemurafenib, Venclexta (Venetoclax), Venetoclax, Verzenio (Abemaciclib), Vidaza (Azacitidine), Vinblastine Sulfate, Vincristine Sulfate, Vincristine Sulfate Liposome, Vinorelbine Tartrate, VIP, Vismodegib, Vistogard (Uridine Triacetate), Vitrakvi (Larotrectinib Sulfate), Vizimpro (Dacomitinib), Voraxaze (Glucarpidase), Vorinostat, Votrient (Pazopanib Hydrochloride), Vyxeos (Daunorubicin Hydrochloride and Cytarabine Liposome), Xalkori (Crizotinib), Xatmep (Methotrexate Sodium), Xeloda (Capecitabine), XELIRI, XELOX, Xgeva (Denosumab), Xofigo (Radium 223 Dichloride), Xospata (Gilteritinib Fumarate), Xpovio (Selinexor), Xtandi (Enzalutamide), Yervoy (Ipilimumab), Yescarta (Axicabtagene Ciloleucel), Yondelis (Trabectedin), Yonsa (Abiraterone Acetate), Zaltrap (Ziv-Aflibercept), Zanubrutinib, Zarxio (Filgrastim), Zejula (Niraparib Tosylate Monohydrate), Zelboraf (Vemurafenib), Zepzelca (Lurbinectedin), Zevalin (Ibritumomab Tiuxetan), Ziextenzo (Pegfilgrastim), Zinecard (Dexrazoxane Hydrochloride), Zirabev (Bevcizumab), Ziv-Aflibercept, Zofran (Ondansetron Hydrochloride), Zoladex (Goserelin Acetate), Zoledronic Acid, Zolinza (Vorinostat), Zometa (Zoledronic Acid), Zyclara (Imiquimod), Zydelig (Idelalisib), Zykadia (Ceritinib), or Zytiga (Abiraterone Acetate).

Kits

Various aspects of the present disclosure provide kits for detecting (e.g., quantifying) biomarkers disclosed herein. A kit may comprise a reagent for detecting a peptide from TABLE 1, such as an anti-SAA2 antibody. A kit may comprise multiple reagents for detecting multiple peptides from TABLE 1. A kit may comprise reagents for an ELISA assay. A kit may also comprise a reagent for detecting a biomolecule not useful as a biomarker for a particular cancer. For example, a kit may comprise reagents for quantifying ANTR1 and ANTR2 in a biological sample, as well as a reagent for quantifying ceruloplasmin, such that the ANTR1- and ANTR2-specific reagents generate cancer-specific information from the sample, and the ceruloplasmin-specific agent is configured to serve as a calibration standard or control. A kit may comprise reagents for detecting at least one peptide from TABLE 1, at least two peptides from TABLE 1, at least three peptides from TABLE 1, at least four peptides from TABLE 1, at least five peptides from TABLE 1, at least six peptides from TABLE 1, at least eight peptides from TABLE 1, at least ten peptides from TABLE 1, at least twelve peptides from TABLE 1, at least fifteen peptides from TABLE 1, at least twenty peptides from TABLE 1, at least twenty five peptides from TABLE 1, at least thirty peptides from TABLE 1, or at least forty peptides from TABLE 1, optionally along with a reagent or plurality of reagents for detecting at least one peptide not listed in TABLE 1. For example, a kit may comprise ELISA reagents for detecting at least one, at least two, at least three, at least four, at least five, at least six, at least eight, at least ten, at least twelve, at least fifteen, at least twenty, at least twenty five, at least thirty, or at least forty peptides from TABLE 1, and optionally for at least one peptide not listed in TABLE 1.

A kit may comprise a plurality of antibodies which target at least one, at least two, at least three, at least four, at least five, at least six, at least eight, at least ten, at least twelve, at least fifteen, at least twenty, at least twenty five, at least thirty, or at least forty peptides from TABLE 1, and optionally for at least one peptide not listed in TABLE 1.

A kit may comprise a particle or a particle panel. Particles from the particle panel may be provided collectively (e.g., as a mixture) or separately. For example, a kit may comprise a particle panel with 8 particle-types, each particle-type provided in a separate well within a 96-well plate. A kit may comprise a particle panel comprising at least one, at least two, at least three, at least four, at least five, at least six, at least eight, at least ten, at least twelve, or at least fifteen particles from among the particles in TABLE 2. A kit may comprise multiple compositions comprising the same particle or plurality of particles in different conditions (e.g., mixed with or suspended in different buffers or solutions) or in different amounts. For example, a well plate may comprise a set of wells with 20 μg of a particle, a set of wells with 40 μg of the particle, and a set of wells with 80 μg of the particle. A kit may comprise a buffer for suspending a particle, eluting a biomolecule from a particle, or for washing a particle. A kit may comprise a reagent for chemically modifying (e.g., a reductant) or digesting (e.g., a protease) a protein. A kit may comprise a plurality of reagents for enriching a subset of proteins from a sample (e.g., a particle panel) and preparing the subset of proteins for mass spectrometric analysis (e.g., trypsin, a buffer, an alkylating reagent, and a reductant). A kit may comprise a reagent for lysing a virus or a cell (e.g., a lysis buffer).

A kit may be configured for multiplexed analysis. A kit may comprise a plurality of reagents, and may be configured to interrogate multiple portions of a biological sample under different conditions or with different reagents. A kit may comprise a plurality of partitions, such as a plurality of wells within a well plate or a plurality of Eppendorf tubes. A partition may be pre-packaged with a reagent. For example, a kit may comprise a well plate with a plurality of wells containing different affinity reagents specific for different peptides from TABLE 1.

A kit may be compatible for use with a commercial instrument. For example, a kit may comprise a well plate configured for fluorescence measurements in a microplate reader, or may comprise a sample vial compatible with a commercial mass spectrometer.

Systems

Figure 13:
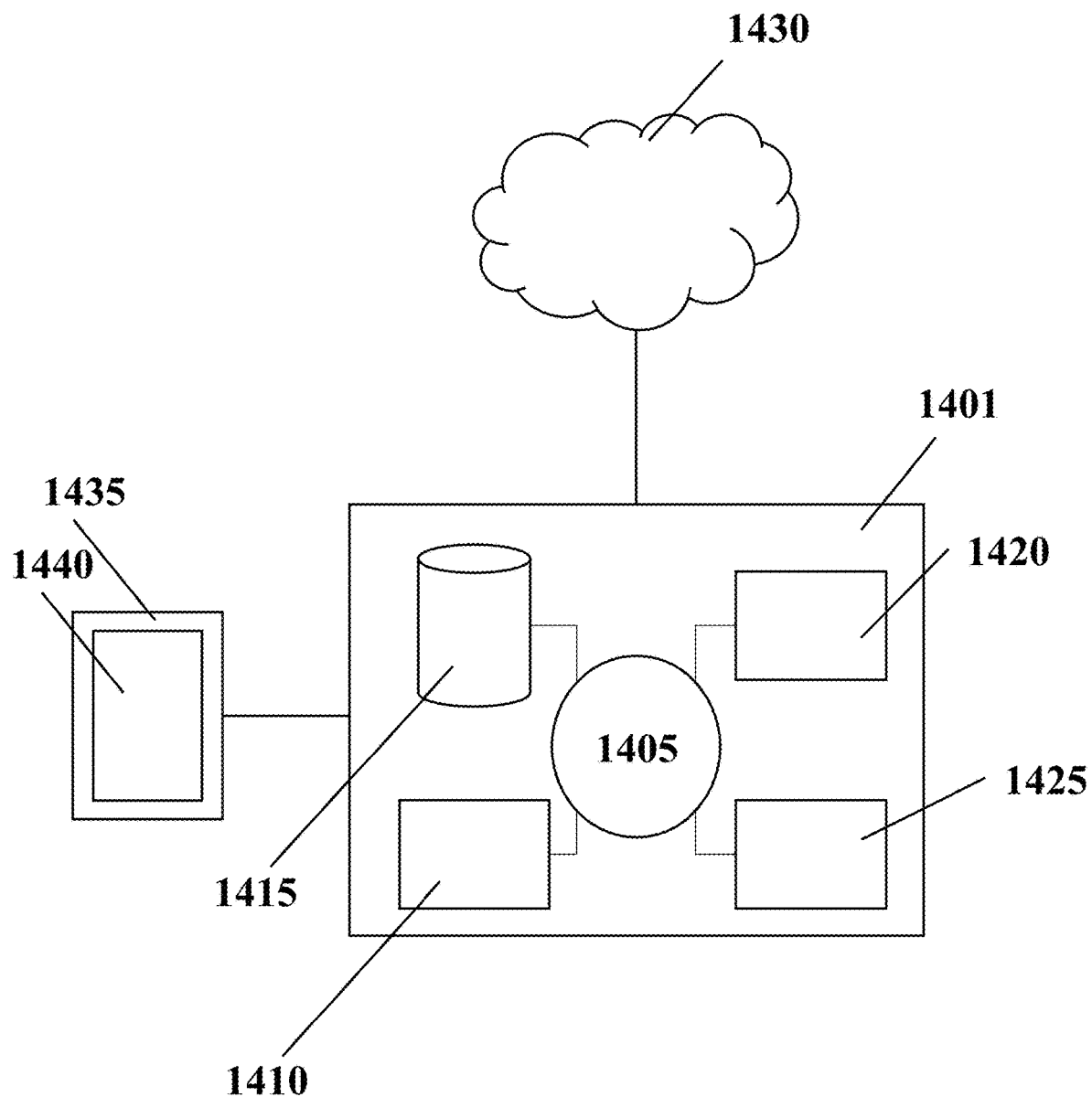
FIG. 13 shows a computer system that is programmed or otherwise configured to implement methods provided herein.

The present disclosure provides systems that may implement a method described herein. The system may include a computer control system programmed to implement methods of the disclosure. FIG. 13 shows a computer system that is programmed or otherwise configured to implement methods provided herein. The computer system 1401 can regulate various aspects of the assays disclosed herein, which are capable of being automated (e.g., movement of any of the reagents disclosed herein on a substrate). The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440 for providing, for example a readout of the proteins identified using the methods disclosed herein. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1405.

A system such as a computer system may be adapted to implement a method described herein. For example, a system described herein may implement a statistical, classification, or machine learning method described herein. Data collected from a sensor array can be used to train a machine learning algorithm, for example an algorithm that receives assay measurements from a subject and outputs specific assay results from each subject. Before training the algorithm, raw data from the array can be first denoised to reduce variability in individual variables.

The system may include a central computer server that is programmed to implement the methods described herein. The server may include a central processing unit (CPU, also "processor") which can be a single core processor, a multi core processor, or plurality of processors for parallel processing. The server also may include memory (e.g., random access memory, read-only memory, flash memory); electronic storage unit (e.g. hard disk); communications interface (e.g., network adaptor) for communicating with one or more other systems; and peripheral devices which may include cache, other memory, data storage, and/or electronic display adaptors. The memory, storage unit, interface, and peripheral devices may be in communication with the processor through a communications bus (solid lines), such as a motherboard. The storage unit can be a data storage unit for storing data. The server is operatively coupled to a computer network ("network") with the aid of the communications interface. The network can be the Internet, an intranet and/or an extranet, an intranet and/or extranet that is in communication with the Internet, a telecommunication or data network. The network in some cases, with the aid of the server, can implement a peer-to-peer network, which may enable devices coupled to the server to behave as a client or a server.

The storage unit can store files, such as subject reports, and/or communications with the data about individuals, or any aspect of data associated with the present disclosure.

The computer server can communicate with one or more remote computer systems through the network. The one or more remote computer systems may be, for example, personal computers, laptops, tablets, telephones, Smart phones, or personal digital assistants.

In some applications the computer system includes a single server. In other situations, the system includes multiple servers in communication with one another through an intranet, extranet and/or the internet.

The server can be adapted to store measurement data or a database as provided herein, patient information from the subject, such as, for example, medical history, family history, demographic data and/or other clinical or personal information of potential relevance to a particular application. Such information can be stored on the storage unit or the server and such data can be transmitted through a network.

Methods as described herein can be implemented by way of machine (or computer processor) executable code (or software) stored on an electronic storage location of the server, such as, for example, on the memory, or electronic storage unit. During use, the code can be executed by the processor. In some cases, the code can be retrieved from the storage unit and stored on the memory for ready access by the processor. In some situations, the electronic storage unit can be precluded, and machine-executable instructions are stored on memory. Alternatively, the code can be executed on a second computer system.

Aspects of the systems and methods provided herein, such as the server, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

The computer systems described herein may comprise computer-executable code for performing any of the algorithms or algorithms-based methods described herein. In some applications the algorithms described herein will make use of a memory unit that is comprised of at least one database.

Data relating to the present disclosure can be transmitted over a network or connections for reception and/or review by a receiver. The receiver can be but is not limited to the subject to whom the report pertains; or to a caregiver thereof, e.g., a health care provider, manager, other health care professional, or other caretaker; a person or entity that performed and/or ordered the analysis. The receiver can also be a local or remote system for storing such reports (e.g. servers or other systems of a "cloud computing" architecture). In one embodiment, a computer-readable medium includes a medium suitable for transmission of a result of an analysis of a biological sample using the methods described herein.

Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide nontransitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

A system may include a communication interface that receives biomolecule data from a sample from a subject comprising the biomolecules. The sample may have been exposed to a plurality of particles having physicochemically distinct properties. The biomolecule data may be received over a communication network.

A system may include a communication interface that receives biomarker data from a sample from a subject suspected of having a non-small cell lung cancer (NSCLC). The biomarkers may comprise one or more biomarkers described herein.

A system may include a computer in communication with the communication interface. The computer may include a computer processor. The computer may include a computer readable medium comprising machine-executable code that, upon execution by the computer processor, implements a method. The method may include (i) receiving, over the communication network, the biomolecule data, (ii) combining the biomolecule data to generate a biomolecule fingerprint for the sample, and/or (iii) assigning a label to the biomolecule fingerprint. The label may correspond to a disease state described herein. The label may correspond to a presence of absence of a non-small cell lung cancer (NSCLC) in the subject. A system may include an output device configured to output information regarding the label.

A system may include a communication interface that receives biomarker data from a sample from a subject suspected of having a cancer or lung cancer such as a non-small cell lung cancer (NSCLC). The sample may include one or more biomarkers described herein. The biomolecule data may be received over a communication network.

A system may include an assay device that generates biomolecule data. The assay device may generate the biomolecule data by performing at least one aspect of an assay comprising mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining. In some cases, assay device transmits the biomolecule data over the communication network. The assay device may include a mass spectrometer. The biomolecule data may include comprise mass spectra. The assay device may include a chromatography device (e.g. a liquid chromatography device, or a high-performance liquid chromatography device). The biomolecule data may include comprise chromatography data. The assay device may include a lateral flow assay device. The biomolecule data may include comprise lateral flow assay data. The assay device may include an immunoassay device (e.g. an enzyme-linked immunosorbent assay device, a western blot device, a dot blot device, or an immunostaining device). The biomolecule data may include comprise immunoassay data such as an image or a blot.

EXAMPLES

The following examples are illustrative and non-limiting to the scope of the devices, systems, fluidic devices, kits, and methods described herein.

Example 1

Non-Small Cell Lung Cancer (NSCLC) Study

This example illustrates a non-small cell lung cancer (NSCLC) study.

Design and Collection of Samples, Collection of Data. Data was collected at multiple sites for the following three arms: NSCLC (all stages), pulmonary co-morbidity, and healthy controls. For sample selection, inclusion and exclusion criteria was as follows: 1) Greater than or equal to 18 years if age, informed consent, able to donate 50 mL; 2) No prior history of any cancer; 3) For NSCLC subjects, pathology-confirmed diagnosis and no prior therapy for the newly diagnosed cancer; 4) For pulmonary co-morbidity controls, subjects have one of more of the following: COPD, emphysema, cardiovascular disease, hypertension, pulmonary fibrosis, asthma, any other chronic lung disease; 5) For healthy controls, subjects are non-NSCLC, nonpulmonary call-backs from collection sites (could have other disease). For NSCLC subjects that are post diagnostic procedure and diagnosis aware, the median time from the diagnostic procedure was 26 days and samples were collected either during the post-diagnosis informational visit or immediately pre-treatment. Data collected included: 1) Nanoparticle-panel data: 10 particle types were incubated in depleted plasma ("DP"), samples were randomized across 4 plates per particle type/DP, and data collected included assay process and mass spectrometry (MS) injection controls; 2) Targeted MS data: assays were developed and implemented for 51 peptides from 31 proteins based on known panels; and 3) ELISA data: assays were implemented for 2 candidate proteins including CA-125 and CK19. 288 subjects were included in the study over a 9-week period.

24 sites were used to collect subject samples grouped into NSCLC stages 1, 2, 3 (early), NSCLC stage 4 (late), or healthy and pulmonary co-morbid control arms. Samples included plasma and serum tubes, PAXgene RNA tubes, and Streck blood cell collection tubes. A randomly selected cohort of 288 age- and gender-matched subjects used for NP protein profiling. Peptides from the proteins bound by the NPs were evaluated by data-independent-acquisition mass spectrometry (DIA-MS). Depleted plasma was also prepared for analysis. 268 subject samples gave complete datasets for all 10 particle types in the panel and depleted plasma; (80 healthy, 80 co-morbid control, 61 early NSCLC (Stages 1, 2 and 3) and 47 late NSCLC (Stage 4). MS data acquisition took 7 weeks for all 288 samples. Historically, depleted plasma-only analysis has not been productive. The depth of protein profiling by the particle panel allowed for the in silico removal of all proteins associated with depleted plasma before classifier analysis. This focused analysis on novel proteins not otherwise observable in a study this size. Classification analysis was performed for each pairwise comparison of the study arms using ten rounds of 10-fold cross-validation with random forest models.

Subjects were age- and gender-matched and data from multiple sites were included within each class (co-morbid, healthy, NSCLC Stage 1 "NSCLC_1," NSCLC Stage 2 "NSCLC_2," NSCLC Stage 3 "NSCLC_3," and NSCLC Stage 4 "NSCLC_4") to avoid bias. FIG. 1 shows the age and gender breakout for the 268 subjects in the NSCLC biomarker discovery study. NSCLC Stages 1, 2, and 3 were combed as "Early NSCLC" to boost power for the creating the classifier. The study had no age or gender bias by class in the 141 subjects used for healthy (80 subjects) versus NSCLC (61 subjects) classification studies, as shown in TABLE 3.

TABLE 3

Age and Gender Statistical Validation

| Variable | P-value | Test |
|---|---|---|
| Age | 0.26 | T-Test |
| Gender | 0.17 | Fisher Test |

A summary of the particle types in the 10-particle type panel are shown below in TABLE 4, all of which are superparamagnetic.

TABLE 4

10-Particle Type Panel

| Particle Type | Particle Description |
|---|---|
| P-033 | Carboxylate, surfactant free; Functional Group: Carboxyl |
| S-010 | Poly(acrylic acid), PAA; Functional Group: Carboxyl |
| P-073 | Dextran based coating, 0.13 µm; Functional Group: Dextran |
| P-039 | Polystyrene carboxyl functionalized; Functional Group: Carboxyl |
| S-007 | Poly(dimethyl aminopropyl methacrylamide) (Dimethylamine); Functional Group: PDMAPMA |
| P-053 | Amino, 0.4-0.6 um; Functional Group: Amine |
| P-047 | Silica, 200 nm; Functional Group: Silanol |
| P-065 | Silica; Functional Group: Silanol |
| S-006 | N-(3-Trimethoxysilylpropyl)diethylenetriamine; Functional Group: Amine |
| S-003 | Silica; Functional Group: Silanol |

Figure 2:
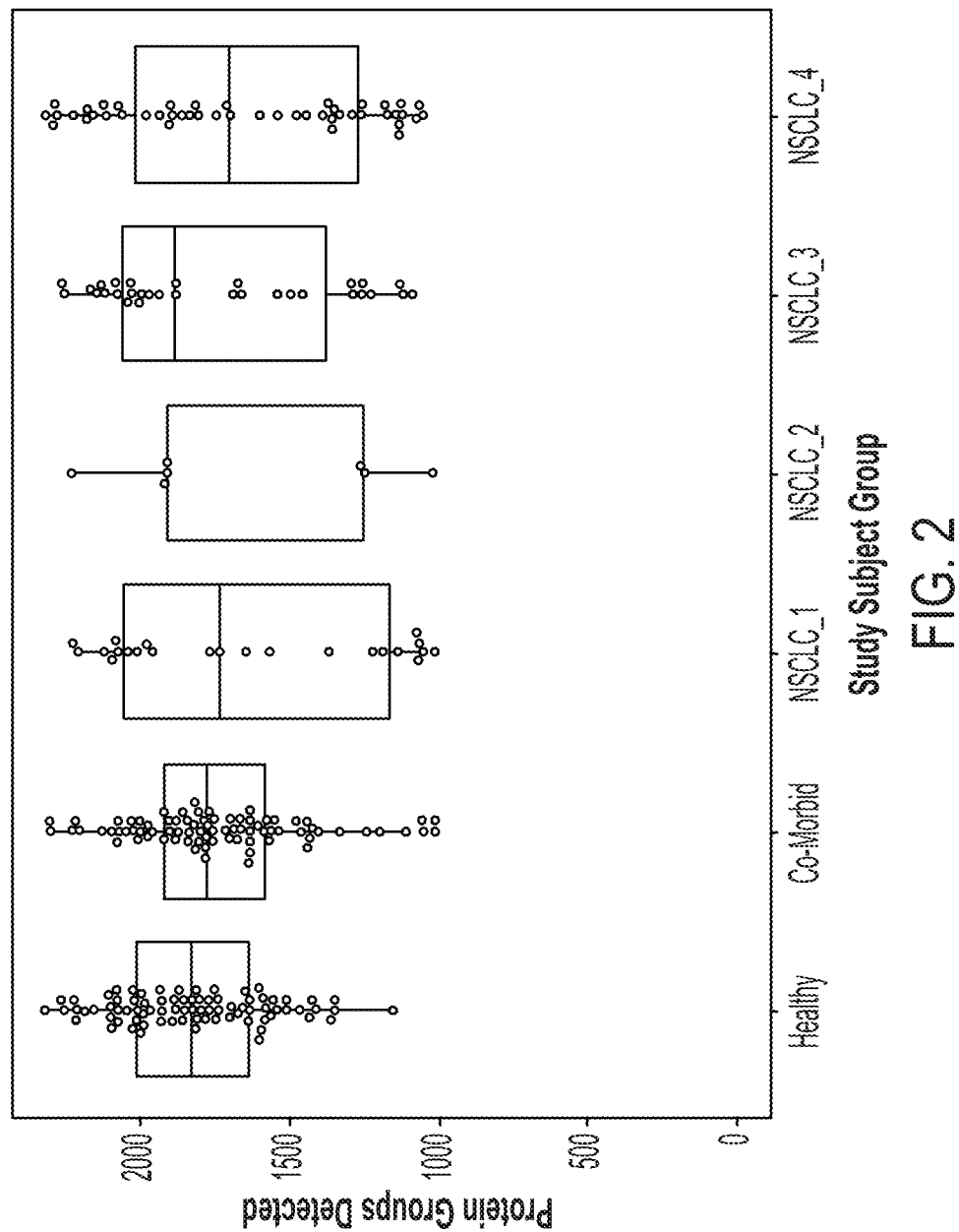
FIG. 2 shows protein counts by each study group including healthy, co-morbid, NSCLC Stage 1 "NSCLC_1," NSCLC Stage 2 "NSCLC_2," NSCLC Stage 3 "NSCLC_3," and NSCLC Stage 4 "NSCLC_4".
Figure 3:
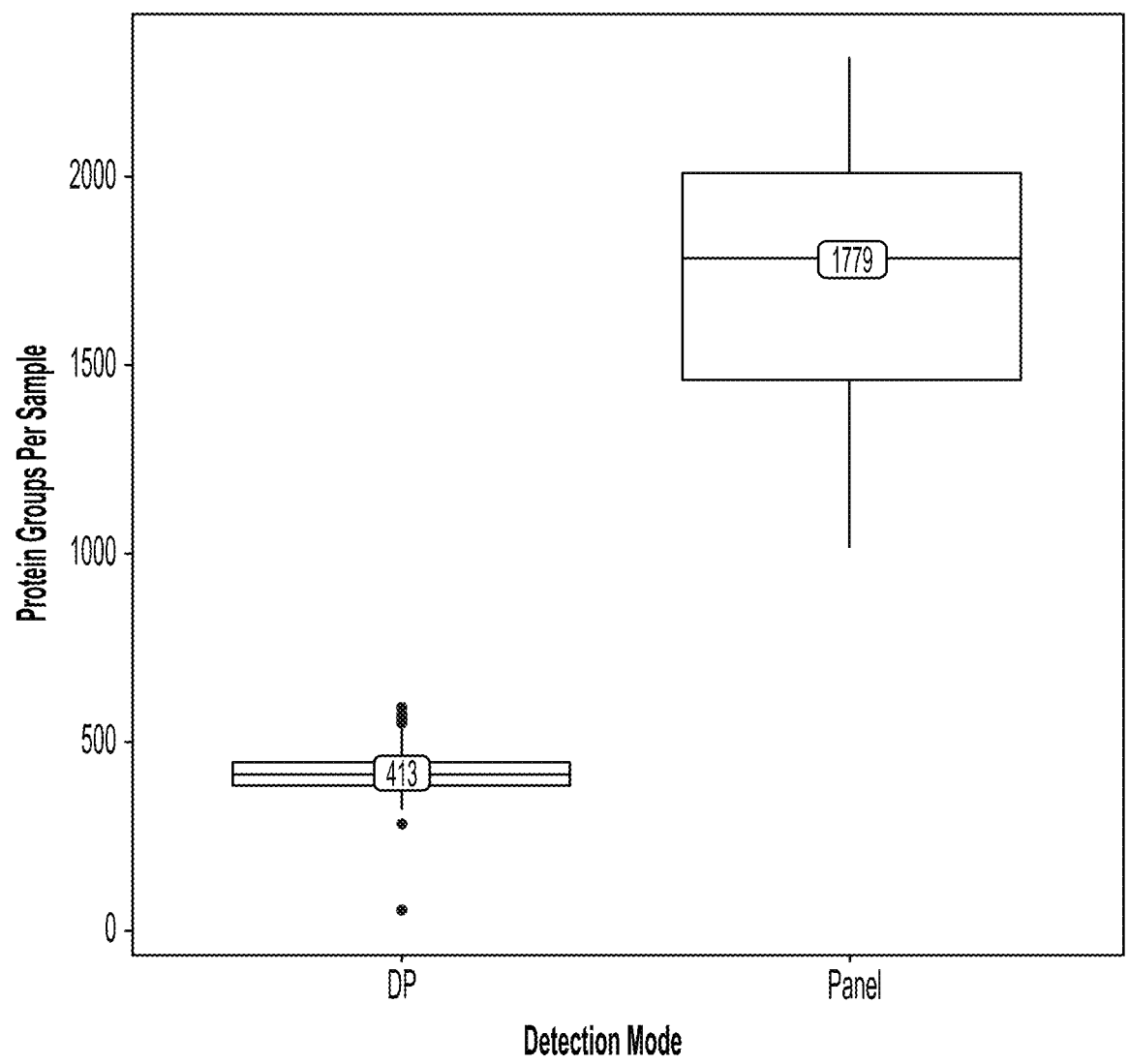
FIG. 3 shows the protein counts for depleted plasma DP and the particle panel.

Initial observations from the NSCLC study quantified the number of proteins that were observed using the 10-particle type panel. The average protein count observed using the 10-particle type panel across the samples was 1,797±337. FIG. 2 shows protein counts by each study group including healthy, co-morbid, NSCLC Stage 1 "NSCLC_1," NSCLC Stage 2 "NSCLC_2," NSCLC Stage_3 "NSCLC 3," and NSCLC Stage 4 "NSCLC_4". FIG. 3 shows the protein counts for depleted plasma DP and the particle panel.

Figure 4:
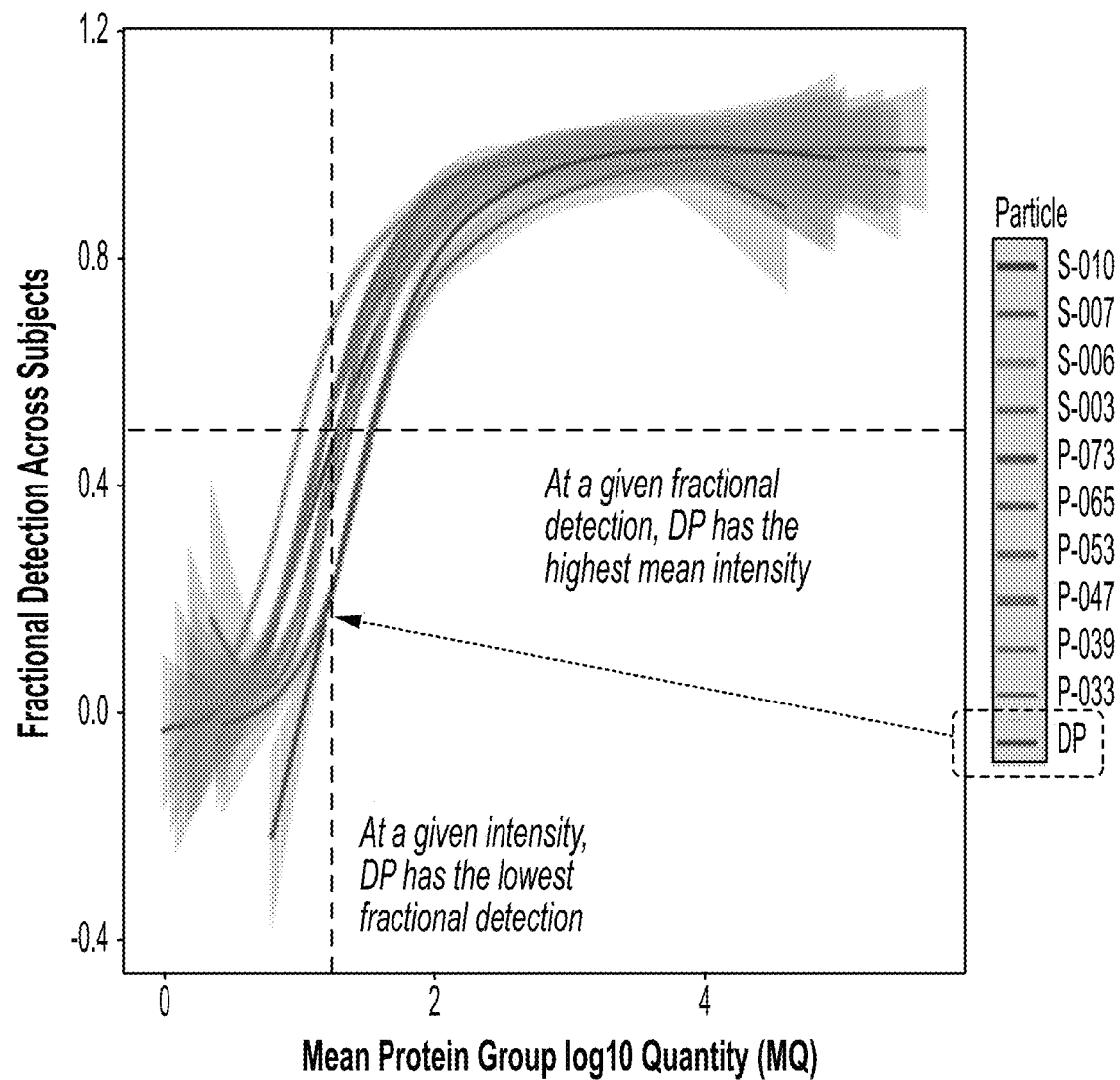
FIG. 4 shows the resulting summary of fractional detection of a protein across subjects versus mean abundance of said protein for all 10 particle types in the particle panel and depleted plasma (DP).

It was observed that particles achieved superior protein detection consistency as compared to depleted plasma on a like-intensity basis. The variation in protein group detection as a function of intensity was evaluated. The proteins detected in healthy subjects from the NSCLC study (n=82) were scored by particle type including the number of subjects in which a given protein was detected and the mean signal intensity for that protein. FIG. 4 shows the resulting summary of fractional detection of a protein across subjects versus mean abundance of said protein for all 10 particle types in the particle panel and depleted plasma (DP). Curves are smoothed fits of the data. As shown in FIG. 4 particles outperformed depleted plasma for detection consistency. At a given intensity, depleted plasma exhibited the lowest fractional detection of a protein across samples.

On average 1,779 proteins were detected from each of the 268 subject samples with the multi-particle type panel as compared to only 413 with depleted plasma.

Figure 5:
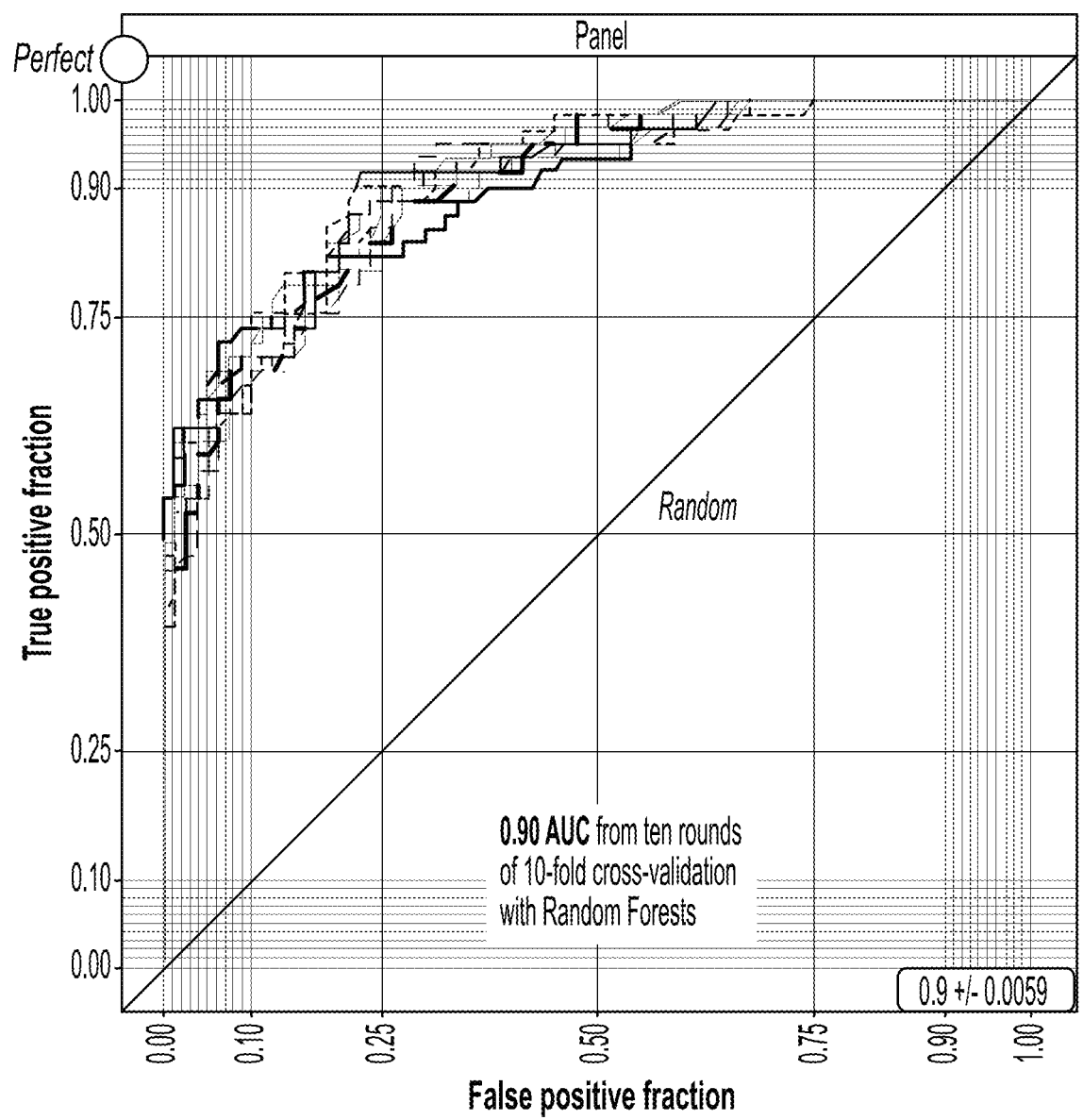
FIG. 5 shows the performance of the cross-validated particle panel classifier with the x-axis showing the fraction of classifications that are false positives and the y-axis showing the fraction of classifications that are true positives.
Figure 6:
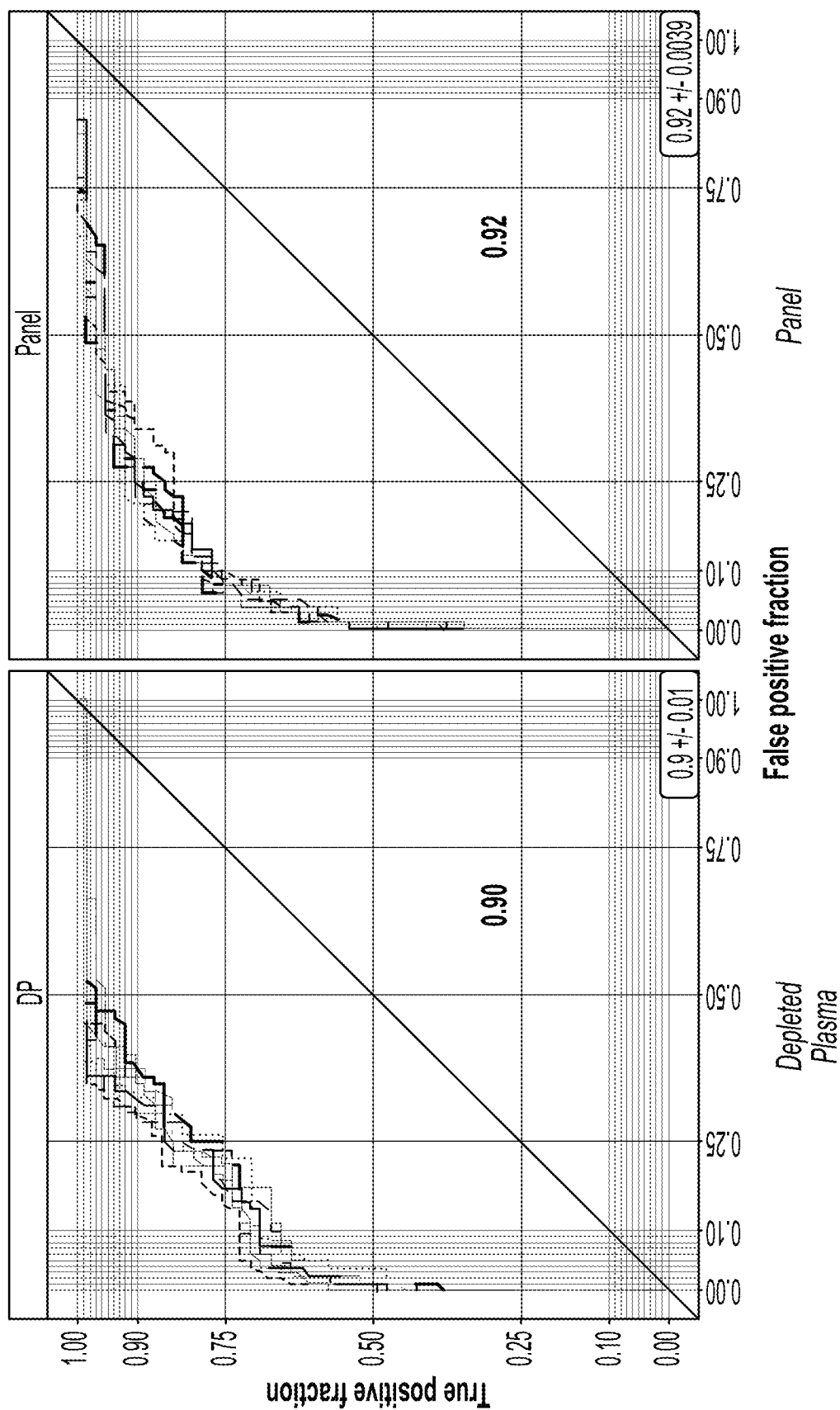
FIG. 6 shows a graph of random forest models for healthy vs NSCLC (Stages 1, 2, and 3) for depleted plasma (on left) and the 10-particle panel (right) and depict the false positive fraction on the x-axis and the true positive fraction on the y-axis.

Classification for Healthy vs. Early NSCLC (Stage 1, 2, 3). Initial classifier builds showed equivalent, high performance between depleted plasma ("DP") and the 10-particle type panel ("Panel"). Examination of important features for both methods reveals possible acute-phase-response (APR) or stress-related proteins as drivers for initial classification. The diagnostic procedure itself and diagnosis-awareness in subjects may be triggering APR and other stress-related proteins as (artifactual) classifier signals. Removing any particle panel feature related to a protein also found in depleted plasma removed potential bias. This option not available to "shallow" profiling efforts. The final cross-validated classifier leveraged the deep profiling available with the particle panel. FIG. 5 shows the performance of the cross-validated particle panel classifier with the x-axis showing the fraction of classifications that are false positives and the y-axis showing the fraction of classifications that are true positives. APR and stress protein bias was observed in depleted plasma and the 10-particle type panel ("Panel"). As shown below in TABLE 5 and TABLE 6, top features were identified as associated with APR and related proteins, which were the prime drivers of initial classification. The importance scores indicate APR proteins, specifically CRP, drove the initial performance of the classifier. FIG. 6 shows a graph of random forest models for healthy vs NSCLC (Stages 1, 2, and 3) for depleted plasma (on left) and the 10-particle type panel (right) and depict the false positive fraction on the x-axis and the true positive fraction on the y-axis.

TABLE 5

Depleted Plasma

| Importance | UniProt | Entry name | Protein names |
|---|---|---|---|
| *100.0 | P02741 | CRP_HUMAN | C-reactive protein |
| ¥14.5 | P00739 | HPTR_HUMAN | Haptoglobin-related protein |
| ¥10.5 | P00738 | HPT_HUMAN | Haptoglobin |
| 7.0 | P03952 | KLKB1_HUMAN | Plasma kallikrein |
| †5.4 | P06702 | S10A9_HUMAN | Protein S100-A9 |
| 4.5 | P13591 | NCAM1_HUMAN | Neural cell adhesion molecule 1 |
| †4.2 | P05109 | S10A8_HUMAN | Protein S100-A8 |
| 4.0 | Q9NTJ3 | SMC4_HUMAN | Structural maintenance of chromosomes protein 4 |
| 3.6 | P69905 | HBA_HUMAN | Hemoglobin subunit alpha |
| 3.3 | P26992 | CNTFR_HUMAN | Ciliary neurotrophic factor receptor subunit alpha |
| 2.8 | P02654 | APOC1_HUMAN | Apolipoprotein C-I |
| 2.7 | O95445 | APOM_HUMAN | Apolipoprotein M |
| 2.6 | P54289 | CA2D1_HUMAN | Voltage-dependent calcium channel subunit alpha-2/delta-1 |
| 2.4 | Q96KN2 | CNDP1_HUMAN | Beta-Ala-His dipeptidase |
| 2.2 | Q9BWP8 | COL11_HUMAN | Collectin-11 |

TABLE 5-continued

Depleted Plasma

| Importance | UniProt | Entry name | Protein names |
|---|---|---|---|
| 2.1 | P02750 | A2GL_HUMAN | Leucine-rich alpha-2-glycoprotein |
| 2.0 | P60709 | ACTB_HUMAN | Actin, cytoplasmic 1 |
| 2.0 | P63261 | ACTG_HUMAN | Actin, cytoplasmic 2 |
| 1.7 | P29622 | KAIN_HUMAN | Kallistatin |
| 1.7 | P55290 | CAD13_HUMAN | Cadherin-13 |
| 1.7 | P19823 | ITIH2_HUMAN | Inter-alpha-trypsin inhibitor heavy chain H2 |

TABLE 6

10-Particle Type Panel

| Importance | UniProt | Entry name | Protein names |
|---|---|---|---|
| †400.0 | P06702 | S10A9_HUMAN | Protein S100-A9 |
| *84.8 | P02741 | CRP_HUMAN | C-reactive protein |
| 62.1 | P19823 | ITIH2_HUMAN | Inter-alpha-trypsin inhibitor heavy chain H2 |
| †52.6 | P05109 | S10A8_HUMAN | Protein S100-A8 |
| †49.7 | P05109 | S10A8_HUMAN | Protein S100-A8 |
| †49.7 | P06702 | S10A9_HUMAN | Protein S100-A9 |
| *49.7 | P02741 | CRP_HUMAN | C-reactive protein |
| †46.4 | P06702 | S10A9_HUMAN | Protein S100-A9 |
| *36.7 | P02741 | CRP_HUMAN | C-reactive protein |
| *36.0 | P05109 | S10A8_HUMAN | Protein S100-A8 |
| 26.3 | Q92743 | HTRA1_HUMAN | Serine protease HTRA1 |
| 22.7 | Q8NI99 | ANGL6_HUMAN | Angiopoietin-related protein 6 |
| †18.4 | P05109 | S10A8_HUMAN | Protein S100-A8 |
| ¥16.1 | P00739 | HPTR_HUMAN | Haptoglobin-related protein |
| 15.4 | P55774 | CCL18_HUMAN | C-C motif chemokine 18 |
| 14.1 | P55774 | CCL18_HUMAN | C-C motif chemokine 18 |
| 13.7 | P60709 | ACTB_HUMAN | Actin, cytoplasmic 1 |
| 13.7 | P63261 | ACTG_HUMAN | Actin, cytoplasmic 2 |
| 13.0 | P0DJI8 | SAA1_HUMAN | Serum amyloid A-1 protein |
| *12.7 | P02741 | CRP_HUMAN | C-reactive protein |
| 12.5 | P01834 | IGKC_HUMAN | Immunoglobulin kappa constant |

*CRP
¥Haptoglobin
†S10a8/9

The final classifier included features that highlight the importance of unbiased proteomics. This final classifier used proteins know to have high importance and low importance to NSCLC as well as proteins that had no prior importance to NSCLC. TABLE 7 shows the proteins in the final classifier. The OT Score is the OpenTargets database score for the protein. An OT Score of 0 indicates that there is no entry of that protein in OpenTargets for lung cancer. These proteins are newly discovered features from the above described study. Higher OT scores are effective confirmation that the classifier is built on proteins that are associated with lung cancer. For example, TBA1A and SDC1 are drug targets for lung cancer, and are apart of the classifier.

TABLE 7

Most Important Proteins in Final Classifier

| Importance | UniProt | Entry name | Protein names | OT Score |
|---|---|---|---|---|
| 100.0 | Q8NI99 | ANGL6_HUMAN | Angiopoietin-related protein 6 | 0 |
| 73.8 | Q92743 | HTRA1_HUMAN | Serine protease HTRA1 | 0.012 |
| 51.6 | Q92743 | PXDN_HUMAN | Peroxidasin homolog | 0.017 |
| 49.3 | P55774 | CCL18_HUMAN | C-C motif chemokine 18 | 0.15 |
| 44.6 | P55774 | CCL18_HUMAN | C-C motif chemokine 18 | 0.15 |
| 44.2 | Q92743 | HTRA1_HUMAN | Serine protease HTRA1 | 0.012 |
| 41.4 | Q92743 | HTRA1_HUMAN | Serine protease HTRA1 | 0.012 |
| 36.1 | P58335 | ANTR2_HUMAN | Anthrax toxin receptor 2 | 0.04 |

TABLE 7-continued

Most Important Proteins in Final Classifier

| Importance | UniProt | Entry name | Protein names | OT Score |
|---|---|---|---|---|
| 35.2 | Q71U36 | TBA1A_HUMAN | Tubulin alpha-1A chain | 1 |
| 32.5 | P18827 | SDC1_HUMAN | Syndecan-1 | 0.6 |
| 32.3 | P0DJI9 | SAA2_HUMAN | Serum amyloid A-2 protein | 0.016 |
| 30.2 | P13611 | CSPG2_HUMAN | Versican core protein | 0.05 |
| 29.2 | Q9H6X2 | ANTR1_HUMAN | Anthrax toxin receptor 1 | 0.02 |
| 25.1 | P18827 | SDC1_HUMAN | Syndecan-1 | 0.6 |
| 24.7 | Q6P988 | NOTUM_HUMAN | Palmitoleoyl-protein carboxylesterase NOTUM | 0 |
| 21.0 | O75339 | CILP1_HUMAN | Cartilage intermediate layer protein 1 | 0 |
| 19.9 | P17655 | CAN2_HUMAN | Calpain-2 catalytic subunit | 0.041 |
| 18.6 | P05387 | RLA2_HUMAN | 60 S acidic ribosomal protein P2 | 0 |
| 16.6 | P15907 | SIAT1_HUMAN | Beta-galactoside alpha-2,6-sialyltransferase 1 | 0.43 |
| 16.4 | P13224 | GP1BB_HUMAN | Platelet glycoprotein Ib beta chain | 0 |

Comparison of the top features comprising the NSCLC classifiers to the co-morbid classifier indicated significant differences that can enable clinical differentiation. Furthermore, examination of the NSCLC top 20 classifier features highlights proteins both known and unknown to play a role in NSCLC as judged by OpenTargets (OT) annotation.

Figure 7A:
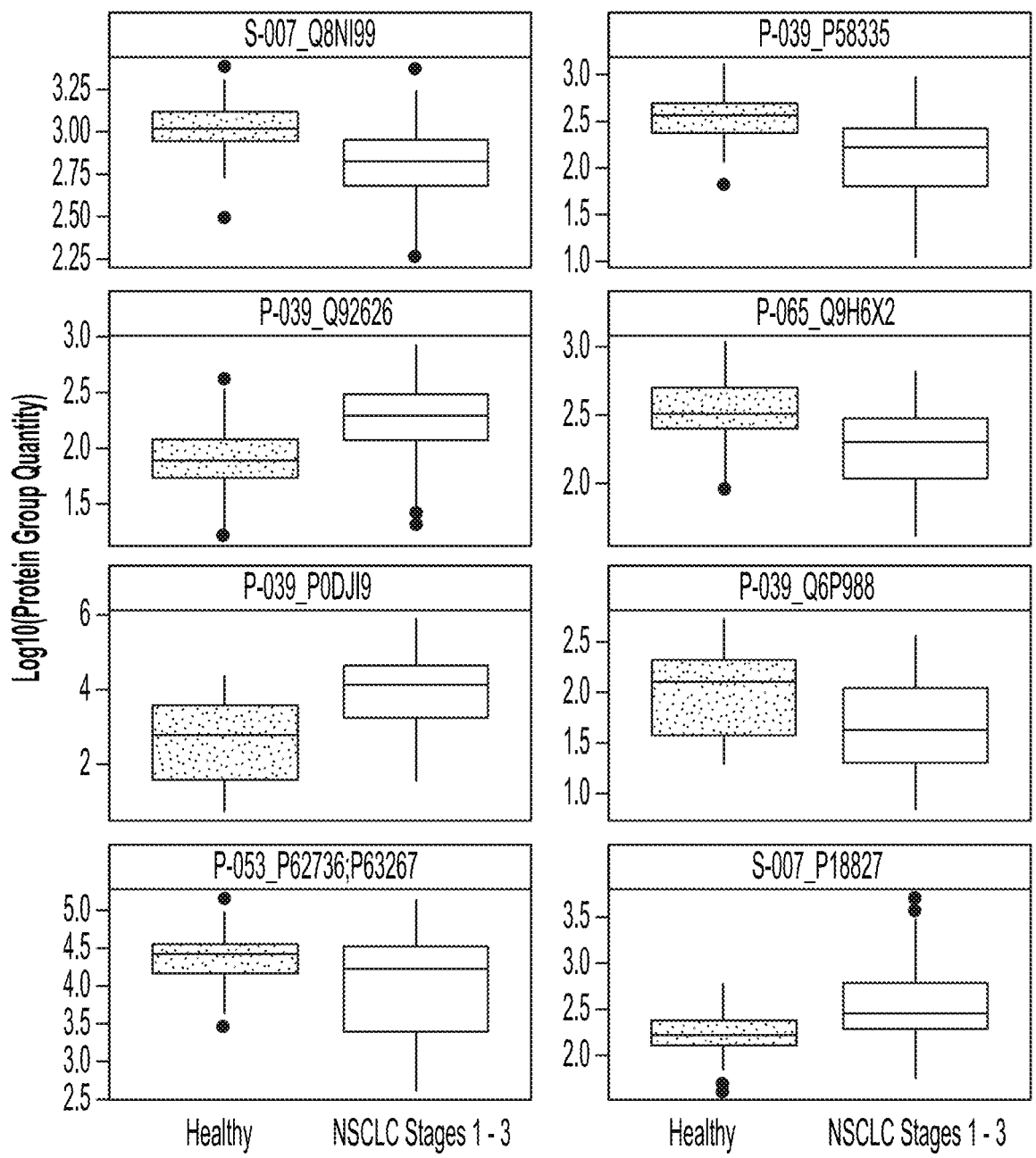
FIG. 7A-7C show the performance of classifier features across study samples.
Figure 7B:
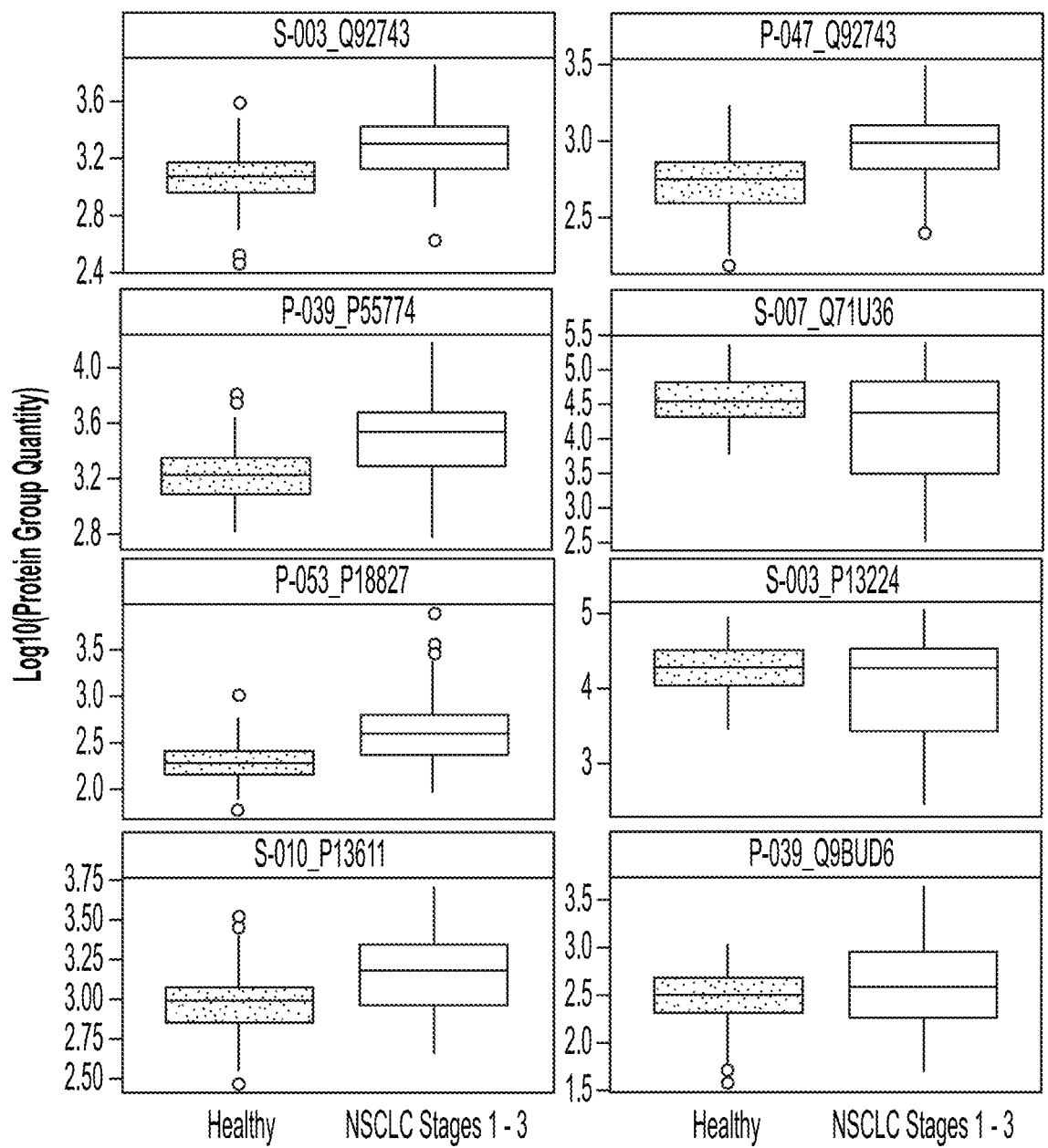
Figure 7C:
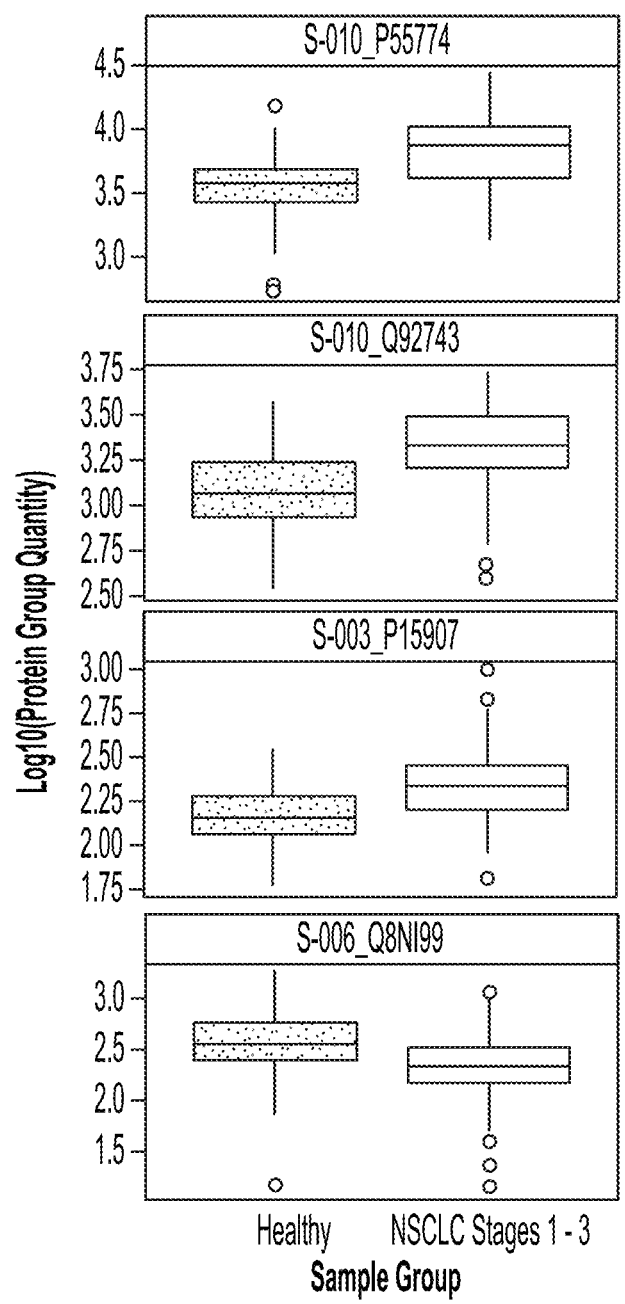

FIG. 7A-7B show the performance of classifier features across study samples. In each graph, the differences in protein levels for the top 20 features are shown across all subject data for various particle types. A 0.3 difference on the y-axis represents an approximate 2-fold change in protein levels. Data was suitable for ELISA confirmation.

Figure 8:
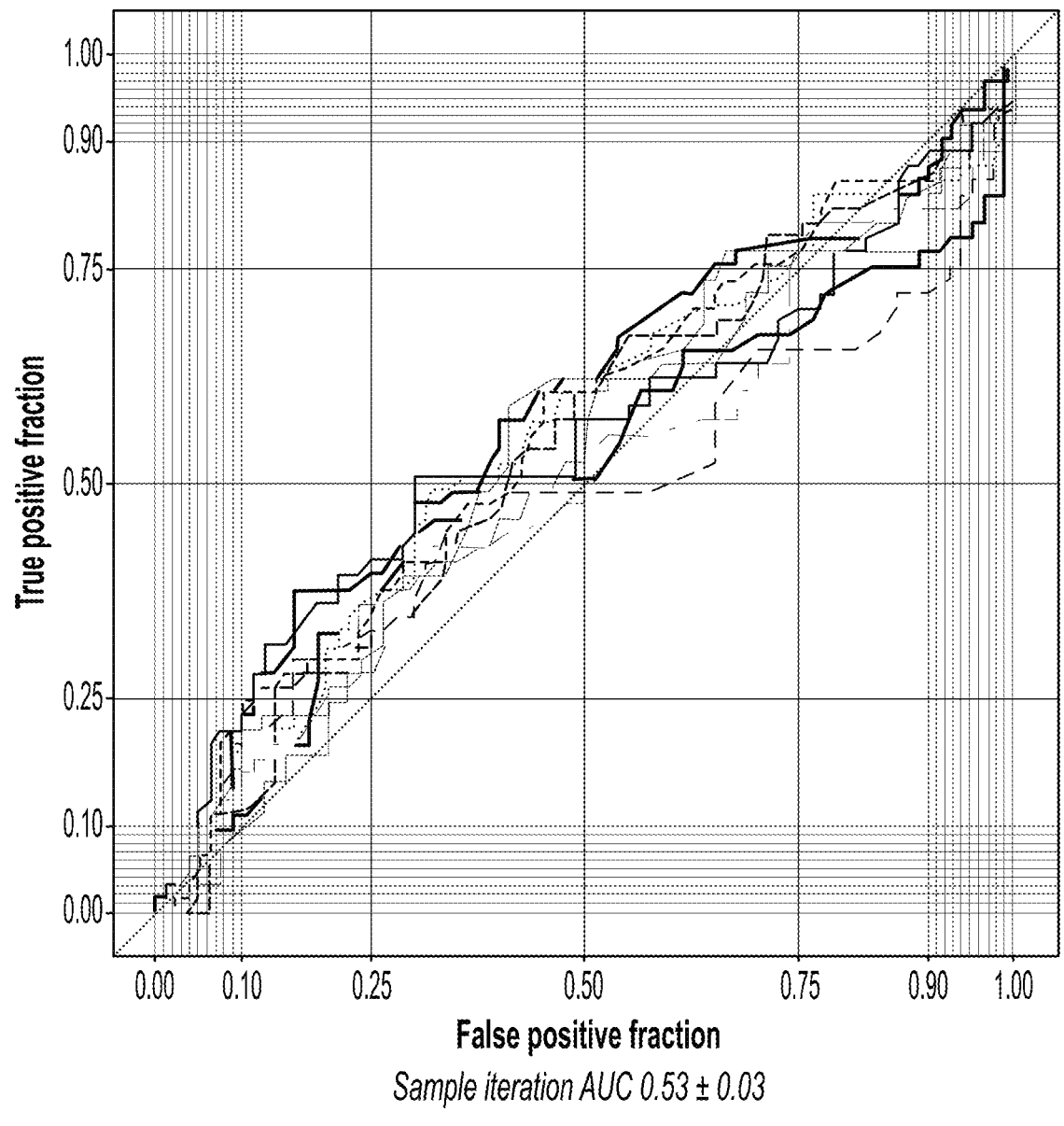
FIG. 8 shows the results from 10 iterations of 10 rounds of 10-fold cross-validation with subject class assignments randomized with the false positive fraction on the x-axis and the true positive fraction on the y-axis.

FIG. 8 shows the results from 10 iterations of 10 rounds of 10-fold cross-validation with subject class assignments randomized with the false positive fraction on the x-axis and the true positive fraction on the y-axis. As taking measurements on a few number of samples can lead to over-fitting, in which some features separate two groups by random chance, ten rounds of 10-fold cross validation was carried out to avoid over-fitting. Subject classes ("healthy" or "NSCLC") were randomized 10 times. Each time, a new ten rounds of 10-fold cross-validation was performed. Data shown in FIG. 8 are features present in the 10-particle type panel protein data set after proteins found in depleted plasma were removed. The average area under the curve (AUC) for the class randomized classifiers was 0.52±0.04 (Max: 0.58). No overfitting was observed in the Random Forest classifier builds.

Figure 9:
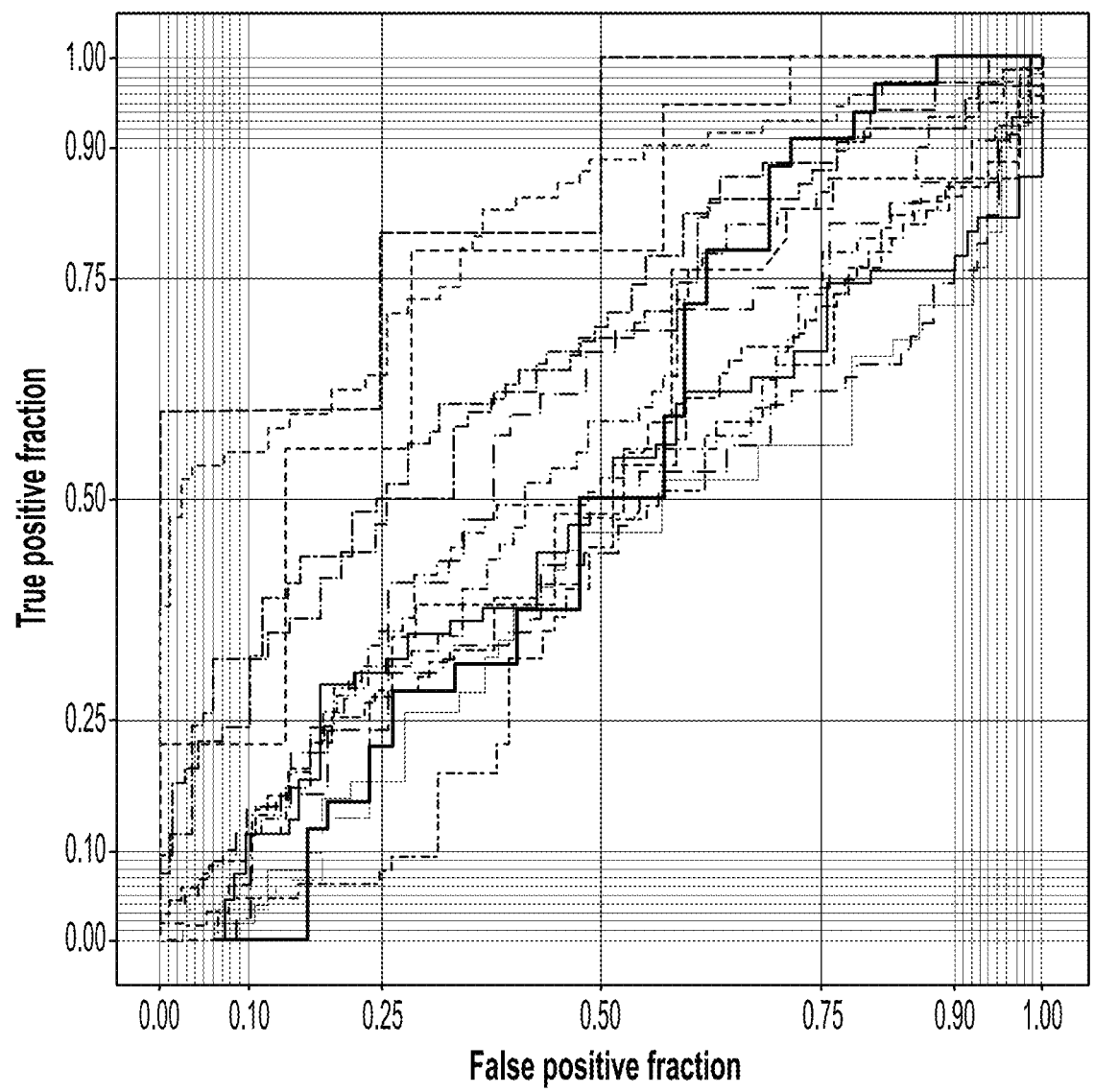
FIG. 9 shows ROC plots for 13 peptides by MRM-MS and 2 proteins by ELISA, after proteins found in depleted plasma had been removed.

The performance of candidate markers via targeted mass spectrometry (MS) and ELISA was assessed. Targeted MS and ELISA were used to evaluate candidate markers identified from published NSCLC classifier panels. 51 peptides were targeted by MS and 2 proteins were detected by ELISA. Proteins detected in depleted plasma were removed from consideration, as for the particle panel data described above. FIG. 9 shows ROC plots for 13 peptides by MRM-MS and 2 proteins by ELISA, after proteins found in depleted plasma had been removed. The x-axis shows the false positive fraction and the y-axis shows the true positive fraction. TABLE 8 shows proteins detected by targeted MS and ELISA.

TABLE 8

Proteins Detected by Targeted MS and ELISA

| AUC | Uniprot | Mode |
|---|---|---|
| 0.81 | CA125 | ELISA |
| 0.67 | MMP9 | MRM |
| 0.66 | MMP9 | MRM |
| 0.63 | *CEAM5 | MRM |
| 0.60 | *CEAM5 | MRM |
| 0.58 | IL6RA | MRM |
| 0.58 | GSLG1 | MRM |
| 0.57 | CK19 | ELISA |
| 0.55 | SPB4 | MRM |
| 0.55 | FRIL | MRM |
| 0.53 | MIF | MRM |
| 0.52 | ENOG | MRM |
| 0.51 | HS90A | MRM |
| 0.51 | SCF | MRM |
| 0.50 | ENOG | MRM |

*CEA

Figure 10:
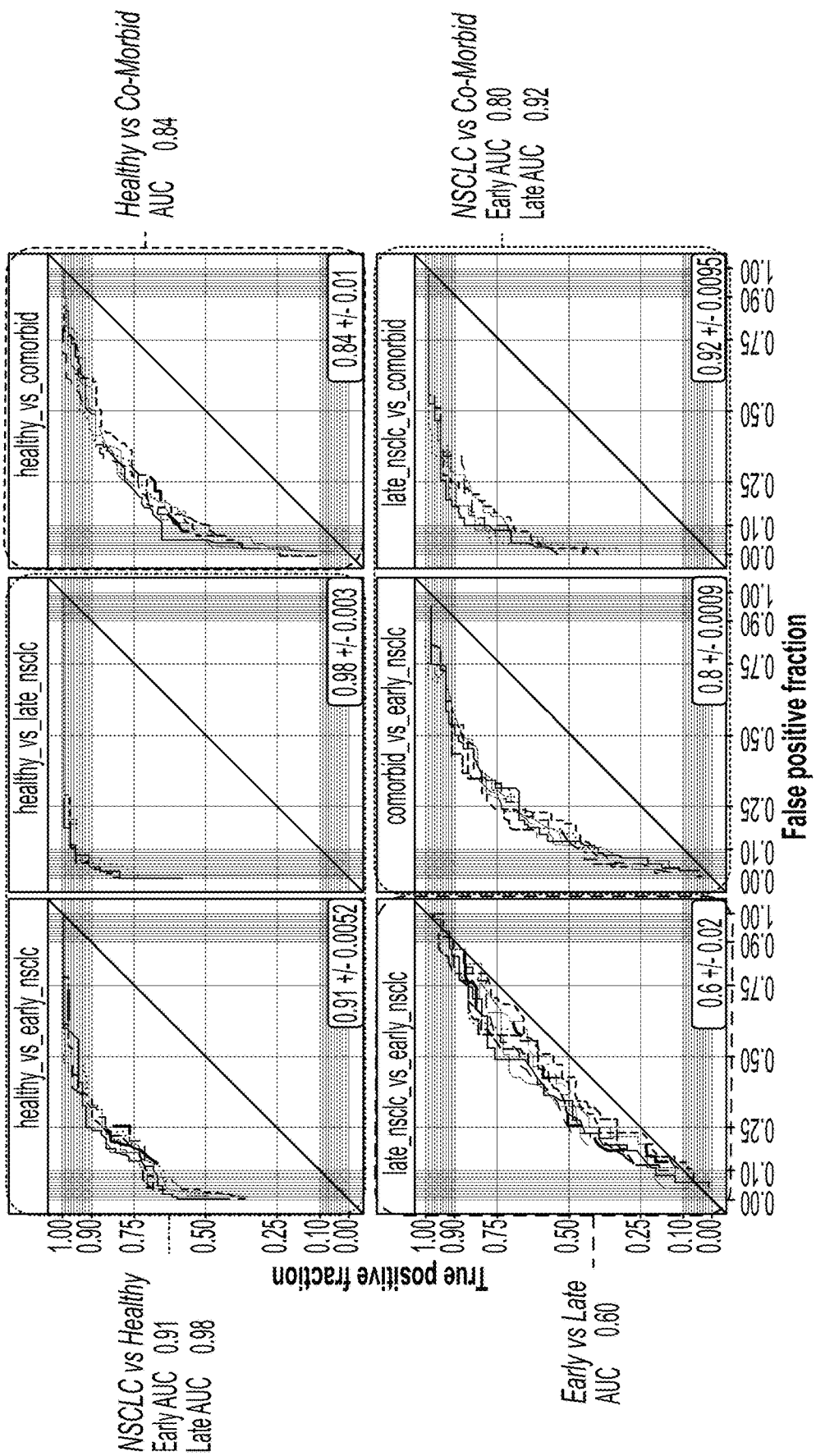
FIG. 10 shows Random Forest models for all study group comparisons.

FIG. 10 shows Random Forest models for all study group comparisons. Classifiers for all study group comparisons included ten rounds of 10-fold cross-validation after removal of depleted plasma-related features in all classifier builds. The healthy versus early NSCLC random classification after depleted plasma-related protein removal achieved an average AUC of 0.90. The comparison of the same healthy subjects to the late NSCLC and co-morbid subjects achieved average AUCs of 0.98 and 0.84, respectively.

FIG. 11A-11B show the differentiation of important features in study group comparisons. A comparison of proteins related to the top 20 features for each of the 6 pair-wise groupings is depicted.

Figure 14:
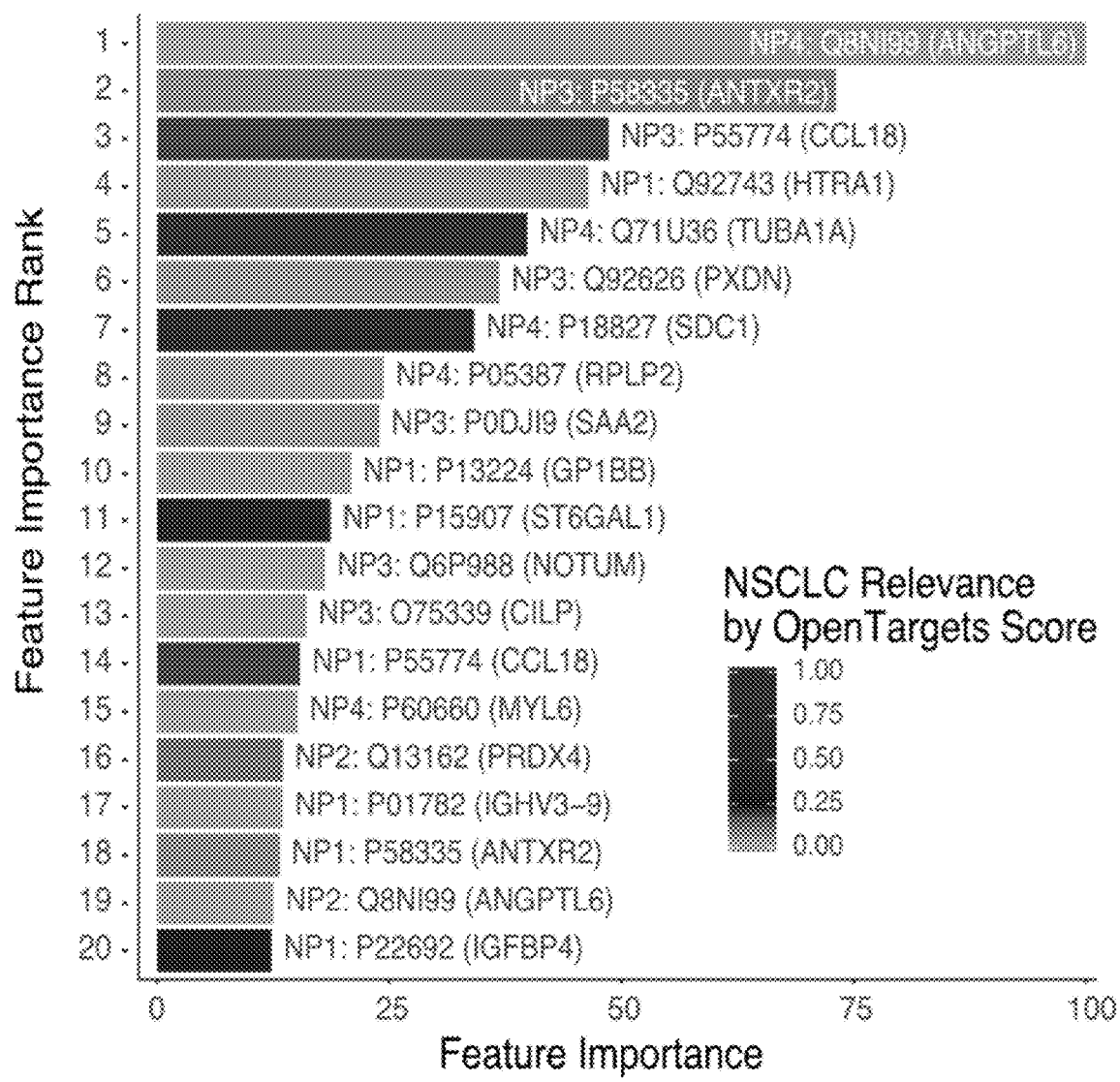
FIG. 14 shows examples of some biomarkers for use in a classifier described herein.

In one analysis shown in FIG. 14, 13 out of the 17 top proteins in a classifier (76%) were secreted proteins. In that analysis, in plasma, ~28% of the proteins picked up in reference plasma by Proteograph were secreted proteins. Secreted proteins may play important roles in mechanisms of cancer disease and treatment. Some cancer driver mutations are for intracellular (e.g. BRAF, KRAS, PIK3CA, TP53) or receptor proteins (e.g. EGFR). FIG. 15 includes some optional details about some biomarkers.

Example 2

Detection of Lung Cancer

This example illustrates detection of lung cancer with using a classifier trained to distinguish between various biological states using the biomarkers disclosed herein. A drug is engineered to target any one of the biomarkers listed in TABLE 7, including ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2_HUMAN, ANTR1_HUMAN, NOTUM_HUMAN, CILP1_HUMAN, CAN2_HUMAN, RLA2_HUMAN, SIAT1_HUMAN, or GP1BB_HUMAN. Optionally, the drug targets more than one of ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2_HUMAN, ANTR1_HUMAN, NOTUM_HUMAN, CILP1_HUMAN, CAN2_HUMAN, RLA2_HUMAN, SIAT1_HUMAN, or GP1BB_HUMAN.

A sample is obtained from a subject and is incubated with a particle panel disclosed herein (e.g., the 10-particle panel of TABLE 4). The particles are separated from the sample to remove unbound protein and the biomolecule coronas on the particles are analyzed by mass spectrometry for one or more of the above described biomarkers. A trained classifier, trained to distinguish between healthy, co-morbid, and NSCLC Stage 1, 2, and 3 biological states based on one or more of the above described biomarkers, is used to determine the biological state of the sample.

Example 3

Treatment of Lung Cancer

This example illustrates treatment of lung cancer with a drug targeting a biomarker disclosed herein. A drug is engineered to target any one of the biomarkers listed in TABLE 7, including ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2_HUMAN, ANTR1_HUMAN, NOTUM_HUMAN, CILP1_HUMAN, CAN2_HUMAN, RLA2_HUMAN, SIAT1_HUMAN, or GP1BB_HUMAN. Optionally, the drug targets more than one of ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2_HUMAN, ANTR1_HUMAN, NOTUM_HUMAN, CILP1_HUMAN, CAN2_HUMAN, RLA2_HUMAN, SIAT1_HUMAN, or GP1BB_HUMAN. The drug is manufactured by chemical synthesis or recombinant expression. The drug is administered to a subject in need thereof. The subject has lung cancer. Upon administration to the subject, symptoms of the lung cancer are alleviated and/or lung cancer cells are targeted and eliminated.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treatment, comprising:
obtaining a data set comprising protein information from biomolecule coronas that correspond to physicochemically distinct particles incubated with a biofluid sample from a subject suspected of having a cancer state or a comorbidity of the cancer state, wherein the protein information comprises a concentration or amount of serine protease HTRA1 (HTRA1), Peroxidasin homolog (PXDN), Anthrax toxin receptor 2 (ANTR2), Versican core protein (CSPG2), Anthrax toxin receptor 1 (ANTR1), Palmitoleoyl-protein carboxylesterase NOTUM (NOTUM), Cartilage intermediate layer protein 1 (CILP1), or Calpain-2 catalytic subunit (CAN2), and wherein the cancer state comprises non-small cell lung cancer (NSCLC) and the comorbidity of the cancer state comprises a pulmonary comorbidity;
applying a classifier to the data set to identify the biofluid sample as indicative of a healthy state, the cancer state, or the comorbidity of the cancer state, wherein the classifier distinguishes the cancer state from the comorbidity of the cancer state or distinguishes the cancer state from the healthy state, and wherein the classifier identifies the biofluid sample as indicative of the cancer state; and
administering a treatment to the subject, the treatment comprising a resection surgery to remove the cancer, an anti-cancer agent, or radiation therapy.

2. The method of claim 1, wherein the classifier is characterized by a receiver operating characteristic curve having an area under the curve of at least 0.8.

3. The method of claim 1, wherein the NSCLC comprises stage 1, 2, or 3 NSCLC.

4. The method of claim 1, wherein the subject has not yet undergone a cancer treatment.

5. The method of claim 1, wherein the pulmonary comorbidity is selected from the group consisting of: chronic obstructive pulmonary disease (COPD), emphysema, pulmonary fibrosis, asthma, a chronic lung disease, and any combination thereof.

6. The method of claim 1, wherein obtaining the data set comprises contacting the biofluid sample with the physicochemically distinct particles to form the biomolecule coronas.

7. The method of claim 1, wherein the physicochemically distinct particles comprise lipid particles, metal particles, silica particles, or polymer particles.

8. The method of claim 1, wherein obtaining the data set comprises detecting the proteins of the biomolecule coronas by mass spectrometry.

9. The method of claim 1, wherein the protein information comprises a concentration or amount of a secreted protein.

10. The method of claim 1, wherein the classifier comprises classification features comprising nanoparticle-protein pairs.

11. The method of claim 1, wherein the anti-cancer agent comprises a chemotherapy.

12. The method of claim 1, wherein the biofluid comprises plasma.

13. A method of treatment, comprising:
obtaining protein information from a biofluid sample of a subject, the protein information comprising measurements of distinct peptides of a protein group, wherein the protein information is from biomolecule coronas that correspond to physicochemically distinct particles incubated with the sample, and wherein the peptides are one or more of the biomolecule coronas, and wherein the protein information comprises a concentration or amount of serine protease HTRA1 (HTRA1), Peroxidasin homolog (PXDN), Anthrax toxin receptor 2 (ANTR2), Versican core protein (CSPG2), Anthrax toxin receptor 1 (ANTR1), Palmitoleoyl-protein carboxylesterase NOTUM (NOTUM), Cartilage intermediate layer protein 1 (CILP1), or Calpain-2 catalytic subunit (CAN2);

applying a classifier to the measurements of the distinct peptides of the protein group to identify the protein information as indicative of a healthy state, a cancer state, or a comorbidity of the cancer state, wherein the classifier distinguishes the cancer state from the comorbidity of the cancer state or distinguishes the cancer state from the healthy state, wherein the classifier identifies the biofluid sample as indicative of the cancer state, and wherein the cancer state comprises non-small cell lung cancer (NSCLC) and the comorbidity of the cancer state comprises a pulmonary comorbidity; and administering a treatment to the subject, the treatment comprising a resection surgery to remove the cancer, an anti-cancer agent, or radiation therapy.

14. The method of claim 13, wherein the protein information further comprises a second protein group measurement comprising pooled measurements of distinct peptides of the second group, and wherein the classifier is further applied to the second protein group measurement.

15. The method of claim 13, wherein the distinct peptides comprise distinct peptide sequences or post-translational modifications.

* * * * *